US010865163B2

(12) United States Patent
Young et al.

(10) Patent No.: US 10,865,163 B2
(45) Date of Patent: Dec. 15, 2020

(54) CARBON DIOXIDE AS A DIRECTING GROUP FOR C—H FUNCTIONALIZATION REACTIONS INVOLVING LEWIS BASIC AMINES, ALCOHOLS, THIOLS, AND PHOSPHINES FOR THE SYNTHESIS OF COMPOUNDS

(71) Applicant: The University of Toledo, Toledo, OH (US)

(72) Inventors: Michael C. Young, Toledo, OH (US); Mohit Kapoor, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 16/223,467

(22) Filed: Dec. 18, 2018

(65) Prior Publication Data

US 2019/0185392 A1 Jun. 20, 2019

Related U.S. Application Data

(60) Provisional application No. 62/608,074, filed on Dec. 20, 2017.

(51) Int. Cl.
 *C07B 37/02* (2006.01)
 *C07B 37/04* (2006.01)
 (Continued)

(52) U.S. Cl.
 CPC ............. *C07B 37/02* (2013.01); *C07B 37/04* (2013.01); *C07B 43/00* (2013.01); *C07B 47/00* (2013.01); *C07C 209/68* (2013.01); *C07C 211/08* (2013.01); *C07C 211/52* (2013.01); *C07C 213/08* (2013.01); *C07C 227/16* (2013.01); *C07C 231/12* (2013.01); *C07D 209/08* (2013.01); *C07D 311/76* (2013.01); *B01J 31/04* (2013.01); *B01J 31/4038* (2013.01); *B01J 2231/42* (2013.01); *B01J 2231/46* (2013.01);
(Continued)

(58) Field of Classification Search
 None
 See application file for complete search history.

(56) References Cited

U.S. PATENT DOCUMENTS

| 5,604,229 A | 2/1997 | Fujita et al. |
| 6,046,227 A | 4/2000 | Crowell et al. |
| 9,056,813 B2 | 6/2015 | Gharpure et al. |

FOREIGN PATENT DOCUMENTS

| EP | 0827746 A1 | 3/1998 |
| EP | 0921120 A1 | 6/1999 |
| WO | 2014184275 A1 | 11/2014 |

OTHER PUBLICATIONS

Luo ("Overriding Ortho-Para Selectivity via a Traceless Directing Group Relay Strategy: The Meta-Selective Arylation of Phenols" J. Am. Chem. Soc., 136, 2014, p. 4109-4112, of record in the IDS filed on Sep. 27, 2019 and further including Supporting Information pp. S1-S47) (Year: 2014).*

(Continued)

*Primary Examiner* — Amy C Bonaparte
(74) *Attorney, Agent, or Firm* — MacMillan, Sobanski & Todd, LLC

(57) ABSTRACT

Methods of synthesizing compounds using $CO_2$ as a directing group for C—H functionalization, and compounds made thereby, are described.

19 Claims, 32 Drawing Sheets
(28 of 32 Drawing Sheet(s) Filed in Color)

(51) Int. Cl.
| | |
|---|---|
| *C07B 43/00* | (2006.01) |
| *C07C 209/68* | (2006.01) |
| *C07C 211/52* | (2006.01) |
| *C07B 47/00* | (2006.01) |
| *C07C 211/08* | (2006.01) |
| *C07D 209/08* | (2006.01) |
| *C07C 213/08* | (2006.01) |
| *C07C 231/12* | (2006.01) |
| *C07C 227/16* | (2006.01) |
| *C07D 311/76* | (2006.01) |
| *B01J 31/40* | (2006.01) |
| *B01J 31/04* | (2006.01) |
| *C07B 51/00* | (2006.01) |

(52) U.S. Cl.
CPC ...... *B01J 2531/17* (2013.01); *B01J 2531/824* (2013.01); *C07B 51/00* (2013.01); *C07C 2601/08* (2017.05); *C07C 2601/14* (2017.05); *C07C 2601/18* (2017.05)

(56) References Cited

OTHER PUBLICATIONS

Fan ("Carbon Dioxide: A Reagent for the Simultaneous Protection of Nucleophilic Centres and the Activation of Alternative Locations to Electrophilic Attack. 17 . . . " J. Org. Chem. 56(17), 1991, p. 5045-5048) (Year: 1991).*

Katritsky ("Carbon Dioxide: A Reagent for the Simultaneous Protection of Nucleophilic Centres and the Activation of Alternative Locations to Electrophilic Attack. Part III . . . " Tetrahedron, 42(14), 1986, p. 4027-4034) (Year: 1986).*

Wittmann ("Supercritical Carbon Dioxide as Solvent and Temporary Protecting Group for Rhodium-Catalyzed Hydroaminomethylation" Chem. Eur. J, 7, 2001, p. 4584-4589) (Year: 2001).*

Frasco et al., "Cp*IrIII-Catalyzed Oxidative Coupling of Benzoic Acids with Alkynes", American Chemical Society Catalysis, 2013, vol. 3, pp. 2421-2429.

Hernando et al., "Palladium-Catalyzed Carbonylative Cyclization of Amines via γ-C(sp3)—H Activation: Late-Stage Diversification of Amino Acids and Peptides", American Chemical Society Catalysis, 2016, vol. 6, pp. 6868-6882.

Ling et al., "Palladium-catalyzed sequential monoarylation/amidation of C(sp3)—H bonds: stereoselective synthesis of α-amino-b-lactams and anti-α,b-diamino acid†", Royal Society of Chemistry, 2017, vol. 53, pp. 6351-6354.

Liu et al., "Site-selective C—H arylation of primary aliphatic amines enabled by a catalytic transient directing group", Nature Chemistry, Published Only Sep. 12, 2016, DOI:10.1038/NCHEM.2606, pp. 1-7.

Luo et al., "Overriding Ortho-Para Selectivity via a Traceless Directing Group Relay Strategy: The Meta-Selective Arylation of Phenols", Journal of the American Chemical Society, 2014, vol. 136, pp. 4109-4112.

Luo et al., "Salicylic acids as readily available starting materials for the synthesis of meta-substituted biaryls†", Royal Society of Chemistry, 2015, vol. 51, pp. 3127-3130.

Noiser et al., "Stapled Peptides by Late-Stage C(sp3)—H Activation", Angewandte Chem. International Edition, 2017, vol. 56, pp. 314-318.

Shabashov et al., "Auxiliary-Assisted Palladium-Catalyzed Arylation and Alkylation of sp2 and sp3 Carbon-Hydrogen Bonds", Journal of the American Chemical Society, 2010, vol. 132, pp. 3965-3972.

Wu et al., "Pd-Catalyzed γ-C(sp3)—H Arylation of Free Amines Using a Transient Directing Group", Journal of the American Chemical Society, 2016, vol. 138, pp. 14554-14557.

Xu et al., "Catalytic C(sp3)—H Arylation of Free Primary Amines with an exo Directing Group Generated In Situ", Angewandte Chem. International Edition, 2016, vol. 55, pp. 9084-9087.

Yada et al., "Buttressing Salicylaldehydes: A Multipurpose Directing Group for C(sp3)—H Bond Activation", Angewandte Chem. International Edition, 2017, vol. 56, pp. 1073-1076.

Yan et al., "Palladium(II)-catalyzed arylation of unactivated C(sp3)—H bonds by using 2,1,3-benzoselenadiazole-4-amine as directing ligand", Tetrahedron Letters, 2017, vol. 58, pp. 54-58.

Zhang et al., "Pd-Catalyzed Monoselective ortho-C—H Alkylation of N-Quinolyl Benzamides: Evidence for Stereoretentive Coupling of Secondary Alkyl Iodides", Journal of the American Chemical Society, 2015, vol. 137, pp. 531-539.

M. Young et al., "Carbon Dioxide as a Directing Group for C—H Functionalization Reactions Involving Lewis Basic Amines, Alcohols, Thiols, and Phosphines for the Synthesis of Novel Compounds of Agrochemical and Medicinal Interest", Aug. 2016, pp. 1-10.

\* cited by examiner

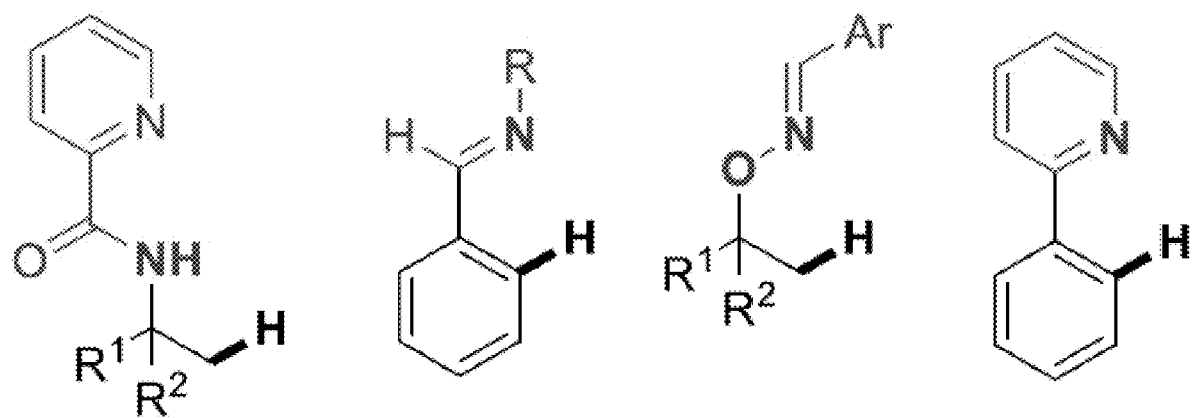
PRIOR ART FIG. 1

Amide-Based Directing Groups for Amine Functionalization

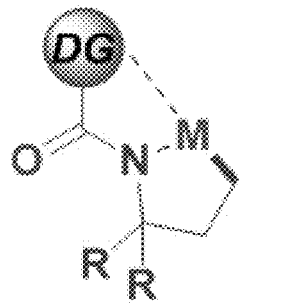 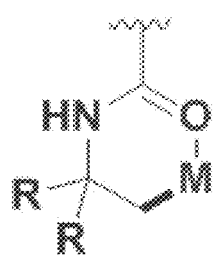

*Pros: Robust*
*Viable for 1° and 2° Amines*

*Cons: Extra Synthetic Steps*
*Poor Atom Economy*

Imine-Based Directing Groups for Amine Functionalization

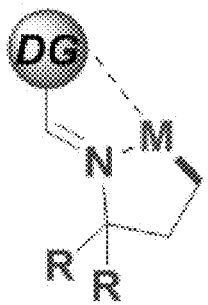

*Pros: Possibly Catalytic*
*In Situ Addition/Removal*

*Cons: Sensitive to Oxidation*

Hybrid Directing Group for Amine Functionalization

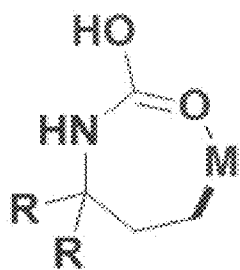

*$CO_2$ as a directing group combines the pros of amides and imines without the cons!*

FIG. 2

| Solvent | Additive | CO₂ (equiv) | Yield (%) | Temperature (°C) | Time (h) |
|---|---|---|---|---|---|
| AcOH (0.6 M) | AgTFA | 3.0 | 65 | 110 | 12 |
| AcOH (0.6 M) | AgTFA | 3.0 | 50 | 90 | 12 |
| AcOH (0.6 M) | AgTFA | 3.0 | 5 | 50 | 24 |
| AcOH (0.6 M) | AgCO₃ | 3.0 | 10 | 110 | 12 |
| AcOH (0.6 M) | AgOCOCH₃ | 3.0 | 15 | 110 | 12 |
| AcOH (0.6 M) | KOAc | 3.0 | 10 | 110 | 12 |
| AcOH (0.6 M) | - | 3.0 | 10 | 110 | 12 |
| HFIP (0.6 M) | AgTFA | 3.0 | 30 | 110 | 12 |
| ACN (0.6 M) | AgTFA | 3.0 | 20 | 110 | 12 |
| TFA (0.6 M) | AgTFA | 3.0 | 10 | 110 | 12 |
| AcOH (0.15 M) | AgTFA | 3.0 | 65 | 110 | 12 |
| AcOH (0.3 M) | AgTFA | 3.0 | 69 | 110 | 12 |
| AcOH (0.6 M) | AgTFA | 3.0 | 67 | 110 | 12 |
| AcOH (0.3 M) | NaHCO₃ | 3.0 | 0 | 110 | 12 |
| AcOH (0.3 M) | K₂CO₃ | 3.0 | 0 | 110 | 12 |
| AcOH (0.3 M) | KHCO₃ | 3.0 | 0 | 110 | 12 |
| AcOH (0.3 M) | Cs₂CO₃ | 3.0 | 0 | 110 | 12 |
| AcOH (0.3 M) | AgOTf | 1.0 | 70 | 110 | 12 |
| AcOH (0.3 M) | AgTFA | 1.0 | 73 | 110 | 12 |
| AcOH (0.3 M) | AgTFA | 2.0 | 74 | 110 | 12 |
| AcOH (0.3 M) | AgTFA | 2.0 | 46 | 110 | 6 |
| AcOH (0.3 M) | AgTFA | 2.0 | 74 | 110 | 18 |
| AcOH (0.3 M) | AgTFA | 2.0 | 72 | 110 | 24 |

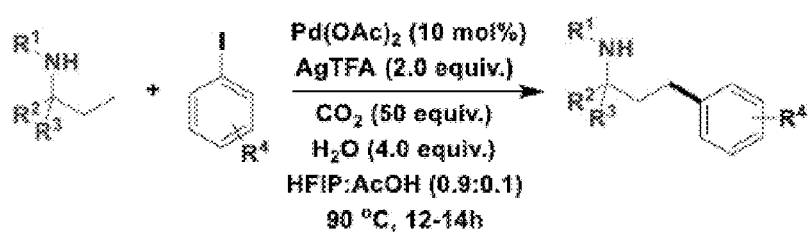

| Catalyst | CO₂ (equiv) | Halide (equiv) | Solvent | Yield (%) |
|---|---|---|---|---|
| Pd(OAc)₂ (1 mol%) | 20 | 1.5 | AcOH (1.0 mL) | No reaction (NR) |
| Pd(OAc)₂ (3 mol%) | 20 | 1.5 | AcOH (1.0 mL) | NR |
| Pd(OAc)₂ (5 mol%) | 20 | 1.5 | AcOH (1.0 mL) | NR |
| Pd(OAc)₂ (1 mol%) | 20 | 1.5 | AcOH+HFIP (0.1+0.9 mL) | NR |
| Pd(OAc)₂ (3 mol%) | 20 | 1.5 | AcOH+HFIP (0.1+0.9 mL) | NR |
| Pd(OAc)₂ (5 mol%) | 20 | 1.5 | AcOH+HFIP (0.1+0.9 mL) | 22-23% |
| PdCl₂ (10 mol%) | 20 | 1.5 | AcOH+HFIP (0.1+0.9 mL) | 6% |
| Pd(TFA)₂ (10 mol%) | 20 | 1.5 | AcOH (1.0 mL) | 4% |
| Pd(trimethylacetate)₂ (10 mol%) | 20 | 1.5 | AcOH (1.0 mL) | NR |
| Pd(OAc)₂ (10 mol%) | 20 | 1.5 | AcOH+HFIP (0.1+0.9 mL) | 30% |
| Pd(OAc)₂ (10 mol%) | 35 | 3.0 | AcOH+HFIP (0.1+0.9 mL) | 30% |
| Pd(OAc)₂ (10 mol%) | 50 | 3.0 | AcOH+HFIP (0.1+0.9 mL) | 41% |

FIG. 7

FIG. 11 – Table 1

FIG. 12 – Table 2

FIG. 13 – Table 3

On the Reversibility of Carbon Dioxide Adduct Formation During the Reaction
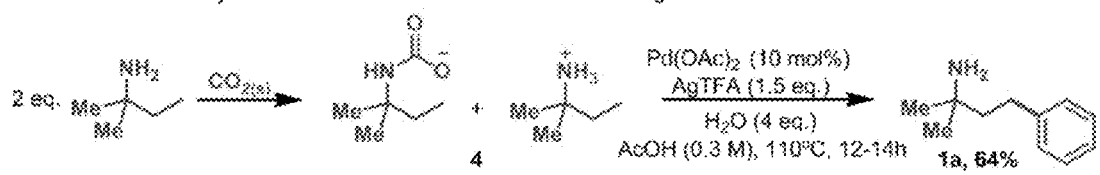
On the Reversibility of C–H Activation
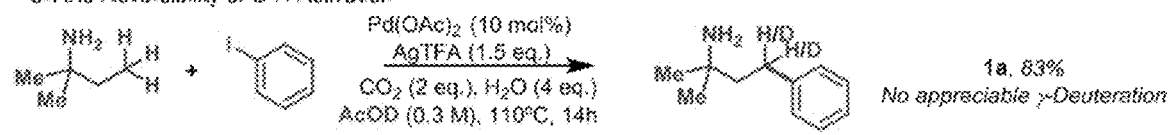
Evidence for Directing Rather Than Deactivation Effect
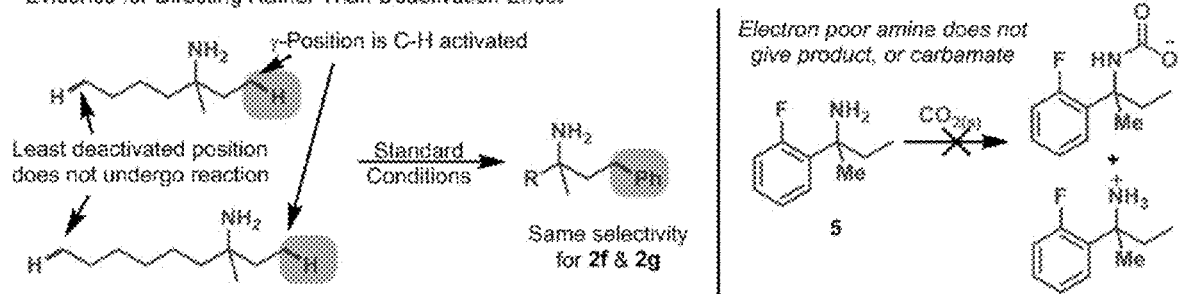
Scale-Up/Atmospheric Pressure
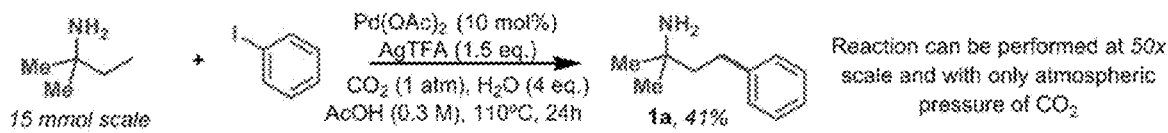
FIG. 14

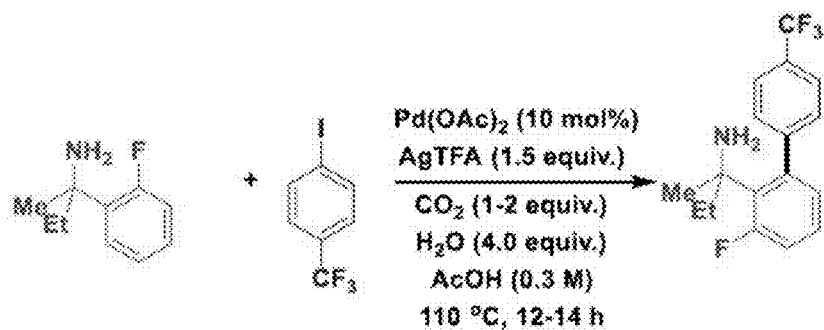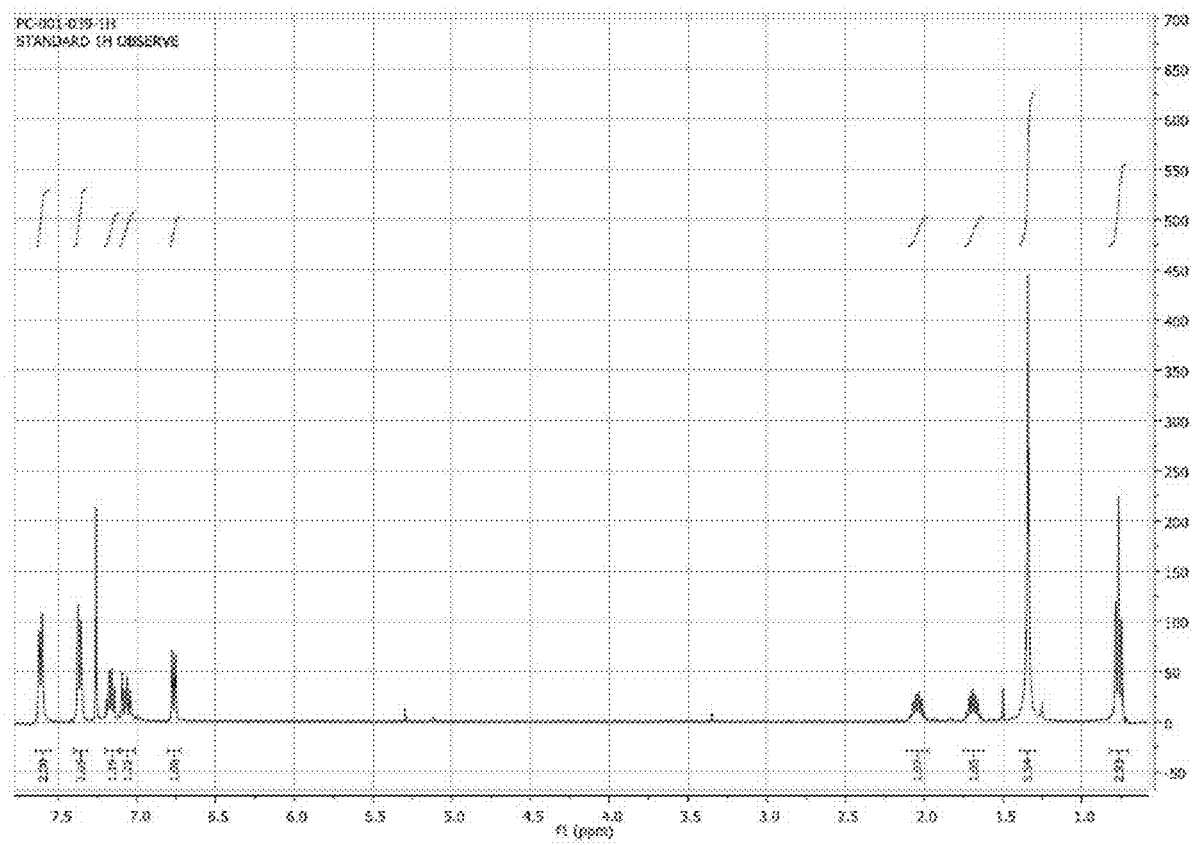
FIG. 20

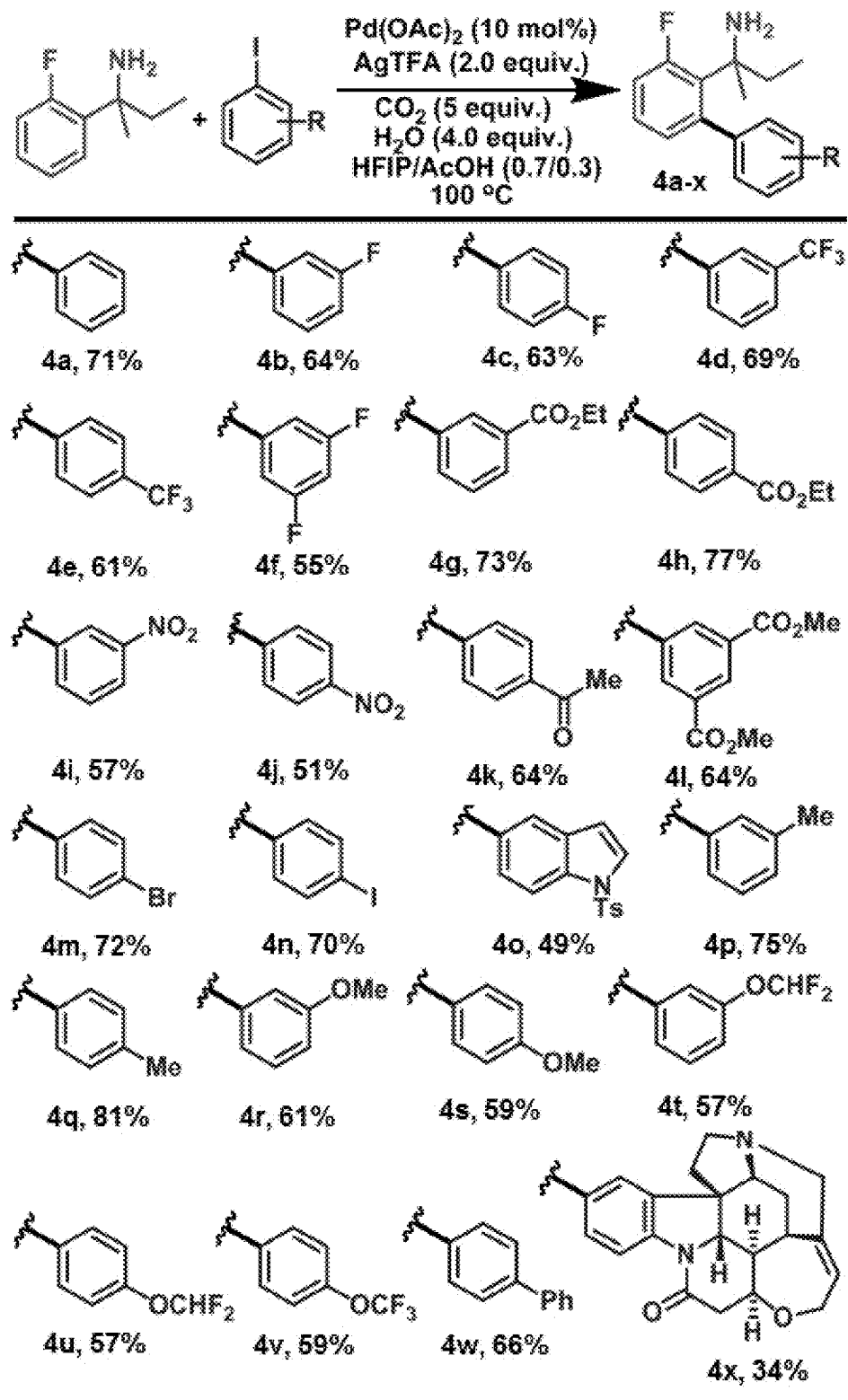
FIG. 23 – Table 4

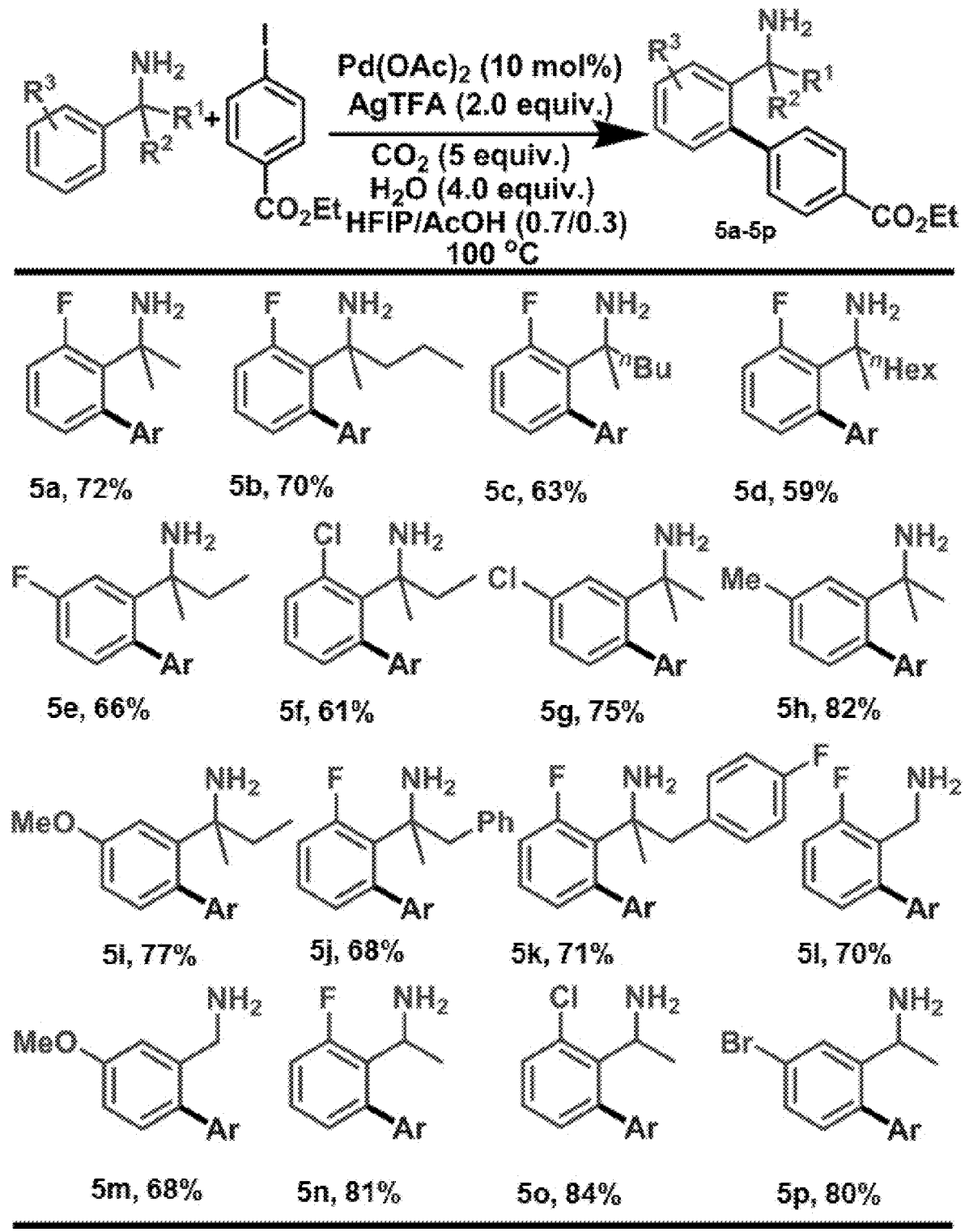
FIG. 24 – Table 5

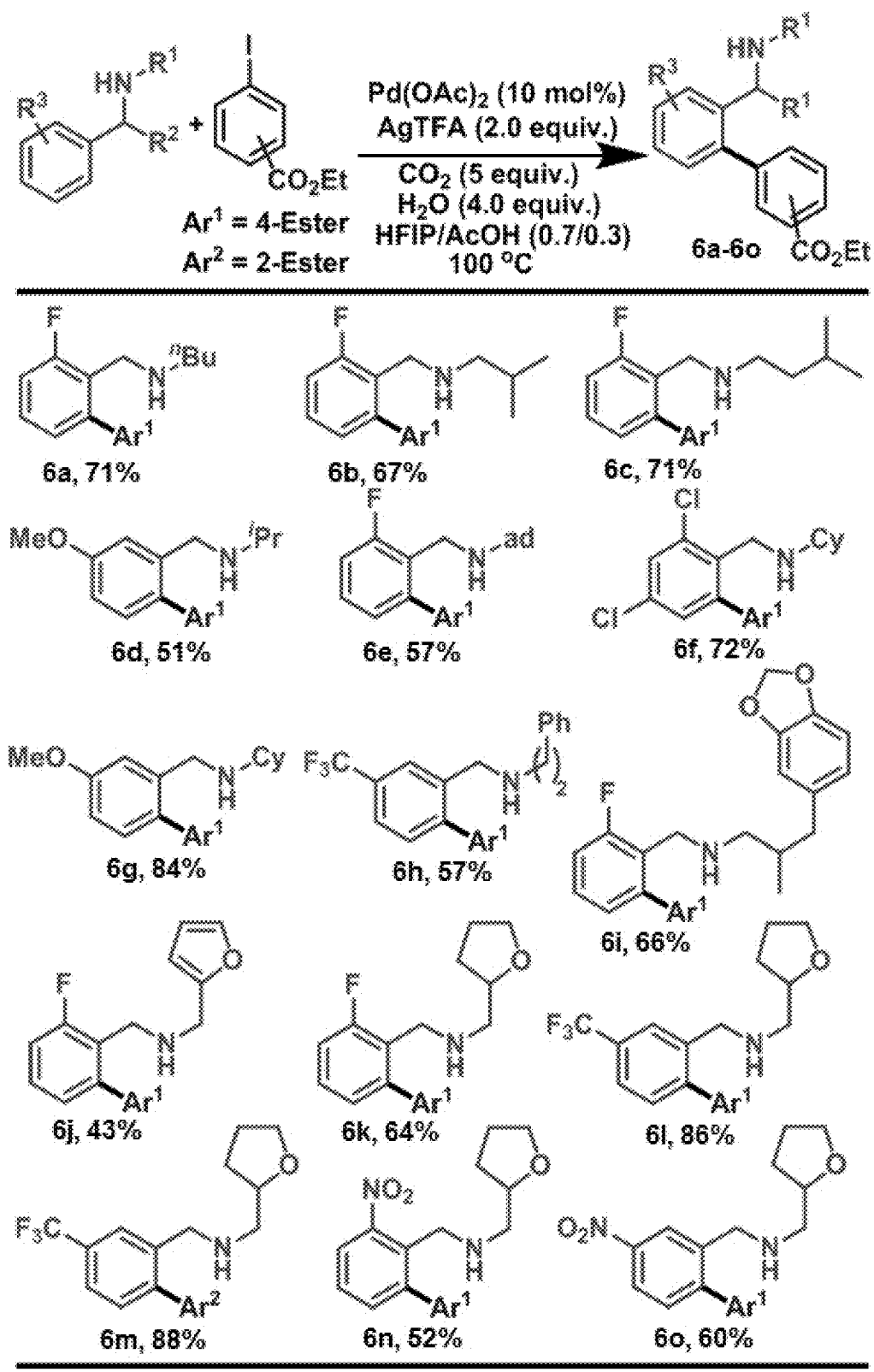
FIG. 25 – Table 6

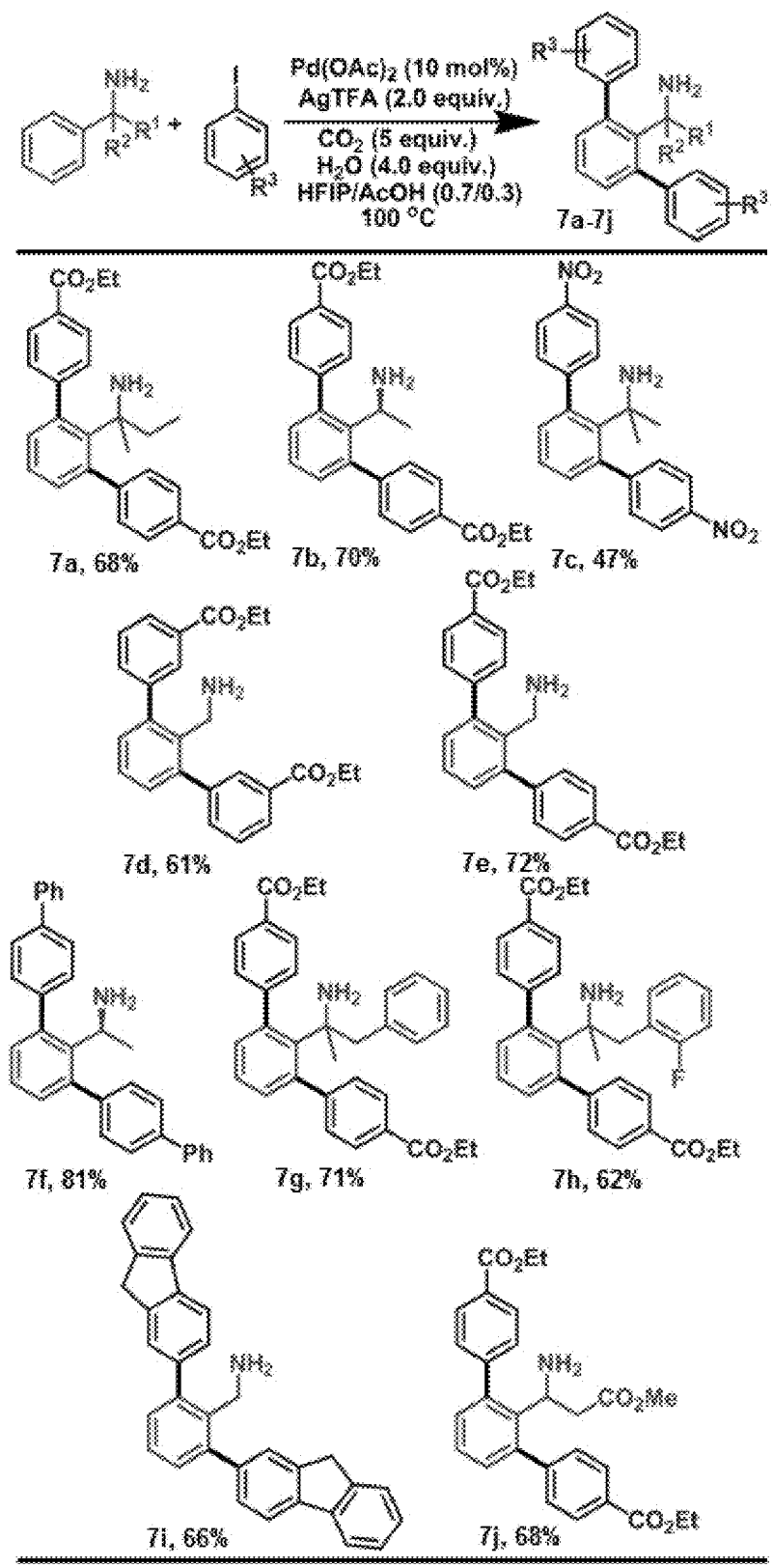
FIG. 26 – Table 7

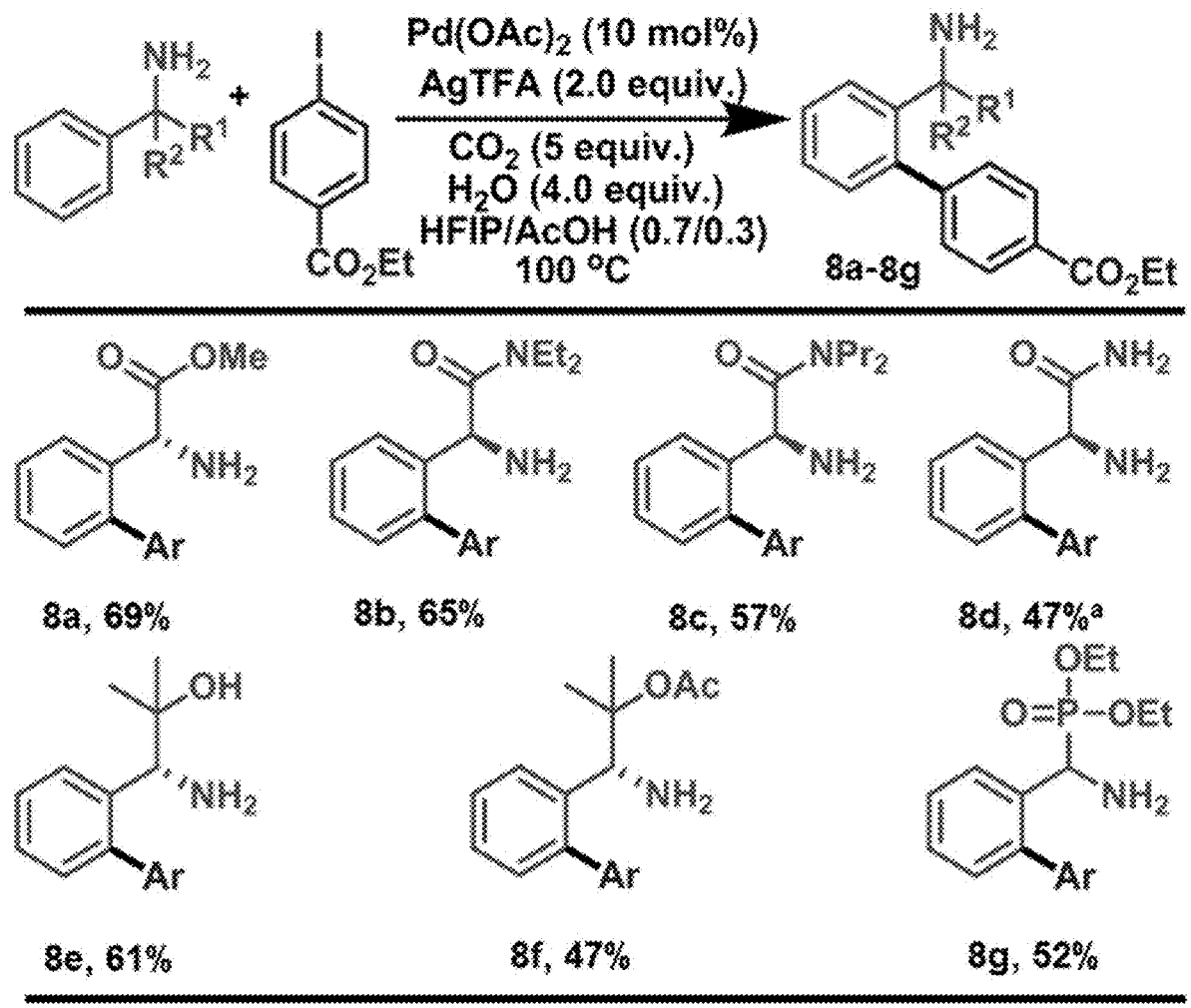
FIG. 27 – Table 8

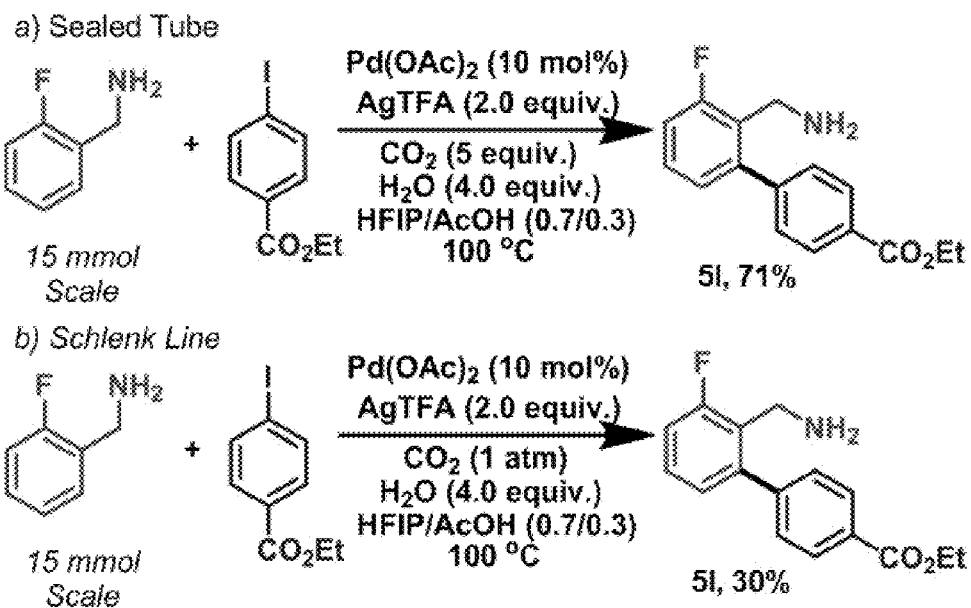
FIG. 28 – Scheme 5
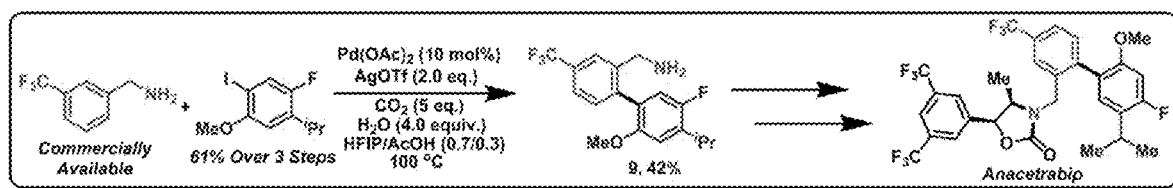
FIG. 29 – Scheme 6

CARBON DIOXIDE AS A DIRECTING GROUP FOR C—H FUNCTIONALIZATION REACTIONS INVOLVING LEWIS BASIC AMINES, ALCOHOLS, THIOLS, AND PHOSPHINES FOR THE SYNTHESIS OF COMPOUNDS

RELATED APPLICATIONS

This application claims priority to U.S. Provisional Application No. 62/608,074, filed under 35 U.S.C. § 111(b) on Dec. 20, 2017, the disclosure of which is incorporated herein by reference in its entirety.

STATEMENT REGARDING FEDERALLY SPONSORED RESEARCH

This invention was made with no government support. The government has no rights in this invention.

BACKGROUND

The use of herbicides has had a transformational role on the productivity of agriculture. Without herbicides and other weed control measures, it is estimated that production of some crops in the United States would be cut in half. However, as humanity's use of herbicides has increased, so too have the risks associated with many of the most effective compounds. The agrochemical community is therefore in need of new herbicides, with new modes of action and fewer environmental and health concerns. As with other areas of synthetic chemistry, C—H functionalization can be an invaluable tool to rapidly access libraries of new compounds for screening herbicidal (as well as fungicidal and insecticidal) activity.

Despite the importance of herbicides to current levels of agricultural production, there is increasing concern about their continued use amid new reports on their negative health effects. Herbicides in common usage are no longer the panacea they once seemed: 2,4-dichlorophenoxyacetic acid and analogues have been shown to be carcinogenic to humans, while atrazine has been implicated as a powerful endocrine disrupter that can lead to complete feminization of many fish, reptiles, and amphibians. Growing resistance by weeds is also a concern: glyphosate, the active ingredient in Roundup®, has begun to become ineffective as a number of species develop different mechanisms of immunity. Without viable herbicide alternatives, and with rising diversion of food stocks to fuels, this may lead to decreased agricultural production, increased food costs, and may lead to eventual food shortages.

The challenge in developing new herbicides is that many compounds must be screened, and there is approximately a $5 \times 10^{-6}$ probability of a compound being a viable candidate. More efficient methods are therefore required to rapidly produce new structurally diverse compounds. Although directed C—H activation can allow for this diversification of simple feedstocks, the need for extra steps for addition and removal of directing groups (DGs) adds both time and cost in the discovery process. Compared with medicinal compounds, new agricultural chemicals must also be synthesized while maintaining a price point that makes them competitive in the marketplace. Additional synthetic steps and poor atom economy mean that the traditional paradigm of adding complex, stoichiometric DGs (PRIOR ART FIG. 1) to substrates will not be applicable to industrial production of new herbicides and pesticides.

Numerous directing groups have been used for the directed C—H functionalization of amines and other heteroatom-bearing substrates. However, these have mostly involved stoichiometric conversion of the amine into an amide (or other robust functional groups for other heteroatom-based substrates), requiring significantly more steps and reduced atom economy as the directing groups must be installed prior to C—H functionalization and typically removed after the reaction, sometimes under harsh conditions. The conversion of the amine into an amide does offer some protection of the amine when more oxidizing conditions are employed. Other approaches have focused on in situ-installed directing groups, primarily through formation of imines, that can be easily removed at the end of the reaction. Although these strategies enjoy increased atom economy, they are less applicable to strongly oxidizing conditions, as imines are considerably less tolerant of oxidants compared to amides, and the presence of free amine can also lead to oxidation of the theroatom group. In addition, the requisite formation of imines requires that these strategies can only be applied to primary amines. Strategies for other heteroatoms are similar in most respects, except that in situ-directing groups are more limited for alcohols and thiols, and practically non-existant for phosphorus-based compounds.

Conventional directing groups typically must be in the product, or require extra synthetic steps to append or remove. Conventional directing groups must also be strong enough to coordinate to the transition metal. Furthermore, high temperatures are usually necessary. Most non-covalent interactions are not practical for C—H activation reactions. Thus, there is a need in the art for synthetic methods involving C—H functionalization that utilize different directing groups.

SUMMARY

Provided is a method of functionalizing a C—H bond, the method comprising using $CO_2$ as a directing group to convert a C—H bond in a substrate compound into a C—C, C—B, C—N, C—O, C—F, C—Cl, C—Br, C—I, C—P, or C—S bond, wherein the substrate compound comprises an amine, alcohol, thiol, or phosphine functional group. In certain embodiments, the C—H bond is in a γ-position relative to the amine, alcohol, thiol, or phosphine functional group.

In certain embodiments, the substrate compound is reacted with a reactant in the presence of $CO_2$ and a transition metal catalyst. In particular embodiments, the transition metal catalyst comprises palladium. In particular embodiments, the reactant comprises an iodoaromatic compound. In particular embodiments, the iodoaromatic compound is selected from the group consisting of: phenyl iodide, 3-iodoisocoumarin (S-23), 5-iodo-1-tosyl-1H-indole (S-24), 1-ethoxy-4-iodobenzene (S-25), and 1-benzyloxy-4-iodobenzene (S-26). In particular embodiments, the reactant comprises a heterocycle.

In certain embodiments, the amine is a primary amine. In particular embodiments, the primary amine is selected from the group consisting of: 1-ethylcyclopentan-1-amine (S-1), 1-ethylcyclohexan-1-amine (S-2), 1-ethylcycloheptan-1-amine (S-3), 4-(tert-butyl)-1-ethylcyclohexan-1-amine (S-4), 9-ethyl-9H-fluoren-9-amine (S-5), 3-methylheptan-3-amine (S-6), 3-methylnon-3-amine (S-7), 3-methylpentan-3-amine (S-8), 3-ethylpentan-3-amine (S-9), and heptan-3-amine (S-10).

In certain embodiments, the amine is a secondary amine. In particular embodiments, the secondary amine is selected from the group consisting of: N-(tert-pentyl)propan-1-amine (S-12), N-(tert-pentyl)butan-1-amine (S-13), N-(tert-pentyl)pentan-1-amine (S-14), 2-methyl-N-phenethylbutan-2-amine (S-15), N-benzyl-2-methylbutan-2-amine (S-16), N-(4-methoxybenzyl)-2-methylbutan-2-amine (S-17), N-(3-methoxybenzyl)-2-methylbutan-2-amine (S-18), N-(4-tolyl)-2-methylbutan-2-amine (S-19), N-(3-tolyl)-2-methylbutan-2-amine (S-20), and N-propylpentan-2-amine (S-22).

In certain embodiments, the amine is a disilanol amine. In particular embodiments, the disilanol amine is 6-ethyl-3,3,9,9-tetraisopropyl-2,10-dimethyl-4,8-dioxa-3,9-disilaundecan-6-amine (S-11).

In certain embodiments, the amine is a tertiary amine.

In certain embodiments, the amine is a benzylamine. In certain embodiments, the amine is an allylamine.

Further provided is a method of synthesizing a compound, the method comprising reacting a substrate having an amine, alcohol, thiol, or phosphine functional group with a reactant in the presence of $CO_2$ and a transition metal catalyst to produce a compound, wherein the substrate is functionalized at a γ-C—H.

In certain embodiments, the compound comprises a γ-arylated primary amine.

In certain embodiments, the compound comprises 2-methyl-4-phenylbutan-2-amine (1a), 4-(3-fluorophenyl)-2-methylbutan-2-amine (1b), 4-(4-fluorophenyl)-2-methylbutan-2-amine (1c), 2-methyl-4-[3-(trifluoromethyl)phenyl]butan-2-amine (1d), 2-methyl-4-[4-(trifluoromethyl)phenyl]butan-2-amine (1e), ethyl 2-(3-amino-3-methylbutyl)benzoate (1f), ethyl 3-(3-amino-3-methylbutyl)benzoate (1g), ethyl 4-(3-amino-3-methylbutyl)benzoate (1h), 2-methyl-4-(3-nitrophenyl)butan-2-amine (1i), 2-methyl-4-(4-nitrophenyl)butan-2-amine (1j), 4-[3,5-bis(trifluoromethyl)phenyl]-2-methylbutan-2-amine (1k), dimethyl 5-(3-amino-3-methylbutyl)isophthalate (1l), 4-(3-chloro-4-fluorophenyl)-2-methylbutan-2-amine (1m), 4-(4-bromophenyl)-2-methylbutan-2-amine (1n), 4-(4-iodophenyl)-2-methylbutan-2-amine (1o), 7-(3-amino-3-methylbutyl)-3,4-diphenyl-1H-isochromen-1-one (1p), 2-methyl-4-(N-tosyl-1H-indol-5-yl)butan-2-amine (1q), 4-(3-methoxyphenyl)-2-methylbutan-2-amine (1r), 4-(4-methoxyphenyl)-2-methylbutan-2-amine (1s), 4-(4-ethoxyphenyl)-2-methylbutan-2-amine (1t), 4-(4-benzyloxyphenyl)-2-methylbutan-2-amine (1u), 2-methyl-4-(m-tolyl)butan-2-amine (1v), 2-methyl-4-(p-tolyl)butan-2-amine (1w), 4-(1,1'-biphenyl-4-yl)-2-methylbutan-2-amine (1x), 2-methyl-4-(naphthalen-1-yl)butan-2-amine (1y), 4-(2-fluorophenyl)-2-methylbutan-2-amine (1z), 2-(3-amino-3-methylbutyl)phenol (1aa), 4-(2-methoxyphenyl)-2-methylbutan-2-amine (1ab), 4,4'-(1,4-phenylene)bis(2-methylbutan-2-amine) (1ac), 1-phenethylcyclopentanamine (2a), 1-phenethylcyclohexanamine (2b), 1-phenethylcycloheptanamine (2c), 4-(tert-butyl)-1-phenethylcyclohexanamine (2d), 9-phenethyl-9H-fluoren-9-amine (2e), 3-methyl-1-phenylheptan-3-amine (2f), 3-methyl-1-phenylnonan-3-amine (2g), 2-amino-2-phenethylpropane-1,3-diol (2h), 3-methyl-1-phenylpentan-3-amine (2i-mono), 3-methyl-1,5-diphenylpentan-3-amine (2i-di), 3-ethyl-1-phenylpentan-3-amine (2j-mono), 3-ethyl-1,5-diphenylpentan-3-amine (2j-di), 4-(1,1'-biphenyl-4-yl)butan-2-amine (2k), 1-(1,1'-biphenyl-4-yl)pentan-3-amine (2l), 1-(1,1'-biphenyl-4-yl)heptan-3-amine (2m), or 4-(1,1'-biphenyl-4-yl)-3,3-dimethylbutan-2-amine (2n).

In certain embodiments, the compound comprises a γ-arylated secondary amine. In particular embodiments, the γ-arylated secondary amine is selected from the group consisting of: 4-(1,1'-biphenyl-4-yl)-2-methyl-N-propylbutan-2-amine (3a), N-[4-(1,1'-biphenyl-4-yl)-2-methylbutan-2-yl]butan-1-amine (3b), N-[4-(1,1'-biphenyl-4-yl)-2-methylbutan-2-yl]pentan-1-amine (3c), 2-methyl-N-phenethyl-4-phenylbutan-2-amine (3d), N-benzyl-2-methyl-4-phenylbutan-2-amine (3e), N-(4-methoxybenzyl)-2-methyl-4-phenylbutan-2-amine (3f), N-(3-methoxybenzyl)-2-methyl-4-phenylbutan-2-amine (3g), 2-methyl-N-(4-methylbenzyl)-4-phenylbutan-2-amine (3h), 2-methyl-N-(3-methylbenzyl)-4-phenylbutan-2-amine (3i), 2-methyl-N-(naphthalen-2-ylmethyl)-4-phenylbutan-2-amine (3j), ethyl 4-(3-(benzylamino)-3-methylbutyl)benzoate (3k), and 1-(1,1'-biphenyl-4-yl)-N-propylpentan-3-amine (3l).

In certain embodiments, the compound comprises Fingolimod, Detrol LA, Sensipar, Duloxetine, a B-3 adrenergic agonist, a SSTR4 agonist, Kasugamycin, Strychnine, or a derivative thereof.

Further provided is a compound made by the method described herein.

Further provided is a kit for making a compound, the kit comprising a first container housing a supply of $CO_2$, and a second container housing a transition metal catalyst. In certain embodiments, the kit further comprises a substrate compound having an amine, alcohol, thiol, or phosphine functional group.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

PRIOR ART FIG. 1: Conventional directing groups for C—H functionalization.

FIG. 2: Approaches to C—H functionalization of sterically unhindered amines.

FIG. 7: Procedure for optimizing γ-arylated 2° amines (top) and table showing results of optimization of γ-arylated 2° amines (bottom).

FIG. 14: Illustrations showing the reversibility of carbon dioxide adduct formation during the reaction, the reversibility of C—H activation, evidence for a directing rather than deactivation effect, and the ability to scale up or use atmospheric pressure.

FIG. 20: Arylation of benzylamines.

FIG. 23: Table 4, showing aryl iodide scope of the γ-$C(sp^2)$-H arylation of 2-(2-fluorophenyl)butan-2-amine.

FIG. 24: Table 5, showing primary benzylamine scope of the γ-$C(sp^2)$-H arylation with aryl halides.

FIG. 25: Table 6, showing secondary benzylamine scope of the γ-$C(sp^2)$-H arylation with aryl halides.

FIG. 26: Table 7, showing the scope of the di-γ-$C(sp^2)$-H arylation of sterically-accessible benzylamines.

FIG. 27: Table 8, showing the scope of the selective mono-γ-$C(sp^2)$-H arylation of sterically-accessible benzylamines. $^a$HFIP used as solvent.

FIG. 28: Scheme 5, showing scale-up experiments.

FIG. 29: Scheme 6, showing total synthesis of rac-Anacetrapib via γ-$C(sp^2)$-H arylation of a benzylamine precursor.

FIG. 30A shows substoichiometric $CO_2$ loading. FIG. 30B shows a deuterated solvent study. FIG. 30C shows the kinetic isotope effect. FIG. 30D shows stoichiometric cyclopalladation. FIG. 30E shows rate dependency on [$CO_2$].

DETAILED DESCRIPTION

Figure 3A:
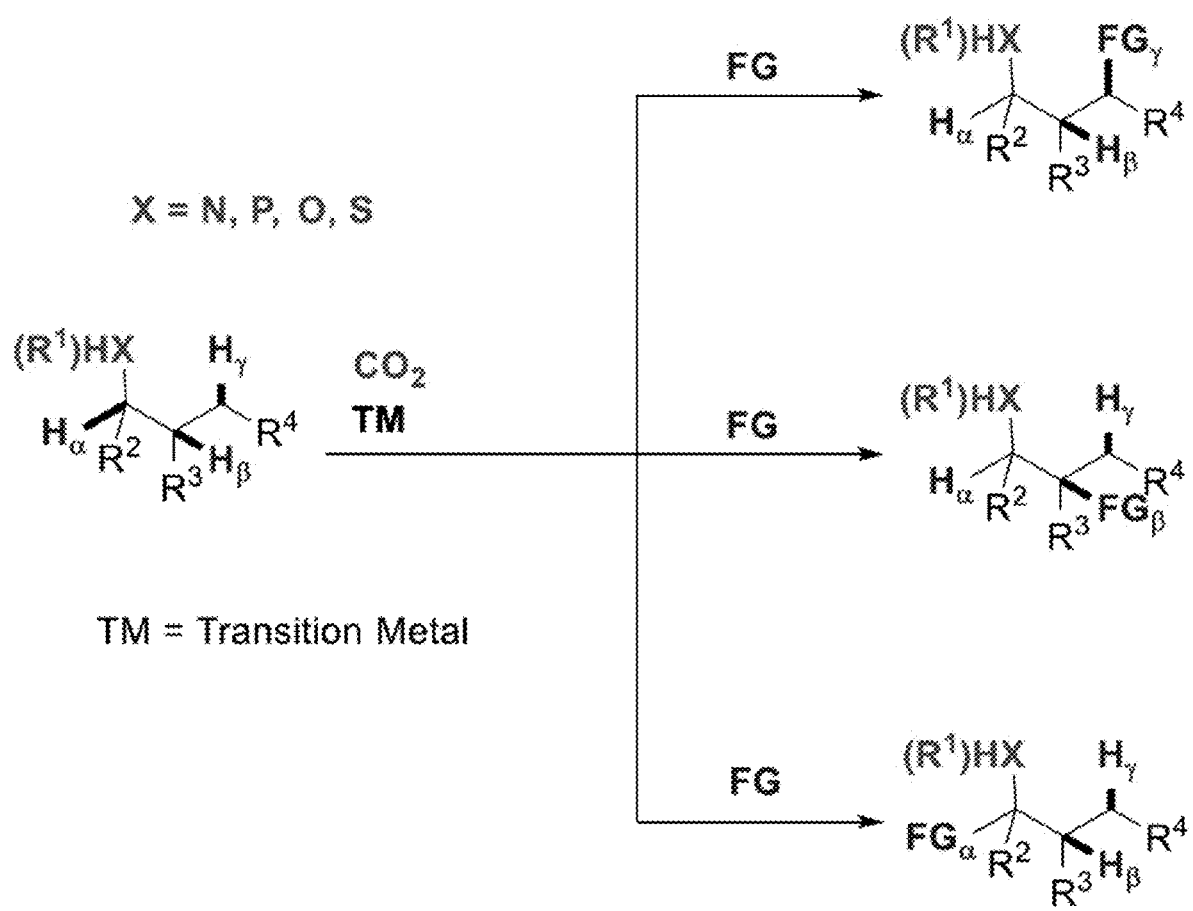
FIG. 3A: Scheme 1, depicting a general process for directed C—H functionalization based on Lewis Basic substrates. FG=Functional Group. TM=Transition Metal.
Figure 3B:
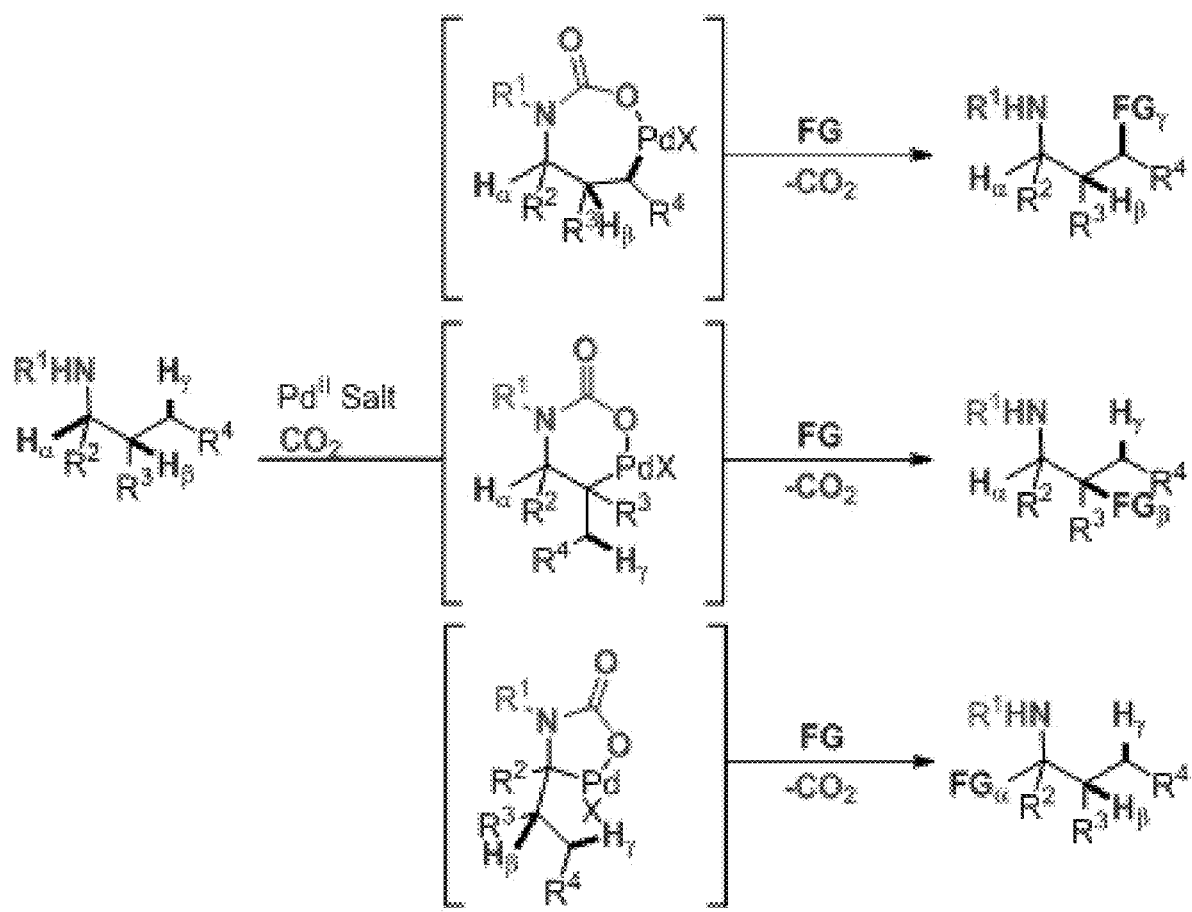
FIG. 3B: Scheme 1, where X=N and the TM is Pd, depicted with intermediates.
Figure 3C:
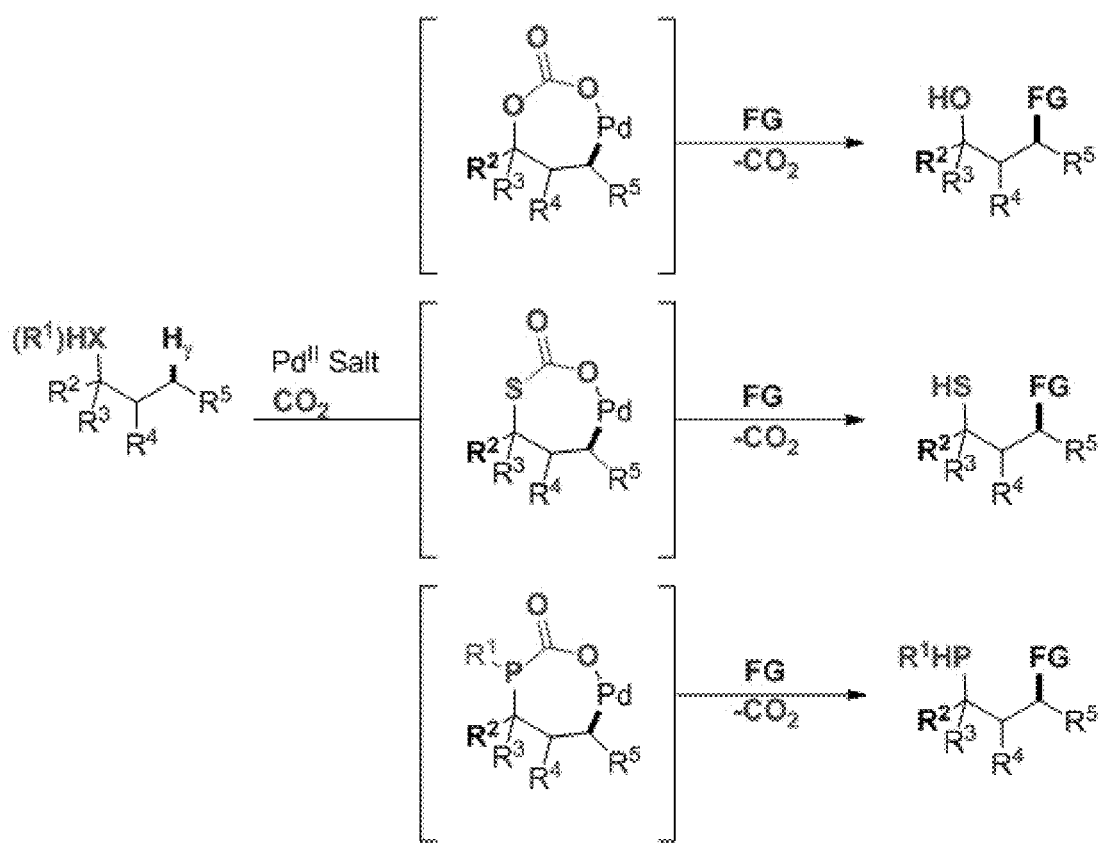
FIG. 3C: Scheme 1, depicted with intermediates, where the substrate includes an alcohol, thiol, or phosphine.

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

Provided is a method which uses carbon dioxide as an in situ directing group for the transition metal-catalyzed C—H functionalization of organic compounds. In some aspects, the method is a hybrid of two general strategies: (1) in-situ directing group formation, and (2) preformation of a robust directing group. The transition metal-catalyzed functionalization can be used to convert a specific C—H bond into a new C—C, C—B, C—N, C—O, C—F, C—Cl, C—Br, C—I, C—P, or C—S bond, and the free heteroatom-based products are easily purified from the carbon dioxide directing group. The method facilitates rapid access to new C—H functionalized C—C, C—B, C—N, C—O, C—F, C—Cl, C—Br, C—I, C—P, or C—S bonds on various aliphatic and aromatic structures bearing amine, alcohol, thiol, or phosphine groups that can be used to bind $CO_2$ as a directing group.

The development of new strategies for elaboration of amines via C—H functionalization has been an important area of research over the last decade. To improve the sustainability and effectiveness of C—H activation, a strategy using carbon dioxide as a hybrid directing group that combines the benefits of transient directing groups with traditional amide directing groups is demonstrated herein. This methodology has been used to enable a simple one-pot procedure whereby 1° and 2° aliphatic amines can be arylated selectively at their γ-C—H position. The examples herein show the method to be applicable to a wide array of aryl and heteroaryl iodides as well as many sterically accessible 1° and 2° amines with selectivity for γ-$C(sp^3)$-H functionalization of terminal $CH_3$ groups. The examples herein also show the method to be useful for $C(sp^2)$-H arylation of primary and secondary benzylamines. The method is also useful for other $C(sp^3)$-H functionalization, as well as allylamine $C(sp^2)$-H functionalization.

The use of transition metal-catalyzed C—H activation has revolutionized the installation of C—C, C—N, C—O, C—B, and C—X bonds at otherwise inert C—H bonds, and is transforming the way chemists approach synthesis. The majority of these transformations is achieved with the use of monoanionic or strongly chelating directing groups that bind to the transition metal catalyst, conferring site selectivity in C—H activation. Amines are typically considered weak donors, and, as a result, free amines, especially those bearing N—H bonds, are generally limited to serving as directing groups for the C—H activation of more reactive $C(sp^2)$-H bonds only. To achieve $C(sp^3)$-H bond activation of amines, one typically must either use exceedingly sterically-hindered free amines, or convert the amine into either an amide or imine directing group (FIG. 2). Converting amines into amides stabilizes the nitrogen, preventing undesirable side reactions such as oxidation. The downside is that this conventional strategy also requires additional synthetic steps to append and remove the stoichiometric directing group, which increases time and decreases atom economy. In contrast, imine-type directing groups can often be prepared and removed under milder conditions in situ. This has led to one-pot procedures for installation, functionalization, and removal of the directing group, and has even been extended to catalytic application of the directing group. The shortfall of an imine directing group strategy is that, unlike with amides, both the imine and any free amine that are present can be readily oxidized, limiting the types of transformations that can be achieved.

To circumvent the challenges of these two strategies, a hybrid directing group strategy was developed. A directing group should act like an amide, forming a robust, electron poor amine that resists oxidation, while still benefitting from the facile removal and installation of imine-type directing groups and contributing to the step and atom economy necessary to make this chemistry more industrially-relevant.

Figure 4:
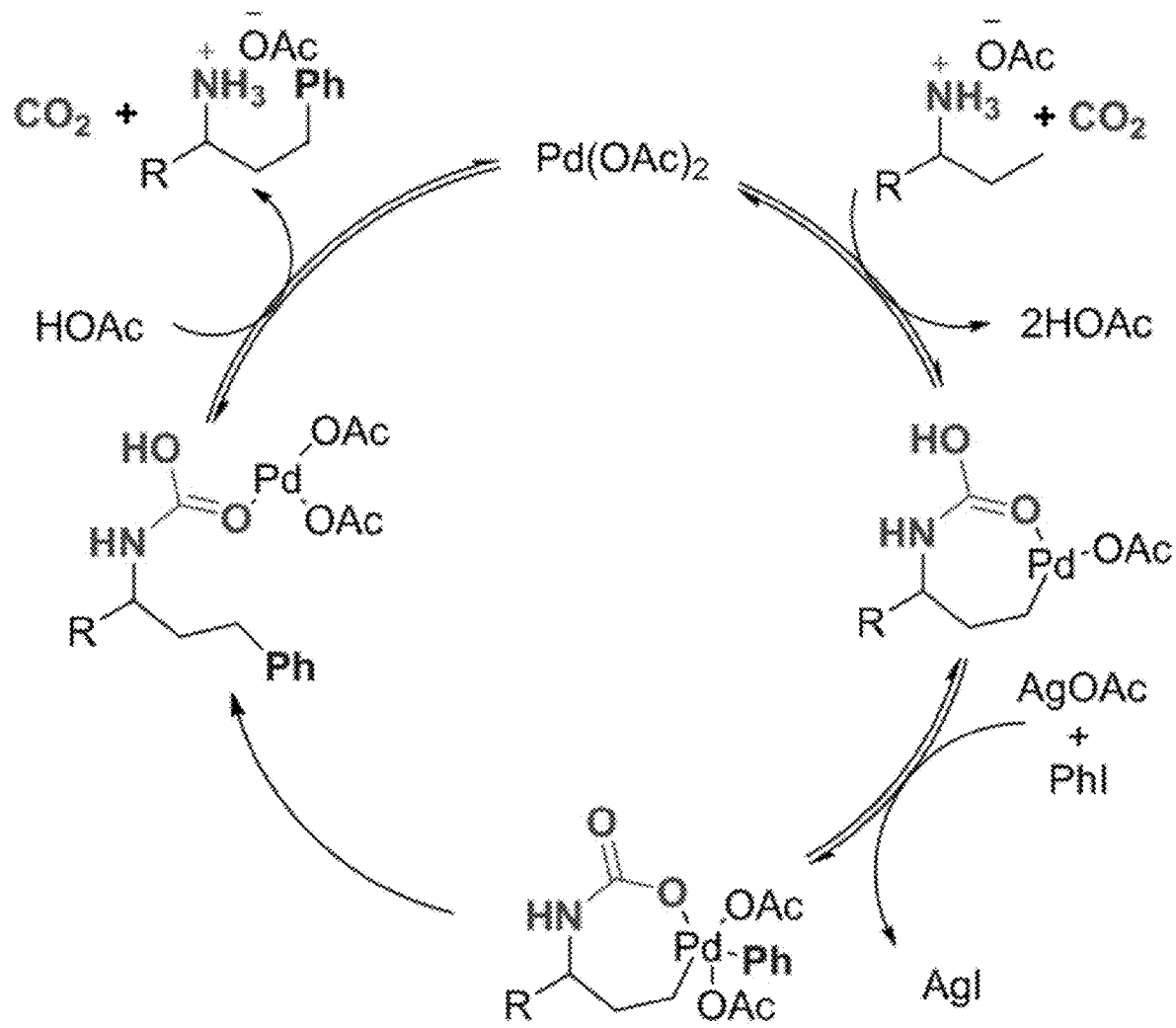
FIG. 4: Mechanism for reactions described herein.

Carbon dioxide ($CO_2$) is a molecule that fit this description: it contains a carbonyl that can reversibly react with amines, while the carbamate products can function to bind to a transition metal catalyst (FIG. 2). Carbon dioxide has previously been used as a traceless directing group in the C—H activation of benzoic acids, followed by decarboxylation. Although the transformation required relatively high heat (190° C.) and high pressure (25 atm $CO_2$) to form the benzoic acid intermediate, the carboxylic acid could be installed in situ, used for C—H activation, and removed in one pot. In accordance with the present disclosure, use of a more nucleophilic amine to enable a one-pot carboxylation, C—H activation, decarboxylation sequence can be realized under considerably milder conditions. Thus, provided herein is a platform for carbon dioxide-directed C—H functionalization that allows facile access to structurally diverse compounds while simultaneously being viable for production scale of newly identified hits (Scheme 1, FIG. 3A). This platform uses the ability of Lewis basic atoms to form carboxylate adducts with carbon dioxide (FIG. 4) to achieve site-selective C—H functionalization for a broad range of pre-existing functionality without the need of costly directing groups, and allowing rapid elaboration from easily accessible feedstocks.

To make C—H functionalization viable for the task of rapidly assembling new herbicides and the like, the need for time, component, and labor-intensive directing groups has to be assuaged. Carbon dioxide can be used as a cheap, readily available alternative directing group for the C—H functionalization of the broad class of Lewis basic substrates. As a by-product of other industrial processes, carbon dioxide is essentially a freely available directing group. The $CO_2$ used in the method may be recycled from any process which gives off $CO_2$.

The transition metal-catalyzed C—H functionalization of simple feedstocks using $CO_2$ as a directing group allows for rapid synthesis of a wide variety of compounds for screening of herbicidal and pesticidal activity. As well as being important for advancing the synthesis of novel herbicides, the C—H activation approach described herein can also be used in the pharmaceutical and other fine chemical industries.

In accordance with the present disclosure, carbon dioxide is a general, green directing group for a variety of transition metal-mediated reactions. It is cheaper and more readily available than traditional directing groups, even if it is used stoichiometrically or super stoichiometrically. By forming a negatively charged carbamate, similar reactivity can be observed with a variety of Lewis basic substrates, obviating the need for extensive reoptimization when the substrate is changed. As a gas, carbon dioxide also has the ability to be more easily recycled than solid or liquid directing groups.

Selective C—H functionalization of Lewis base-$CO_2$ adducts is possible in many transformations, including arylation, amination, and oxidation. Once heteroatom-$CO_2$ adducts are formed, their general selectivity for directed C—H functionalization can be controlled based on a number of steric and electronic factors, and is consistent regardless of the heteroatom used. By understanding the selectivity of these transformations, numerous new products can be generated from simple feedstocks, and these may either be directly screened for their activity as herbicides, or incorporated into other structures (such as the triazine class of herbicides) and evaluated.

C—H activation is driven by sterics. For example, a $CH_3$ is easier to break than a $CH_2$, and so on. Also, C—H bonds that are furthest away from the functional group reacting with $CO_2$ are easier to break than C—H bonds that are closer. Carbon dioxide can react with primary, secondary, and even tertiary amines. Surprisingly, the method herein works with secondary amines, unlike previous methods. A method for functionalizing C—H bonds in secondary amines has been lacking in the art.

Without wishing to be bound by theory, the mechanism (FIG. 4) is believed to include a 7-membered metallocycle, which seems unstable and is therefore uniquely situated for γ C—H bonds instead of β C—H bonds or a C—H bonds. The heteroatom-$CO_2$ adducts that form as intermediates (FIG. 4) protect the sensitive functional groups from oxidation and side reactions. Furthermore, X—$CO_2$ adducts are more electronically similar, decreasing the need for reoptimization when using different substrates and reactants with different functional groups.

The reactions can be performed in any suitable solvent. Some non-limiting examples of suitable solvents include acetic acid, AcOH, hexafluoroisopropanol (HFIP), acetonitrile, trifluoroacetic acid (TFA), and combinations thereof. The carbamates are not very stable in acetic acid. As a result, when the reaction vials are opened, the carbamates bubble off. Furthermore, an acid workup isolates the products well. As seen in the examples herein, the carbamates practically do not show up on NMR analysis of the products.

A wide variety of transition metal catalysts can be utilized. Some non-limiting examples of suitable transition metal catalyst include $Pd(OAc)_2$, $Pd(TFA)_2$, $PdCl_2$, and $Pd(trimethylacetate)_2$. However, other transition metal catalyst are encompassed within the scope of the present disclosure.

Figure 5:
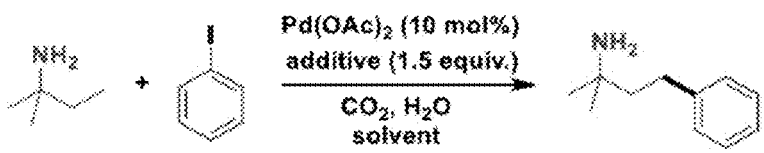
FIG. 5: Procedure for optimizing γ-arylation of 10 amines (top) and table showing results of optimization of γ-arylated 1° amines (bottom).
Figure 6:
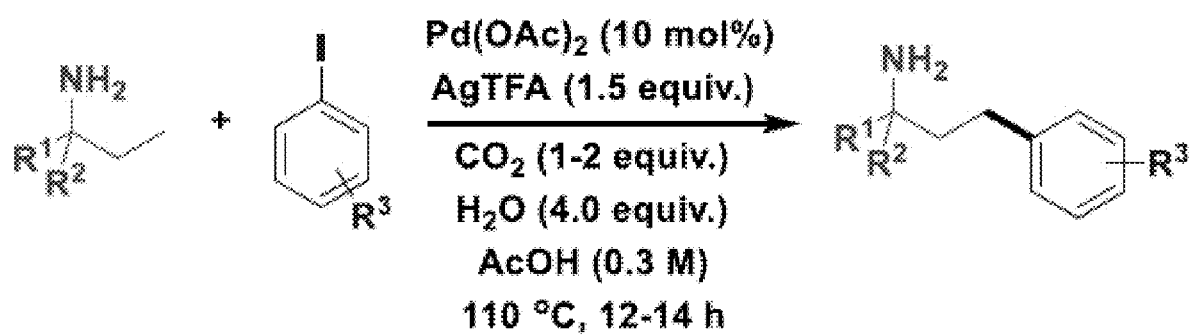
FIG. 6: Procedure used for evaluating substrate scope.

The functional group to be added to the substrate through functionalization of the γ C—H bond can be from a reactant having the desired functional group (i.e., the functional group desired to replace the H in the γ C—H of the substrate) bonded to a halogen or other species which forms a good leaving group. Thus, for example, the γ-arylation of amines can be conducted by reacting an amine with an iodoaromatic compound in the presence of $CO_2$ and a transition metal catalyst. (FIGS. 5-7.) $CO_2$ may be used as a traceless directing group for γ-C—H arylation of aliphatic amine substrates.

Suitable amines for γ C—H functionalization according to the present disclosure include, but are not limited to, primary amines, such as 1-ethylcyclopentan-1-amine (S-1), 1-ethylcyclohexan-1-amine (S-2), 1-ethylcycloheptan-1-amine (S-3), 4-(tert-butyl)-1-ethylcyclohexan-1-amine (S-4), 9-ethyl-9H-fluoren-9-amine (S-5), 3-methylheptan-3-amine (S-6), 3-methylnon-3-amine (S-7), 3-methylpentan-3-amine (S-8), 3-ethylpentan-3-amine (S-9), or heptan-3-amine (S-10); secondary amines, such as N-(tert-pentyl)propan-1-amine (S-12), N-(tert-pentyl)butan-1-amine (S-13), N-(tert-pentyl)pentan-1-amine (S-14), 2-methyl-N-phenethylbutan-2-amine (S-15), N-benzyl-2-methylbutan-2-amine (S-16), N-(4-methoxybenzyl)-2-methylbutan-2-amine (S-17), N-(3-methoxybenzyl)-2-methylbutan-2-amine (S-18), N-(4-tolyl)-2-methylbutan-2-amine (S-19), N-(3-tolyl)-2-methylbutan-2-amine (S-20), or N-propylpentan-2-amine (S-22); tertiary amines; or disilanol amines, such as 6-ethyl-3,3,9,9-tetraisopropyl-2,10-dimethyl-4,8-dioxa-3,9-disilaundecan-6-amine (S-11).

Non-limiting example iodoaromatics for use in the γ-arylation of amines include phenyl iodide, 3-iodoisocoumarin (S-23), 5-iodo-1-tosyl-1H-indole (S-24), 1-ethoxy-4-iodobenzene (S-25), and 1-benzyloxy-4-iodobenzene (S-26). Such non-limiting example reactions may produce γ-arylated amines, including γ-arylated secondary amines. Non-limiting example γ-arylated amines that can be prepared by this method include 2-methyl-4-phenylbutan-2-amine (1a), 4-(3-fluorophenyl)-2-methylbutan-2-amine (1b), 4-(4-fluorophenyl)-2-methylbutan-2-amine (1c), 2-methyl-4-[3-(trifluoromethyl)phenyl]butan-2-amine (1d), 2-methyl-4-[4-(trifluoromethyl)phenyl]butan-2-amine (1e), ethyl 2-(3-amino-3-methylbutyl)benzoate (1f), ethyl 3-(3-amino-3-methylbutyl)benzoate (1g), ethyl 4-(3-amino-3-methylbutyl)benzoate (1h), 2-methyl-4-(3-nitrophenyl)butan-2-amine (1i), 2-methyl-4-(4-nitrophenyl)butan-2-amine (1j), 4-[3,5-bis(trifluoromethyl)phenyl]-2-methylbutan-2-amine (1k), dimethyl 5-(3-amino-3-methylbutyl)isophthalate (1l), 4-(3-chloro-4-fluorophenyl)-2-methylbutan-2-amine (1m), 4-(4-bromophenyl)-2-methylbutan-2-amine (1n), 4-(4-iodophenyl)-2-methylbutan-2-amine (1o), 7-(3-amino-3-methylbutyl)-3,4-diphenyl-1H-isochromen-1-one (1p), 2-methyl-4-(N-tosyl-1H-indol-5-yl)butan-2-amine (1q), 4-(3-methoxyphenyl)-2-methylbutan-2-amine (1r), 4-(4-methoxyphenyl)-2-methylbutan-2-amine (1s), 4-(4-ethoxyphenyl)-2-methylbutan-2-amine (1t), 4-(4-benzyloxyphenyl)-2-methylbutan-2-amine (1u), 2-methyl-4-(m-tolyl)butan-2-amine (1v), 2-methyl-4-(p-tolyl)butan-2-amine (1w), 4-(1,1'-biphenyl-4-yl)-2-methylbutan-2-amine (1x), 2-methyl-4-(naphthalen-1-yl)butan-2-amine (1y), 4-(2-fluorophenyl)-2-methylbutan-2-amine (1z), 2-(3-amino-3-methylbutyl)phenol (1aa), 4-(2-methoxyphenyl)-2-methylbutan-2-amine (1ab), 4,4'-(1,4-phenylene)bis(2-methylbutan-2-amine) (1ac), 1-phenethylcyclopentanamine (2a), 1-phenethylcyclohexanamine (2b), 1-phenethylcycloheptanamine (2c), 4-(tert-butyl)-1-phenethylcyclohexanamine (2d), 9-phenethyl-9H-fluoren-9-amine (2e), 3-methyl-1-phenylheptan-3-amine (2f), 3-methyl-1-phenylnonan-3-amine (2g), 2-amino-2-phenethylpropane-1,3-diol (2h), 3-methyl-1-phenylpentan-3-amine (2i-mono), 3-methyl-1,5-diphenylpentan-3-amine (2i-di), 3-ethyl-1-phenylpentan-3-amine (2j-mono), 3-ethyl-1,5-diphenylpentan-3-amine (2j-di), 4-(1,1'-biphenyl-4-yl)butan-2-amine (2k), 1-(1,1'-biphenyl-4-yl)pentan-3-amine (2l), 1-(1,1'-biphenyl-4-yl)heptan-3-amine (2m), or 4-(1,1'-biphenyl-4-yl)-3,3-dimethylbutan-2-amine (2n), 4-(1,1'-biphenyl-4-yl)-2-methyl-N-propylbutan-2-amine (3a), N-[4-(1,1'-biphenyl-4-yl)-2-methylbutan-2-yl]butan-1-amine (3b), N-[4-(1,1'-biphenyl-4-yl)-2-methylbutan-2-yl]pentan-1-amine (3c), 2-methyl-N-phenethyl-4-phenylbutan-2-amine (3d), N-benzyl-2-methyl-4-phenylbutan-2-amine (3e), N-(4-methoxybenzyl)-2-methyl-4-phenylbutan-2-amine (3f), N-(3-methoxybenzyl)-2-methyl-4-phenylbutan-2-amine (3g), 2-methyl-N-(4-methylbenzyl)-4-phenylbutan-2-amine (3h), 2-methyl-N-(3-methylbenzyl)-4-phenylbutan-2-amine (3i), 2-methyl-N-(naphthalen-2-ylmethyl)-4-phenylbutan-2-amine (3j), ethyl 4-(3-(benzylamino)-3-methylbutyl)benzoate (3k), and 1-(1,1'-biphenyl-4-yl)-N-propylpentan-3-amine (3l). The skilled practitioner will recognize that the production of γ-arylated amines is merely one class of examples of the broad method described herein.

The presence of some functional groups, such as indols, may require basic conditions for optimal results. Furthermore, substrates bearing heterocycles work except when there's a functional group that can coordinate to the metal, like a pyridine, in them. However, in such cases, the functional group can be protected to prevent coordination to the metal, or a more potent electrophile (as compared to an aryl iodide) such as a diaryl iodonium reagent may be used.

By utilizing carbon dioxide as a relatively low molecular weight, cheap, and readily available in situ directing group, the benefits of amide-type directing groups and the in situ prepared imine-type directing groups can both be realized. Carbon dioxide can be readily reacted to give amide-type directing groups directly in the reaction mixture, similar to the advantage of the imine-type directing groups. In addition, carbon dioxide can be used on primary amines, but unlike imine-type directing groups, carbon dioxide can readily be used as a directing group on secondary and even tertiary amines. In addition, this method can be applied to other heteroatoms, including alcohols, thiols, and phosphines, which is a distinct break from the currently existing directing group strategies which generally only work for one specific type of functional group.

Advantageously, $CO_2$ is a sustainable choice for directed C—H activation that can overcome the challenges of conventional preformed directing groups (easily added/removed, cheap, recyclable) as well as in-situ prepared directing groups (less easily oxidized, stoichiometric or superstoichiometric use is not prohibitively expensive or atom uneconomical). Carbon dioxide can be added and removed in one pot, making this method faster than known methods and requiring fewer steps than known methods. On production scale, the $CO_2$ can be introduced as a gas and removed as a gas simply by pulling a vacuum, obviating the need for a more complex purification to remove. This can fundamentally improve the C—H activation processes across the chemical industry. Furthermore, the method can functionalize $sp^2$ C—H bonds as well as $sp^3$ C—H bonds. For $sp^2$ functionalization, known methods use a vinyl iodide instead of an aryl iodide.

To conduct the reactions, the $CO_2$ may be present, for example, in the headspace of a sealed reaction vial containing the substrate and reactant in a solvent. In a non-limiting example, a reaction in accordance with the present disclosure is conducted in a 90 mL vial with 50 mL solvent and 40 mL headspace. Other methods of conducting the reactions are encompassed within the present disclosure. For better yields, the $CO_2$ should be used stoichiometrically. The $CO_2$ may be used non-stoichiometrically, such as by pre-making the carbamate, however, it is understood that such methods may not provide optimal yields. For instance, using less $CO_2$ than the stoichiometric amount can cause some oxidation products such as imines.

Figure 8:
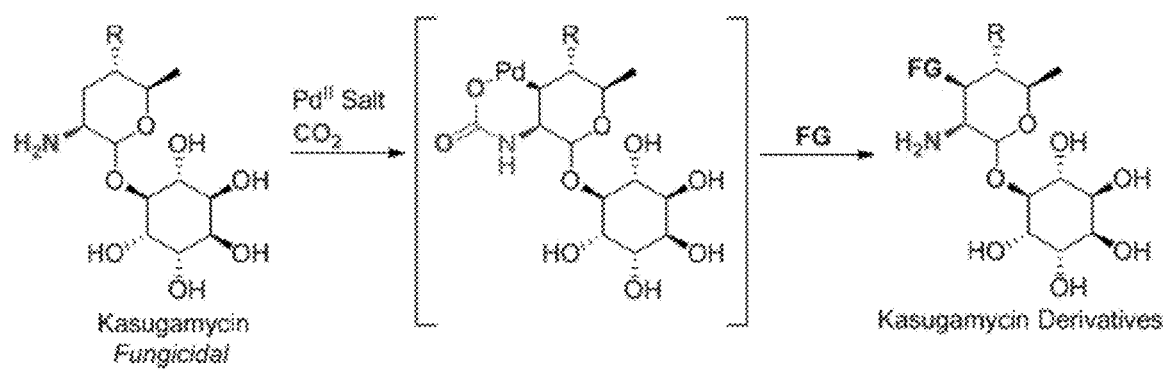
FIG. 8: Scheme 2, depicting the synthesis of Kasugamycin derivatives from Kasugamycin using $CO_2$ as a directing group.
Figure 9:
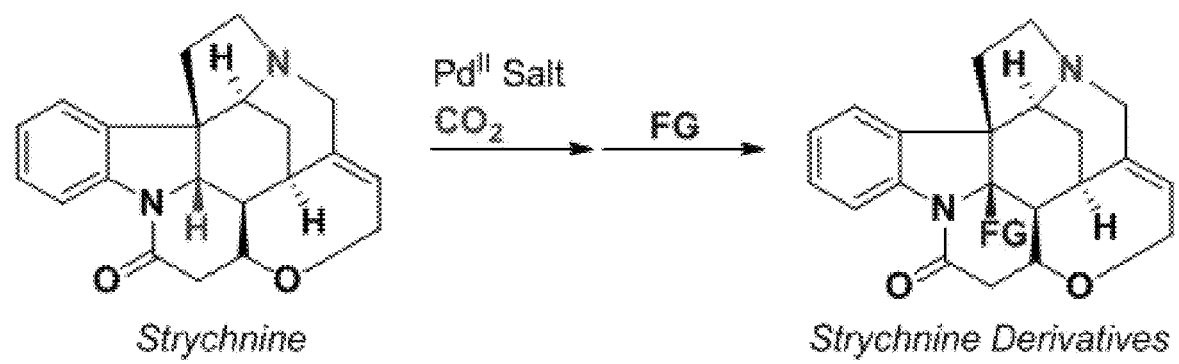
FIG. 9: Scheme 3, depicting the synthesis of Strychnine derivatives from Strychnine using $CO_2$ as a directing group.
Figure 10:
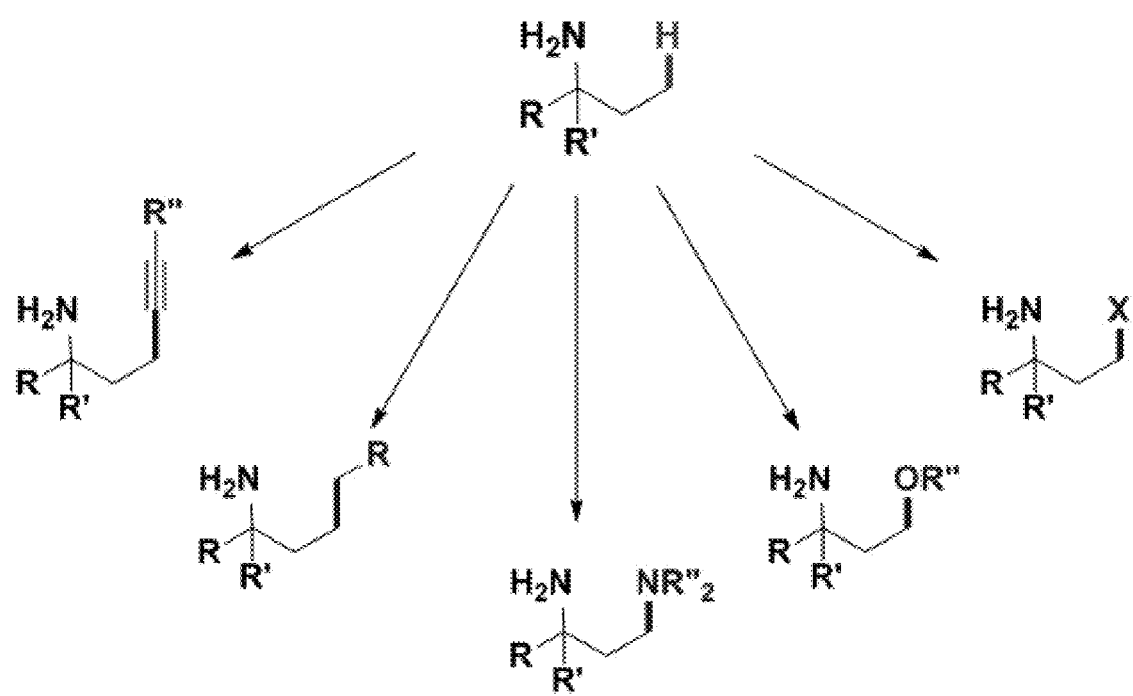
FIG. 10: Scheme 4, depicting the synthesis of possible derivatives.

The compounds made by the method described herein are useful in a variety of industries, including the agrochemical and pharmaceutical industries. For example, a number of FDA approved drugs may be made by the method described herein. Non-limiting examples of such drugs are Fingolimod and related compounds, such as those disclosed in U.S. Pat. No. 5,604,229 or 9,056,813 B2; KRP 203; gamma-aryl amines such as Detrol LA, Sensipar, and Duloxetine; B-3 adrenergic agonists, such as those disclosed in EP Patent 0921120 A1; and SSTR4 agonists, such as those disclosed in WO 2014/184275 A1. As additional non-limiting examples, FIG. 8 depicts the synthesis of Kasugamycin derivatives from Kasugamycin using $CO_2$ as a directing group, and FIG. 9 depicts the synthesis of Strychnine derivatives from Strychnine using $CO_2$ as a directing group. FIG. 10 depicts the synthesis of various other types of compounds, such as alkynes, alkanes, tertiary amines, ethers, and halides. The skilled practitioner will recognize that the breadth of the presently described method is significant.

It is further envisioned that the method described herein can be embodied in the form of a kit or kits. A non-limiting example of such a kit is a kit for making a compound, the kit comprising a supply of $CO_2$ and a transition metal catalyst in separate containers, where the containers may or may not be present in a combined configuration. Many other kits are possible, such as kits that further comprise a substrate compound having an amine, alcohol, thiol, or phosphone functional group. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

Example I—Carbon Dioxide Mediated C(Sp$^3$)-H Arylation of Aliphatic Amines

Initial evaluations of the use of carbon dioxide as a hybrid directing group for amines focused on performing transient directing group-mediated γ-C(sp$^3$)-H arylation. Optimization studies identified that tert-amyl amine could be arylated selectively at the γ-C(sp$^3$)-H position to generate the corresponding arylated primary amine 1a (Table 1, FIG. 11) using phenyl iodide as the aryl source, silver trifluoroacetate as an additive, and approximately one to two equivalents of carbon dioxide as the directing group. Control reactions found that all of the components were critical for significant yields during the reaction. To make the transformation as operationally simple as possible, carbon dioxide was added in the form of dry ice, allowing facile set-up in a standard reaction vial. At the end of the reaction the $CO_2$ is simply bubbled off by addition of aqueous HCl. Of note is that no additional ligands are required to facilitate the reaction.

The scope of this transformation is relatively broad. Arenes bearing non-polar fluorides (1b and 1c) as well as trifluormethyl groups (1d and 1e) can be easily installed. Esters (1f-1h) are also viable substrates. Although ortho-substituted iodides are often poor substrates for C—H arylation, the ortho-ester is tolerated in this reaction, most likely because of chelation-assisted oxidative addition to the C—I bond. Nitro groups (1i and 1j) are amenable to the reaction, as are highly deactivated bis(trifluoromethyl)s (1k) and diesters (1l). Other halides are permissible, including chlorides (1m) and bromides (1n), and the reaction can be performed once selectively on a diiodide (1o), while excess amine can be used to give access to the bis-C—H activated product. Even heterocycles can participate in the reaction, albeit giving the products isocoumarin (1p) and indole (1q) in slightly reduced yields. In terms of electron rich groups, methoxy (1r and 1s), ethoxy (1t), benzyloxy (1u), and methyl groups (1v and 1w) are well tolerated. Conjugated groups such as a para-phenyl or a naphthyl group (1x and 1y) are also tolerated. Although most ortho substituents were not reactive using the initially optimized conditions, by switching from silver trifluoroacetate to silver trifluoromethanesulfonate, even ortho fluoro, hydroxyl, and methoxy groups are tolerated (1z-1ab).

Figure 12:
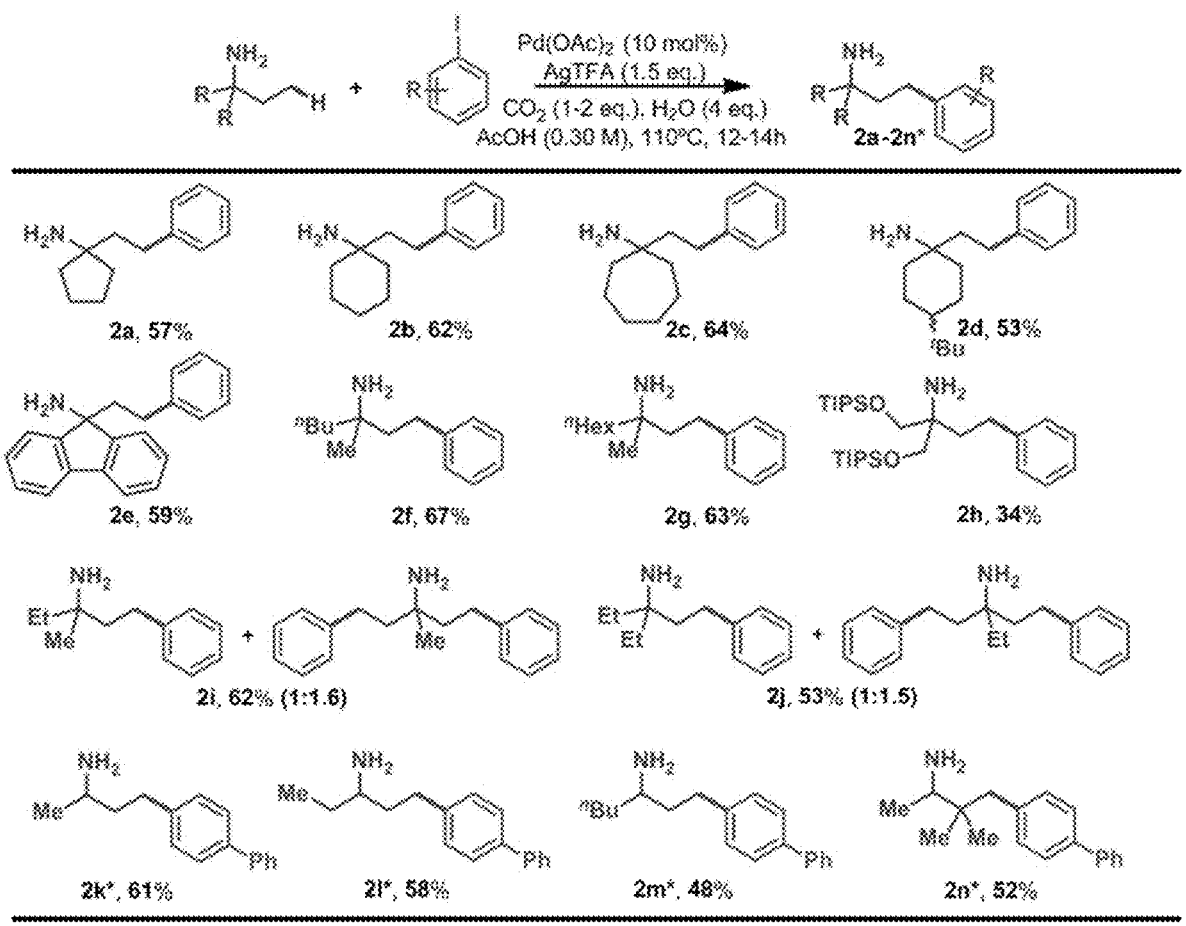
FIG. 12: Table 2, showing the reaction scope of primary amines for $CO_2$-directed γ-C—H arylation. *Reaction performed at 90° C.

Numerous primary amines can also be utilized in the reaction (Table 2, FIG. 12). A variety of cyclic primary amines containing 5, 6, and 7-membered rings are all well tolerated (2a-2c), as well as a tert-butyl-substituted cyclohexyl ring (2d). Despite being dibenzylic, a fluorenone-derived amine showed excellent selectivity for γ-C(sp$^3$)-H rather than γ-C(sp$^2$)-H arylation (2e). Longer alkyl chains were tolerated (2f and 2g), as well as a more lipophilic TIPS-protected diol (2h). Substrates bearing more than one γ-C(sp$^3$)-H site predictably gave a mixture of mono and diarylation products (2i and 2j), although it is worth noting that no triarylation product was observed in the case of 2j. Gratifyingly, the methodology could also be applied to less-substituted primary amines, specifically those bearing a secondary rather than tertiary a-carbon, simply by reducing the reaction temperature. Under these conditions sec-butyl amine was readily arylated (2k). Despite the presence of two equivalent γ-C—H positions, at the lower temperature employed only monoarylation was observed for 3-aminopentane (2l). Using a longer chain did not appreciably decrease the yield (2m), and at the reduced temperature even a tert-butyl group could be selectively arylated on only one methyl group (2n).

Figure 13:
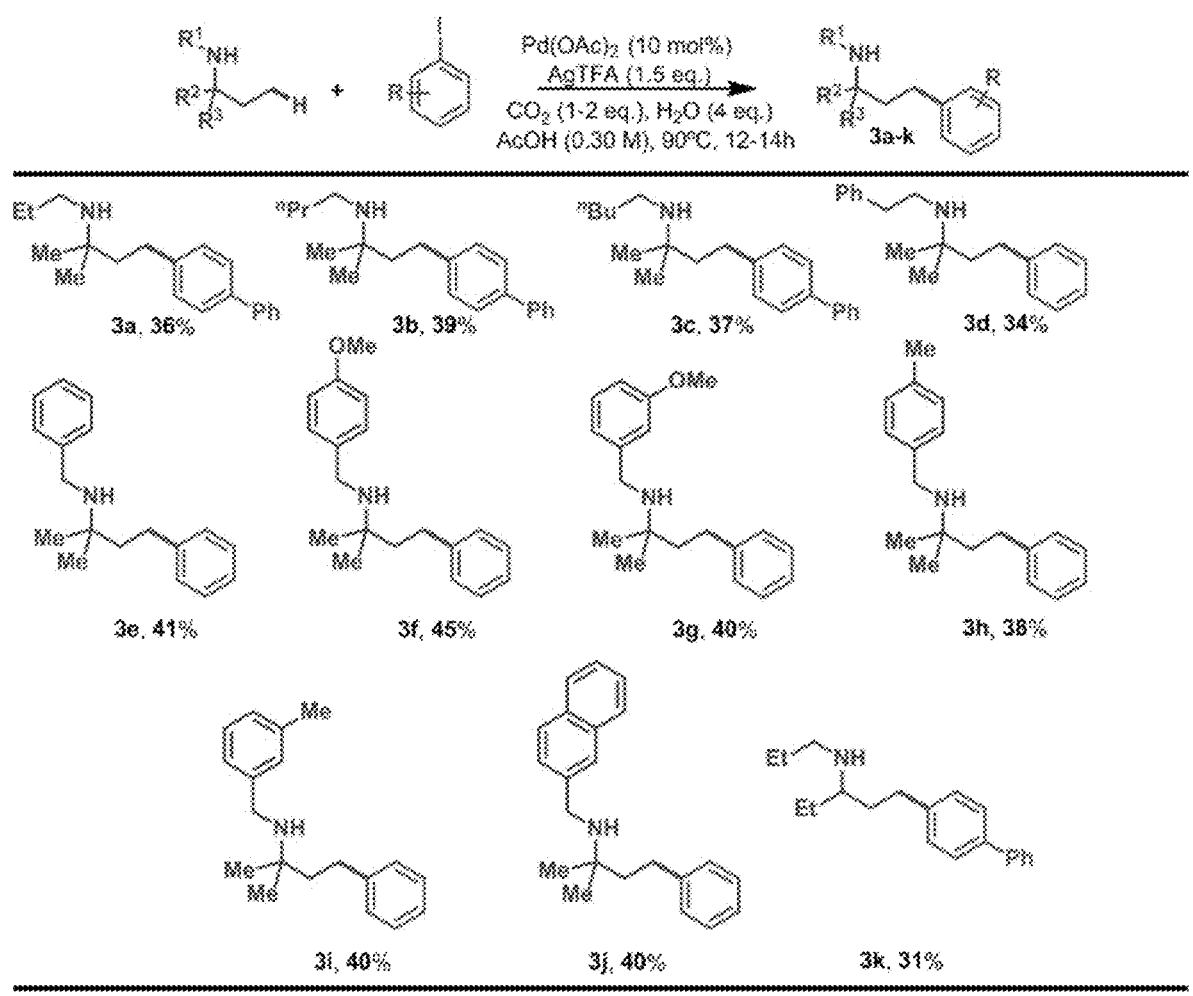
FIG. 13: Table 3, showing the reaction scope of secondary amines for $CO_2$-directed γ-C—H arylation.

The use of carbon dioxide as a directing group compares well against other transient directing groups for the C—H activation of primary amines. However, unlike imine-type directing groups, these carbamates can also readily form using secondary amines. Indeed, by increasing the initial loading of $CO_2(s)$ and ostensibly the pressure of carbon dioxide during the reaction, a variety of acyclic 2° amines could also be selectively arylated (Table 3, FIG. 13). Simple aliphatic chains were permissible (3a-3c), including one substrate with a homobenzylic sidechain (3d). Interestingly, although the substrate for 3a contains multiple terminal γ-C—H positions, the reaction takes place selectively on the side of the amine with the more substituted a-carbon. Benzylamines are also viable substrates, and selective γ-C(sp$^3$)-H functionalization was again observed (3e-3k). Even moving to less sterically-hindered α-secondary 2° amines, the arylation products can still be observed (3i). The carbon dioxide pressure is important for these transformations, and if the pressure is lowered, the yield decreases, with concomitant recovery of various amine oxidation products.

Figure 11:
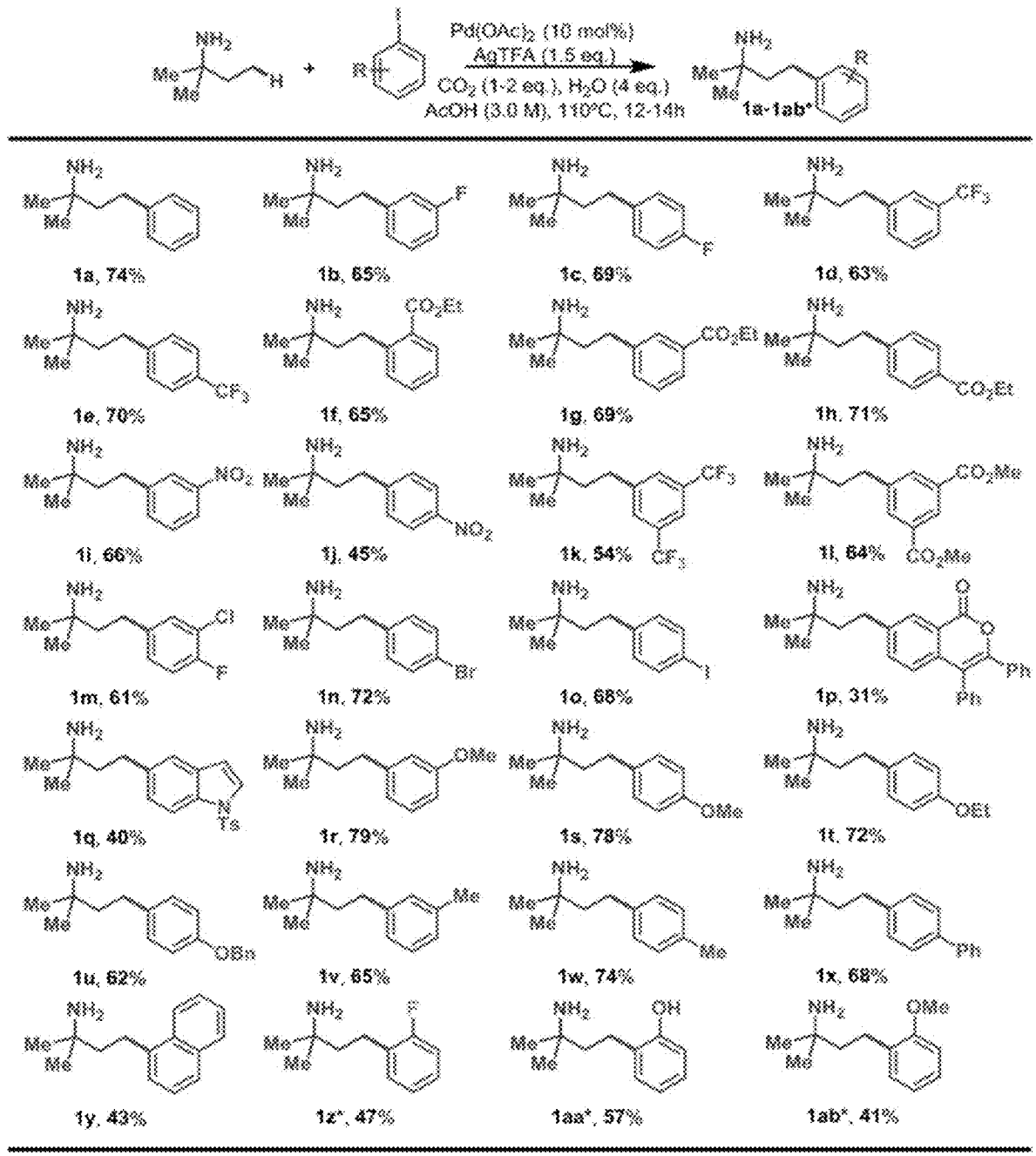
FIG. 11: Table 1, showing the reaction scope of aryl iodides for $CO_2$-directed γ-C—H arylation of aliphatic amines.

To better understand the transformation, non-stoichiometric amounts of $CO_2$ were experimented with. Although roughly 1-2 equivalents of $CO_2$ had been used in the reaction with primary amines, it was believed that $CO_2$ could be acting catalytically like other transient directing groups. As such, the tert-amyl ammonium carbamate salt 4 was prepared by mixing the liquid amine with $CO_2$ until the sample completely solidified (FIG. 11). Brief drying under vacuum to remove any unreacted carbon dioxide or amine gave 4 in 94% yield. When this salt was used in place of the amine and stoichiometric carbon dioxide in the arylation reaction, the desired product was obtained in 64% yield. This indicates that the formation of the carbamate directing group is reversible under the reaction conditions.

Whether the C—H activation step is reversible was also evaluated. To determine whether or not this was the case, the standard reaction on tert-amyl amine was run under AcOD instead of the protonated solvent, and the product 1a was analyzed for D-incorporation (FIG. 11) by $^1$H NMR. Surprisingly, the product was obtained in 83% yield. However, there was no observed deuterium enrichment at the γ-C—H position, indicating either that C—H activation is irreversible, or that the next step in the mechanism is faster, preventing facile incorporation of deuterium.

Although the reaction conditions are consistent with the majority of CMD-based C—H activations using palladium, a competing strategy for amine-based C—H activation in the art has been to protonate the amine, thereby deactivating more proximal C—H bonds for C—H activation. To distinguish between a directing vs. deactivating effect in the reaction, attempts were made to isolated and characterize a cyclometallated intermediate. Repeated attempts were unsuccessful in isolating any organometallic intermediates, but there is other evidence indicating a directing rather than deactivation pathway towards the selectivity observed in these reaction. The first piece of evidence is that despite the presence of less deactivated and equally sterically-accessible C—H bonds at the ε and η positions respectively, products 2f and 2g were isolated with solely γ-arylation observed (FIG. 12). This would not be the expected outcome if a deactivating pathway were in play. Another piece of evidence is that substrate 5 bearing a deactivated 2-fluorobenzyl group gave no conversion when subjected to the standard conditions. Attempts to first prepare an ammonium carbamate salt such as 4 were unsuccessful, likely because the deactivating benzyl group prevents the amine from undergoing nucleophilic attack on carbon dioxide under neat conditions. If the reaction were proceeding through a deactivation pathway rather than a directing pathway, a comparable reactivity for this substrate should result.

The method is a relatively mild strategy for utilization of carbon dioxide as a directing group for C—H activation. Unlike other transient directing groups for amines, this in situ carbamate strategy can be applied to both primary and secondary amines, and the reaction has a broad substrate scope with sufficiently nucleophilic amines. Given that tertiary amine-$CO_2$ adducts are known, it is also possible that this methodology can be extended to these more challenging substrates, opening up the possibility to perform late stage alkaloid derivatization. This directing strategy is furthermore expected to be compatible with other organometallic reactions such as hydrofunctionalization of olefins that can make use of the weakly-coordinating carbamate moiety.

Materials and Methods $^1$H, $^{13}$C, and $^{19}$F spectra were recorded on either a Varian Inova 400 MHz NMR spectrometer or a Varian Inova 600 MHz NMR spectrometer, and were processed using MestReNova by Mestrelab Research S.L. Proton ($^1$H) chemical shifts are reported in parts per million (δ) with respect to tetramethylsilane (TMS, δ=0), and referenced internally with respect to the protio solvent impurity. Carbon ($^{13}$C) chemical shifts are reported in parts per million (δ) with respect to tetramethylsilane (TMS, δ=0), and referenced internally with respect to the carbon signal of the solvent. Fluorine ($^{19}$F) chemical shifts are reported in parts per million (δ) and referenced internally with respect to hexafluorobenzene included in an insert tube ($C_6F_6$, δ=-164.9). Deuterated NMR solvents were obtained from Cambridge Isotope Laboratories, Inc., Andover, Mass., and used without further purification. Mass spectra were recorded on an Agilent 6530 LC Q-TOF mass spectrometer using electrospray ionization with fragmentation voltage set at 115 V or lower for sensitive substrates, and processed with an Agilent MassHunter Operating System, or on a Waters SYNAPT G2-Si High Definition Mass Spectrometer. For limited cases where ESI data was not obtained, an Agilent 5975C Inert XL MSD with Triple-Axis Detector was used, and data was processed using 5975C MSD Data Analysis software. All other materials were obtained from Sigma-Aldrich Chemical Company, St. Louis, Mo., Combi-Blocks, San Diego, Calif., Oakwood Chemical, Estill, S.C., Alfa Aesar, Ward Hill, Mass., Acros Organic, Geel, Belgium, or TCI, Tokyo, Japan, and were used as received.

Synthesis of 1° Amine Substrates

Figure 15:
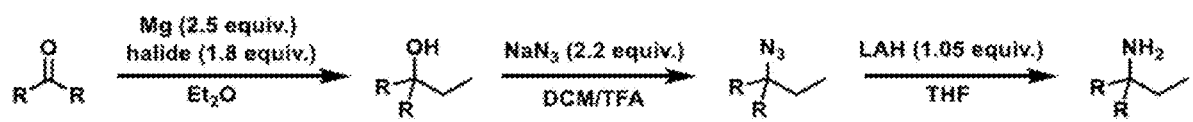
FIG. 15: General procedure for synthesis of primary amines bearing an a-tertiary center.

Method A—General Procedure for Synthesis of Primary Amines Bearing an α-Tertiary Center FIG. 15 depicts the general procedure for producing primary amines.

To an oven dried 50 mL round bottom flask was added freshly ground magnesium turnings (2.5 equiv.) and a single crystal of iodine. The flask was placed under $N_2$, followed by addition of diethyl ether (10 mL). After the stirring for 15 min at room temperature, the organohalide (1.8 equiv.) was added dropwise. The reaction mixture was refluxed for 1 h, followed by cooling to ~0-5° C. After cooling, the appropriate ketone (1.0 equiv.) was added as an ether solution in a dropwise manner, ensuring to maintain a low temperature. After stirring for 4-5 h at 0° C., the reaction mixture was quenched with saturated aqueous ammonium chloride ($NH_4Cl$) and extracted with diethyl ether (3×10 mL). The combined organic layer was washed with brine, dried over $Na_2SO_4$ (s), and concentrated in vacuo to give the crude alcohol product, which was used for the next step without any further purification.

To a solution of the alcohol (1.0 equiv.) in anhydrous $CH_2Cl_2$ (10 mL), $NaN_3$ (2.2 equiv.) was added at room temperature under a nitrogen atmosphere. The suspension was cooled to -5° C., followed by dropwise addition of a 1:2 mixture of TFA:DCM (8.4 equiv. of TFA) under vigorous stirring over a period of 15 min. The resulting suspension was stirred at 0° C. for an additional 1-2 h. The reaction mixture was quenched with distilled $H_2O$, followed by the dropwise addition of a 1:1 mixture of 14% aqueous $NH_4OH$ solution (5.0 mL). After 30 min, the reaction mixture was extracted with $CH_2Cl_2$ (20 mL), and the organic layer was washed with $H_2O$, brine, and dried over $Na_2SO_4$. The filtrate was concentrated in vacuo and the crude azide was used in the next step without further purification.

To a solution of the azide (1.0 equiv.) in anhydrous THF (10 mL) was added $LiAlH_4$ (1.05 equiv.) portion wise at 0° C. under a nitrogen atmosphere. The reaction mixture was stirred at room temperature for 3-4 h, and then quenched by dropwise addition of 1.0 M aqueous NaOH. The reaction mixture was then portioned between $Et_2O$ and 1.0 M aqueous HCl. The aqueous layer was treated with 28% aqueous $NH_4OH$ solution, followed by extraction with $CH_2Cl_2$ (2×10 mL). The filtrate was concentrated in vacuo and the residual amine was purified by flash column chromatography.

Figure 16:
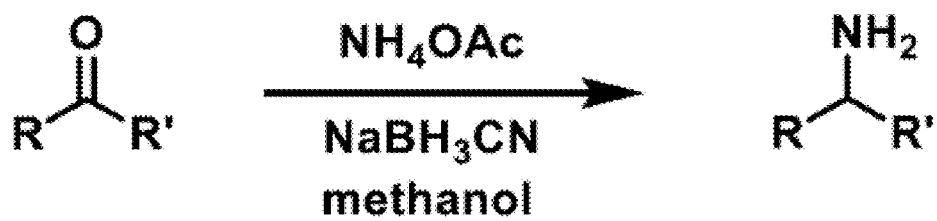
FIG. 16: General procedure for producing a-secondary amines via reductive amination.

Method B—General Procedure for Synthesis of α-Secondary Amines Via Reductive Amination FIG. 16 shows the general procedure for producing α-secondary amines.

To a solution of the carbonyl compound (1.0 equiv.) in methanol (10 mL) was added ammonium acetate (10 equiv.) at room temperature under a nitrogen atmosphere. After the reaction mixture was stirred for 90 min at room temperature, $NaBH_3CN$ was added portion wise. The reaction mixture was stirred for 56 h at room temperature, followed by dilution with NaOH solution (1.0 M, 10 mL). After stirring for 30 min at room temperature, the reaction mixture was then portioned between $Et_2O$ and 1.0 M HCl. The aqueous layer was basified with 28% aqueous $NH_4OH$ solution (pH 8.0), and then extracted with $CH_2Cl_2$ (2×10 mL). The filtrate was concentrated in vacuo and the residual amine was purified by flash column chromatography.

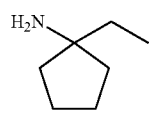

1-Ethylcyclopentan-1-amine (S-1)

Method A used. Cyclopentanone (500 mg) was used. Product recovered as a yellow oil with residual $CH_2Cl_2$ that could not be completely removed by vacuum (134 mg, 20% yield), and that was unstable under ESI-MS conditions. $^1$H NMR (400 MHz, CDCl$_3$) δ 1.74-1.69 (m, 2H), 1.59-1.56 (m, 2H), 1.50-1.42 (m, 4H), 1.40-1.37 (m, 2H), 0.89 (t, J=8.0 Hz, 3H). $^{13}$C NMR (101 MHz, CDCl$_3$) δ 61.43, 40.10, 35.30, 24.14, 9.10. LRMS (EI): calcd. 113.1 [M]+ Found: 113.1.

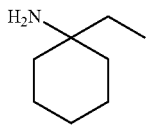

1-Ethylcyclohexan-1-amine (S-2)

Method A used. Cyclohexanone (1.0 g) was used. Product recovered as a yellow oil (674 mg, 52% yield), which was found to match the data reported in the literature. $^1$H NMR (400 MHz, CDCl$_3$) δ 1.59-1.33 (m, 12H), 0.86 (t, J=8.0 Hz, 3H). HRMS (ESI-MS): calcd. 128.1440 [M+H]+ Found: 128.1438.

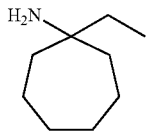

1-Ethylcycloheptan-1-amine (S-3)

Method A used. Cycloheptanone (1.0 g) was used. Product recovered as a yellow oil (818 mg, 65% yield), which was found to match the data reported in the literature. $^1$H NMR (400 MHz, CDCl$_3$) δ 1.54-1.45 (m, 8H), 1.41-1.34 (m, 6H), 0.85 (t, J=8.0 Hz, 3H). HRMS (ESI-MS): calcd. 142.1596 [M+H]+ Found: 142.1594.

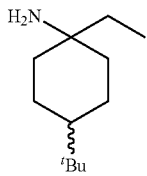

4-(tert-Butyl)-1-ethylcyclohexan-1-amine (S-4)

Method A used. 4-tert-butylcyclohexanone (500 mg) used. Product recovered as a colorless oil (89 mg, 15% yield). $^1$H NMR (400 MHz, CDCl$_3$) δ 1.77-1.74 (m, 1H), 1.62-1.51 (m, 3H), 1.51-1.47 (m, 1H), 1.43-1.38 (m, 2H), 1.34-1.24 (m, 4H), 0.89-0.85 (m, 3H), 0.83-0.81 (m, 9H). $^{13}$C NMR (101 MHz, CDCl$_3$) δ 72.25, 70.83, 48.12, 38.42, 36.98, 36.65, 32.51, 32.35, 27.76, 27.71, 24.50, 22.58, 7.65, 7.07. HRMS (ESI-MS): calcd. 184.2066 [M+H]+ Found: 184.2060.

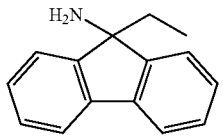 [SMILES: CCC1(N)c2ccccc2-c2ccccc21]

9-Ethyl-9H-fluoren-9-amine (S-5)

Method A used. Fluorenone (1.0 g) was used. Product recovered as a yellow gummy oil (627 mg, 54% yield), which was found to match the data reported in the literature. Rf=0.46 (Hex/EA=1:1). $^1$H NMR (400 MHz, CDCl$_3$) δ 7.66-7.65 (m, 2H), 7.47-7.45 (m, 2H), 7.37-7.29 (m, 4H), 2.07 (q, J=8.0 Hz, 2H), 1.83 (br, 2H, NH2), 0.45 (t, J=8.8 Hz, 3H). HRMS (ESI-MS): calcd. 210.1283 [M+H]+ Found: 210.1277.

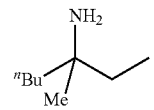

3-Methylheptan-3-amine (S-6)

Method A used. Heptan-3-one (500 mg) was used. Product recovered as a colorless oil (209 mg, 37% yield), which was found to match the data reported in the literature. $^1$H NMR (400 MHz, CDCl$_3$) δ 1.31-1.21 (m, 8H), 0.94-0.92 (m, 3H), 0.84-0.77 (m, 6H). $^{13}$C NMR (101 MHz, CDCl$_3$) δ 51.33, 42.00, 35.06, 27.60, 26.20, 23.48, 14.19, 8.30. HRMS (ESI-MS): calcd. 130.1596 [M+H]+ Found: 130.1592.

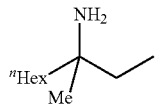

3-Methylnon-3-amine (S-7)

Method A used. Octan-2-one (500 mg) was used. Product recovered as a colorless oil (429 mg, 70% yield). $^1$H NMR (400 MHz, CDCl$_3$) δ 1.34 (br, 2H, NH$_2$), 1.20-1.10 (m, 12H), 0.84-0.82 (m, 3H), 0.70-0.65 (m, 6H). $^{13}$C NMR (101 MHz, CDC$_{l3}$) δ 51.15, 42.02, 34.76, 31.71, 29.87, 27.27, 23.69, 22.47, 13.88, 8.03. HRMS (ESI-MS): calcd. 158.1909 [M+H]+ Found: 158.1911.

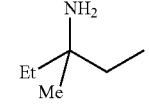

3-Methylpentan-3-amine (S-8)

Method A used. Pentan-3-one (500 mg) was used. Product recovered as a colorless oil (182 mg, 31% yield), which was found to match the data reported in the literature. $^1$H NMR (400 MHz, CDCl₃) δ 1.47-1.41 (m, 4H), 1.09 (s, 3H), 0.87-0.83 (m, 6H). HRMS (ESI-MS): calcd. 102.1283 [M+H]+ Found: 102.1278.

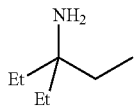

3-Ethylpentan-3-amine (S-9)

Method A used. Pentan-3-one (500 mg) was used, which was found to match the data reported in the literature. Product recovered as a yellow oil (174 mg, 26% yield). ¹H NMR (400 MHz, CDCl₃) δ 1.44 (q, J=8.0 Hz, 6H), 0.84 (t, J=8.0 Hz, 9H). HRMS (ESI-MS): calcd. 116.1439 [M+H]+ Found: 116.1428.

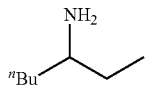

Heptan-3-amine (S-10)

Method B used. Heptan-3-one (500 mg) was used. Product recovered as a colorless oil (232 mg, 46% yield), which was found to match the data reported in the literature. ¹H NMR (400 MHz, CDCl₃) δ 1.44-1.34 (m, 2H), 1.29-1.16 (m, 6H), 1.06-1.01 (m, 1H), 0.84-0.81 (m, 6H). HRMS (ESI-MS): calcd. 116.1439 [M+H]+ Found: 116.1375.

Synthesis of Disilanol Amine

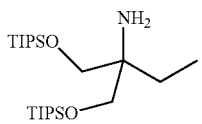

6-Ethyl-3,3,9,9-tetraisopropyl-2,10-dimethyl-4,8-dioxa-3,9-disilaundecan-6-amine (S-11)

A stirred solution of 2-amino-2-ethyl-1,3-propanediol (1.0 g, 8.39 mmol, 1.0 equiv) and Et₃N (4.7 mL, 33.6 mmol, 4.0 equiv) in CH₂Cl₂ (10 mL) was treated dropwise with triisopropylsilyl chloride (3.9 mL, 18.5 mmol, 2.2 equiv) at 0° C. under nitrogen atmosphere. The resulting mixture was stirred at room temperature for 36 h. After 36 h, the mixture was washed with water and the organic layer was dried over anhydrous Na₂SO₄. The filtrate was concentrated under reduced pressure to yield the O-silylated amine as a colorless oil (3.567 g, 98%). ¹H NMR (400 MHz, CDCl₃) δ 3.57-3.50 (m, 4H), 1.42 (q, J=8.0 Hz, 2H), 1.11-1.00 (m, 42H), 0.87 (t, J=8.0 Hz, 3H). HRMS (ESI-MS): calcd. 432.3694 [M+H]+ Found: 432.3696.

Synthesis of Secondary Amine Substrates

Figure 17:
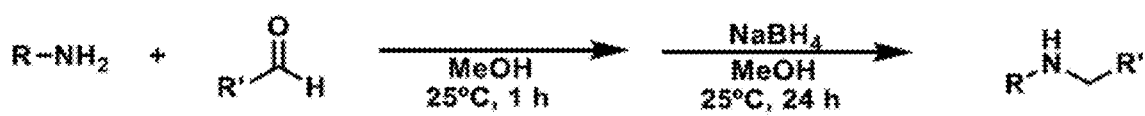
FIG. 17: General procedure for producing secondary amines via reductive amination from the corresponding aldehydes.

Method A—General Procedure for Synthesis of Secondary Amines Via Reductive Amination from the Corresponding Aldehydes FIG. 17 shows the typical procedure for a reductive amination. To a 35-mL vial charged with a stir bar was added the primary amine, the aldehyde, and 15 mL of methanol. The reaction was stirred at room temperature for 60 minutes, and then sodium borohydride (2.0 equiv) was added slowly and the reaction stirred overnight. The reaction was then acidified using 1.2 M hydrochloric acid, followed by extracted with diethyl ether (2×50 mL). The aqueous layer was then made basic with ammonium hydroxide and extracted with DCM (2×50 mL). The product was concentrated in vacuo to give the secondary amine product.

Figure 18:
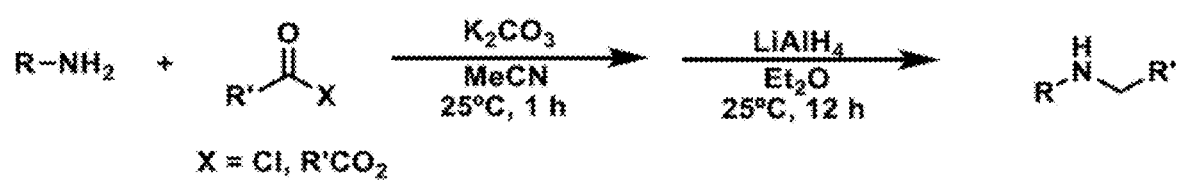
FIG. 18: General procedure for producing secondary amines via reductive amination from the corresponding acyl precursor.

Method B—General Procedure for Synthesis of Secondary Amines Via Reductive Amination from the Corresponding Acyl Precursor FIG. 18 shows the typical procedure for a reductive amination. To a 35-mL vial charged with a stir bar was added the primary amine, the aldehyde, and 15 mL of methanol. The reaction was stirred at room temperature for 60 minutes, and then sodium borohydride (2.0 equiv) was added slowly and the reaction stirred overnight. The reaction was then acidified using 1.2 M hydrochloric acid, followed by extracted with diethyl ether (2×50 mL). The aqueous layer was then made basic with ammonium hydroxide and extracted with DCM (2×50 mL). The product was concentrated in vacuo to give the secondary amine product.

Figure 19:
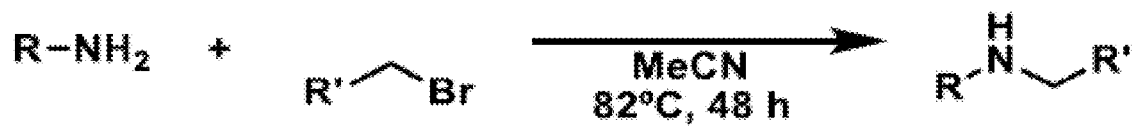
FIG. 19: General procedure for producing secondary amines via amine alkylation.
Figure 21:
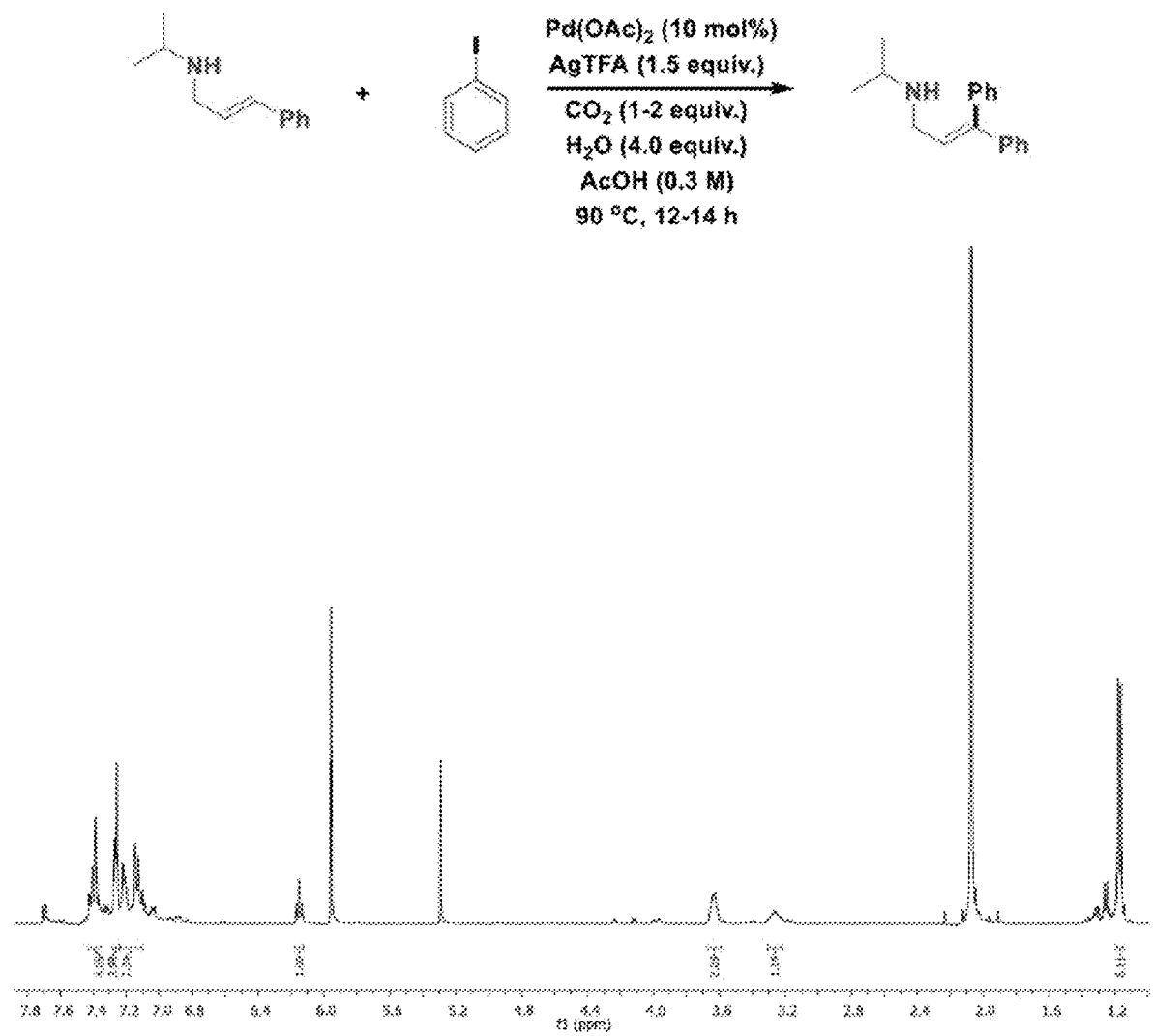
FIG. 21: Arylation of allylamines.

Method C—General Procedure for Synthesis of Secondary Amines Via Amine Alkylation FIG. 19 shows the typical procedure for amine alkylation. tert-Pentylamine was combined with alkyl halide, followed by addition of MeCN (5 mL). The reaction was heated to 82° C. in a sealed 35 mL reaction vial with a PTFE lined cap. After 48 h, the reaction was cooled, and all volatiles removed in vacuo. The resulting residue was treated with 6M KOH, followed by extracting with dichloromethane (3×25 mL). The combined organic fractions were dried over MgSO₄, followed by evaporation in vacuo to give the desired product.

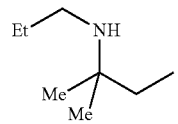

N-(tert-Pentyl)propan-1-amine (S-12)

Method B used. tert-Pentylamine (2.0 mL, 17.2 mmol), propionyl chloride (1.50 mL, 17.2 mmol), and potassium carbonate (3.57 g, 25.8 mmol) were used in the first part of the reaction, giving the amide intermediate as a colorless oil (1.07 g, 43%). Amide intermediate (210 mg, 1.47 mmol) and lithium aluminum hydride (97 mg, 2.56 mmol) were used in the second part of the reaction, giving the amine product as a colorless oil (108 mg, 57% yield). ¹H NMR (400 MHz, CDCl₃) δ 2.42 (t, J=7.3 Hz, 2H), 1.45 (sex, J=7.4 Hz, 2H), 1.38 (q, J=7.5 Hz, 2H), 1.00 (s, 6H), 0.89 (t, J=7.4 Hz, 3H), 0.80 (t, J=7.5 Hz, 3H). ¹³C NMR (101 MHz, CDCl₃) δ 52.4, 44.0, 32.9, 26.6, 24.1, 12.1, 8.3. HRMS (ESI-MS): calcd. 130.1596 [M+H]+ Found: 130.1591.

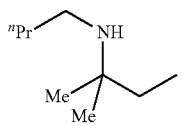

N-(tert-Pentyl)butan-1-amine (S-13)

Method A used. tert-Pentylamine (0.67 mL, 5.73 mmol), butyraldehyde (0.57 mL, 6.31 mmol), and sodium borohydride (0.44 g, 11.5 mmol) were used in the reaction, giving the amine product as a colorless oil in approximately 95% purity, which was further purified by column chromatography over silica using DCM/MeOH/NH$_4$OH (95:5:1) to give a colorless oil (443 mg, 54% yield) that was unstable under ESI-MS conditions. $^1$H NMR (400 MHz, CDCl$_3$) δ 2.46 (t, J=8.0 Hz, 2H), 1.41-1.30 (m, 5H), 1.01 (s, 6H), 0.93-0.88 (m, 5H), 0.81 (t, J=8.0 Hz, 3H). $^{13}$C NMR (101 MHz, CDCl$_3$) δ 43.81, 43.54, 35.19, 35.27, 26.02, 19.84, 14.52, 8.42. LRMS (EI): calcd. 143.2 [M]+ Found: 143.2.

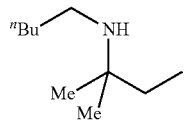

N-(tert-Pentyl)pentan-1-amine (S-14)

Method B used. tert-Pentylamine (2.36 mL, 20.3 mmol), valeroyl chloride (2.0 mL, 16.9 mmol), and potassium carbonate (4.67 g, 33.8 mmol) were used in the first part of the reaction, giving the amide intermediate as a colorless oil (1.10 g, 38%). Amide intermediate (100 mg, 0.58 mmol) and lithium aluminum hydride (106 mg, 2.79 mmol) were used in the second part of the reaction, giving the amine product as a colorless oil (65 mg, 71% yield). $^1$H NMR (400 MHz, CDCl$_3$) δ 2.43 (t, J=7.2 Hz, 2H), 1.41 (quint, J=7.0 Hz, 2H), 1.36 (q, J=7.5 Hz, 2H), 1.28 (m, 4H), 0.98 (s, 6H), 0.86 (t, J=6.8 Hz, 3H), 0.79 (t, J=7.5 Hz, 3H). $^{13}$C NMR (101 MHz, CDCl$_3$) δ 52.3, 42.1, 33.0, 30.9, 29.9, 26.7, 22.8, 14.2, 8.4. HRMS (ESI-MS): calcd. 192.1910 [M+H]+ Found: 192.1911.

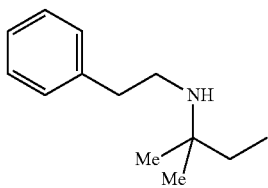

2-Methyl-N-phenethylbutan-2-amine (S-15)

Method C used. tert-Pentylamine (1.66 g, 18.3 mmol) was combined with 2-phenethylbromide (680 mg, 3.67 mmol), followed by addition of MeCN (5 mL). The reaction was heated to 82° C. in a sealed 35 mL reaction vial with a PTFE lined cap. After 48 h, the reaction was cooled, and all volatiles removed in vacuo. The resulting residue was treated with 6M KOH, followed by extracting with dichloromethane (3×25 mL). The combined organic fractions were dried over MgSO$_4$, followed by evaporation in vacuo to give the desired product as a yellow oil (431 mg, 61% yield). Rf=0.4 (Hex/EA=1:1). $^1$H NMR (400 MHz, CDCl$_3$) δ 7.30-7.26 (m, 2H), 7.22-7.17 (m, 3H), 2.77 (s, 4H), 1.37 (q, J=8.0 Hz, 2H), 1.00 (s, 6H), 0.74 (t, J=8.0 Hz, 3H). $^{13}$C NMR (101 MHz, CDCl$_3$) δ 140.2, 128.6, 128.3, 126.1, 52.3, 43.5, 37.2, 32.8, 26.5, 8.1. HRMS (ESI-MS): calcd. 192.1753 [M+H]+ Found: 192.1756.

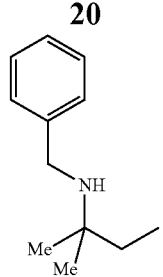

N-Benzyl-2-methylbutan-2-amine (S-16)

Method A used. tert-Pentylamine (500 mg, 5.73 mmol), benzaldehyde (639 mg, 6.02 mmol), and sodium borohydride (327 mg, 8.60 mmol) used. Product recovered as a colorless oil (823 mg, 81% yield). Rf=0.4 (Hex/EA=4:1). $^1$H NMR (400 MHz, CDCl$_3$) δ 7.36-7.35 (m, 2H), 7.32 (t, J=4.0 Hz, 2H), 7.24 (t, J=4.0 Hz, 2H), 3.68 (s, 2H), 1.50 (q, J=4.0 Hz, 2H), 1.12 (s, 6H), 0.90 (t, J=4.0 Hz, 3H). $^{13}$C NMR (101 MHz, CDCl3) δ 141.71, 128.52, 128.41, 126.85, 52.85, 46.84, 33.11, 26.95, 8.46. HRMS (ESI-MS): calcd. 178.1596 [M+H]+ Found: 178.1597.

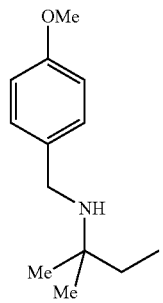

N-(4-Methoxybenzyl)-2-methylbutan-2-amine (S-17)

Method A used. tert-Pentylamine (1.0 g, 11.5 mmol), 4-methoxybenzaldehyde (1.6 g, 12.0 mmol), and sodium borohydride (0.65 g, 17.2 mmol) used. Product recovered as a colorless oil (2.1 g, 89% yield). Rf=0.34 (Hex/EA=1:1). $^1$H NMR (400 MHz, CDCl$_3$) δ 7.27 (d, J=8.0 Hz, 2H), 6.86 (d, J=8.0 Hz, 2H), 3.78 (s, 3H), 3.60 (s, 2H), 1.50 (q, J=8.0 Hz, 2H), 1.11 (s, 6H), 0.90 (t, J=8.0 Hz, 3H). $^{13}$C NMR (101 MHz, CDCl$_3$) δ 158.41, 133.47, 129.37, 113.72, 55.16, 52.66, 45.98, 32.86, 26.70, 8.29. HRMS (ESI-MS): calcd. 208.1702 [M+H]+ Found: 208.1697.

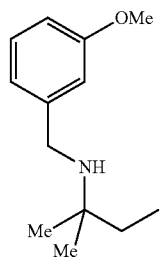

N-(3-Methoxybenzyl)-2-methylbutan-2-amine (S-18)

Method A used. tert-Pentylamine (1.0 g, 11.5 mmol), 3-methoxybenzaldehyde (1.6 g, 12.0 mmol), and sodium borohydride (0.65 g, 17.2 mmol) were used. Product was recovered as a yellow oil (1.9 g, 81% yield). Rf=0.34 (Hex/EA=1:1). 1H NMR (400 MHz, CDCl$_3$) δ 7.25-7.21 (m, 1H), 6.95-6.93 (m, 2H), 6.79-6.77 (m, 1H), 3.81 (m, 3H), 3.65 (m, 2H), 1.49 (q, J=8.0 Hz, 2H), 1.11 (s, 6H), 0.90 (t, J=8.0 Hz, 3H). $^{13}$C NMR (101 MHz, CDCl$_3$) δ 159.73, 143.26, 129.42, 120.63, 113.89, 112.24, 55.25, 52.87, 46.75, 33.08, 26.85, 8.42. HRMS (ESI-MS): calcd. 208.1702 [M+H]+ Found: 208.1700.

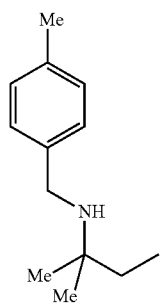

N-(4-Tolyl)-2-methylbutan-2-amine (S-19)

Method A used. tert-Pentylamine (1.0 g, 11.5 mmol), 4-methylbenzaldehyde (1.5 g, 12.0 mmol), and sodium borohydride (0.65 g, 17.2 mmol) were used. Colorless oil (2.0 g, 91% yield). Rf=0.5 (Hex/EA=1:1). $^1$H NMR (400 MHz, CDCl$_3$) δ 7.25 (d, J=8.0 Hz, 2H), 7.13 (d, J=8.0 Hz, 2H), 3.64 (s, 2H), 2.34 (s, 3H), 1.50 (q, J=8.0 Hz, 2H), 1.12 (s, 6H), 0.90 (t, J=8.0 Hz, 3H). $^{13}$C NMR (101 MHz, CDCl$_3$) δ 138.54, 136.33, 129.15, 128.32, 52.82, 46.49, 33.04, 26.88, 21.21, 8.42. HRMS (ESI-MS): calcd. 192.1753 [M+H]+ Found: 192.1753.

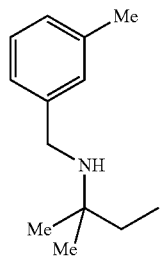

N-(3-Tolyl)-2-methylbutan-2-amine (S-20)

Method A used. tert-Pentylamine (1.0 g, 11.5 mmol), 3-methylbenzaldehyde (1.5 g, 12.0 mmol), and sodium borohydride (0.65 g, 17.2 mmol) were used. Product recovered as a colorless oil (1.5 g, 70% yield). Rf=0.4 (Hex/EA=1:1). $^1$H NMR (400 MHz, CDCl$_3$) δ 7.24-7.11 (m, 3H), 7.11-7.06 (m, 1H), 3.64 (s, 2H), 2.36 (s, 3H), 1.52-1.49 (m, 2H), 1.13 (s, 6H), 0.93-0.90 (m, 3H). $^{13}$C NMR (101 MHz, CDCl$_3$) δ 141.48, 138.10, 129.19, 128.41, 127.58, 125.44, 52.86, 46.81, 33.05, 26.91, 21.55, 8.46. HRMS (ESI-MS): calcd. 192.1753 [M+H]+ Found: 192.1750.

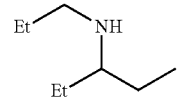

N-Propylpentan-2-amine (S-22)

Method A used. 3-Aminopentane (1.17 g, 13.4 mmol), propionaldehyde (648 mg, 11.2 mmol), and sodium borohydride (847 mg, 22.4 mmol) were used. Product was recovered as a colorless oil (959 mg, 66% yield). $^1$H NMR (400 MHz, CDCl$_3$) δ 2.51 (t, J=7.3 Hz, 2H), 2.33 (quint, J=5.9 Hz, 1H), 1.47 (sex, J=7.3 Hz, 2H), 1.39 (quint, J=6.7 Hz, 4H), 0.90 (t, J=7.3 Hz, 3H), 0.85 (t, J=7.4 Hz, 6H). $^{13}$C NMR (101 MHz, CDCl$_3$) δ 125.4, 60.2, 49.3, 26.0, 23.7, 12.0, 10.1. HRMS (ESI-MS): calcd. 130.1596 [M+H]+ Found: 130.1593.

Synthesis of Iodoaromatics

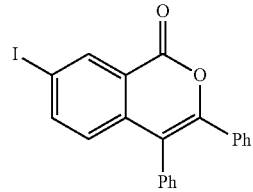 [SMILES: O=c1oc(-c2ccccc2)c(-c2ccccc2)c2ccc(I)cc12]

3-Iodoisocoumarin (S-23)

3-iodobenzoic acid (373 mg, 1.5 mmol, 1.0 equiv), diphenylacetylene (321 mg, 1.8 mmol, 1.2 equiv), [RhCp* (CH$_3$CN)$_3$] (SbF$_6$)$_2$ (9.3 mg, 0.015 mmol, 0.01 equiv), and copper (II) acetate (15.0 mg, 0.075 mmol, 0.05 equiv) were added to a 50 mL round bottom flask. A stir bar was added and a water condenser attached to the flask. The flask and condenser were placed in a sand bath and 7.5 mL of DMF were added through the condenser. The reaction mixture was stirred and heated to 120° C. for 2 h. After 2 h, the reaction was cooled, and then poured into a solution of sodium EDTA. The EDTA solution was extracted with diethyl ether (4×50 mL), and the combined ether extracts were washed with EDTA (2×50 mL). The ether layer was then dried over anhydrous MgSO$_4$ and filtered. The filtrate was concentrated in vacuo and then purified using flash chromatography in hexanes/EA (98:2). The material thus obtained was then subjected to recrystallization from 95% ethanol, giving the desired product as a tan solid (158 mg, 25%). $^1$H NMR (400 MHz, CDCl$_3$) δ 8.65 (d, J=1.9 Hz, 1H), 7.82 (dd, J=8.6, 1.9 Hz, 1H), 7.35 (m, 3H), 7.24 (m, 2H), 7.14 (m, 5H), 6.85 (d, J=8.5 Hz, 1H). $^{13}$C NMR (101 MHz, CDCl$_3$) δ 160.7, 151.5, 143.4, 138.1, 133.7, 132.6, 131.1, 129.3, 129.2, 129.2, 128.4, 128.0, 127.1, 121.8, 116.5, 92.8. HRMS (ESI-MS): calcd. 446.986 [M+Na]+ Found: 446.9836.

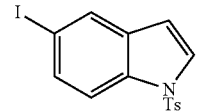

5-Iodo-1-tosyl-1H-indole (S-24)

To a stirred solution of sodium hydride (123 mg, 3.08 mmol, 1.5 equiv.) in DMF (5.0 mL) was added 5-iodoindole (500 mg, 2.05 mmol, 1.0 equiv.) at room temperature under a nitrogen atmosphere. After the reaction mixture was stirred for 30 minutes, tosyl chloride (470 mg, 2.67 mmol, 1.3 equiv.) solution in DMF (3.0 mL) was added via syringe. The reaction mixture was stirred overnight at 0-25° C., and was quenched with water. The quenched reaction mixture was then extracted with EA, dried, and concentrated in vacuo. Rf=0.4 (Hex/EA/DCM=5:1:2). $^1$H NMR (400 MHz, CDCl$_3$) δ 7.84 (d, J=1.6 Hz, 1H), 7.78 (s, 1H), 7.74 (d, J=8.0 Hz, 2H), 7.57-7.52 (m, 2H), 7.18 (d, J=8.0 Hz, 2H), 6.56 (s, 1H), 2.31 (s, 3H). HRMS (ESI-MS): calcd. 419.9533 [M+Na]+ Found: 419.9510.

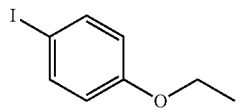

1-Ethoxy-4-iodobenzene (S-25)

The commercially available compound was prepared using the following procedure: To a stirred solution of 4-iodophenol (1.0 g, 4.54 mmol) in ethanol (10 mL) was added potassium carbonate (3.1 g, 22.7 mmol) at room temperature under nitrogen atmosphere. After the reaction mixture was stirred at room temperature for 15 min, iodoethane (0.71 g, 4.45 mmol, 1.0 equiv) was added to it. Reaction mass was heated to reflux and stirred at same temperature for 12 h. After 12 h, the mixture was cooled down to room temperature, quenched with water, and extracted with ethyl acetate (3×10 mL). Ethyl acetate layer was dried over anhydrous Na$_2$SO$_4$ and filtered. The filtrate was concentrated under reduced pressure to afford ethoxy iodobenzene as yellow oil, which was subjected to flash column chromatography using ethylacetate/hexanes (1:10) to afford product as a light yellow oil (1.10 g, 4.32 mmol) in 95% yield. Rf=0.4 (Hex/EA=4:1). $^1$H NMR (400 MHz, CDCl$_3$) δ 7.54 (d, J=8.0 Hz, 2H), 6.67 (d, J=8.0 Hz, 2H), 3.99 (q, J=8.0 Hz, 2H), 1.40 (t, J=8.0 Hz, 3H). HRMS (ESI-MS): calcd. 247.9698; Found: 247.9696.

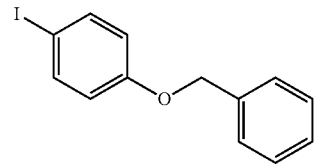 [SMILES: Ic1ccc(OCc2ccccc2)cc1]

1-Benzyloxy-4-iodobenzene (S-26)

The commercially available compound was prepared using the following procedure: To a stirred solution of 4-iodophenol (1.0 g, 4.54 mmol) in acetone (10 mL) was added potassium carbonate (1.9 g, 13.6 mmol) at room temperature under nitrogen atmosphere. After the reaction mixture was stirred at room temperature for 15 min, benzyl bromide (0.78 g, 4.45 mmol, 1.0 equiv.) was added to it. Reaction mass was heated to reflux and stirred at same temperature for 12 h. After 12 h, the mixture was cooled down to room temperature, quenched with water, and extracted with ethyl acetate (3×10 mL). Ethyl acetate layer was dried over anhydrous Na$_2$SO$_4$ and filtered. The filtrate was concentrated under reduced pressure to afford benzyl protected iodobenzene as white solid, which was subjected to crystallization with ethanol to afford white crystalline solid (1.1g, 3.55 mmol) in 77% yield. $^1$H NMR (400 MHz, CDCl$_3$) δ 7.57 (d, J=10 Hz, 2H), 7.44-7.36 (m, 5H), 6.77 (d, J=10 Hz, 2H), 5.04 (s, 2H). HRMS (ESI-MS): calcd. 309.9855; Found: 309.9840.

Optimization and Synthesis of γ-Arylated 1° Amines
Catalytic C(Sp$^3$)-H Arylation of Free Primary Amines The typical procedure for optimization of the γ-arylation of 1 amines is shown in FIG. 5.

Standard conditions: A 7.5 mL vial was charged with Pd(OAc)$_2$ (6.7 mg, 0.03 mmol, 0.10 equiv), silver trifluoroacetate (99.9 mg, 0.45 mmol, 1.5 equiv), organohalide (0.45 mmol, 1.5 equiv), amine (0.30 mmol, 1.0 equiv), acetic acid (1.0 mL), and water (21.7 μL, 1.2 mmol, 4.0 equiv), followed by the addition of dry ice as the CO$_2$ source. The vial was sealed with a PTFE lined cap and stirred at room temperature for 15 min. After 15 min of stirring, the reaction mass was heated in a pie-block at 110° C. under stirring for 12-14 h. After cooling to room temperature, the reaction mixture was concentrated in vacuo. Aq. HCl (10 mL, 1.2 M) was added to the residual reaction mass and stirred for 15 min. The mixture was extracted with ether (8.0 mL) and the organic layer was discarded. The aqueous layer was made basic with ammonium hydroxide solution up to pH=8, followed by extraction with dichloromethane (2×10 mL). The organic layer was washed with water (5.0 mL), followed by brine, and dried over Na$_2$SO$_4$. The filtrate was concentrated under vacuo and further purified by flash column chromatography over silica (DCM/MeOH/NH$_4$OH) to give the C—H arylation product.

Typical Procedure for Substrate Scope Evaluation

FIG. 6 shows the procedure used for evaluating the substrate scope. A 7.5 mL vial was charged with Pd(OAc)$_2$ (6.7 mg, 0.03 mmol, 0.10 equiv), silver trifluoroacetate (99.9 mg, 0.45 mmol, 1.5 equiv), phenyl iodide (92.3 mg, 0.45 mmol, 1.5 equiv), amine (26.3 mg, 0.30 mmol, 1.0 equiv), acetic acid (1.0 mL), and water (21.7 μL, 12.1 mmol, 4.0 equiv) followed by the addition of dry ice as the CO$_2$ source. The vial was immediately sealed with a PTFE lined cap and stirred at room temperature for 15 min. After 15 min of stirring, the reaction vial was heated in a pie-block at 110° C. under stirring for between 12-14h. After cooling to room temperature, the reaction mixture was concentrated in vacuo. Aq. HCl (10 mL, 1.2 M) was added to the residual reaction mass and stirred for 15 min. The mixture was extracted with ether (8.0 mL) and the organic layer was discarded. The aqueous layer was made basic with ammonium hydroxide solution up to pH=8, followed by extraction with dichloromethane (2×10 mL). The organic layer was washed with water (5.0 mL), followed by brine, and dried over Na$_2$SO$_4$. The filtrate was concentrated under vacuo and further purified by flash column chromatography over silica (DCM/MeOH/NH$_4$OH) to give the C—H arylation product.

Characterization

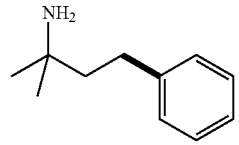

2-Methyl-4-phenylbutan-2-amine (1a)

Reaction time 12 h, purified by DCM/MeOH/NH$_4$OH (100:3:1). Product was recovered as a yellow oil (36.2 mg, 74% yield). Rf=0.2 (DCM/MeOH=4:1). $^1$H NMR (400 MHz, CDCl$_3$) δ 7.25-7.23 (m, 2H), 7.18-7.14 (m, 3H), 2.64-2.61 (m, 2H), 1.68-1.65 (m, 2H), 1.15 (s, 6H). $^{13}$C NMR (101 MHz, CDCl$_3$) δ 142.79, 128.49, 128.40, 125.80, 49.82, 46.95, 31.15, 30.24. HRMS (ESI-MS): calcd. 164.1439 [M+H]+ Found: 164.1436.

4-(3-Fluorophenyl)-2-methylbutan-2-amine (1b)

Reaction time 14 h, purified by DCM/MeOH/NH$_4$OH (100:2:1). Product recovered as a yellow oil (35.3 mg, 65% yield). Rf=0.2 (DCM/MeOH=4:1). $^1$H NMR (400 MHz, CDCl$_3$) δ 7.24-7.18 (m, 1H), 6.95 (d, J=8.0 Hz, 1H), 6.89-6.82 (m, 2H), 2.66-2.61 (m, 2H), 1.66-1.62 (m, 2H), 1.15 (s, 6H). $^{13}$C NMR (101 MHz, CDCl3) δ 162.94 (d, J=244 Hz), 145.43 (d, J=7.0 Hz), 129.79 (d, J=8.0 Hz), 124.00 (J=3.0 Hz), 115.17 (J=20 Hz), 112.58 (d, J=21 Hz), 49.55, 46.74, 30.96, 30.50. $^{19}$F NMR (376 MHz, CDCl$_3$) δ −112.25. HRMS (ESI-MS): calcd. 182.1346 [M+H]+ Found: 182.1343.

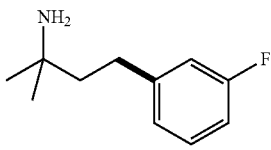

4-(4-Fluorophenyl)-2-methylbutan-2-amine (1c)

Reaction time 14 h, purified by DCM/MeOH/NH$_4$OH (100:2:1). Product was recovered as a colorless oil (37.5 mg, 69% yield). Rf=0.22 (DCM/MeOH=4:1). $^1$H NMR (400 MHz, CDCl$_3$) δ 7.14-7.11 (m, 2H), 6.96-6.93 (m, 2H), 2.63-2.60 (m, 2H), 1.67-1.64 (m, 2H), 1.17 (s, 6H). $^{13}$C NMR (101 MHz, CDCl$_3$) δ 161.26 (d, J=161 Hz), 138.25 (d, J=2.0 Hz), 129.67 (d, J=5.0 Hz), 115.19 (d, J=14 Hz), 49.97, 46.85, 30.30, 30.08. $^{19}$F NMR (376 Hz, CDCl$_3$) δ −116.36. HRMS (ESI-MS): calcd. 182.1346 [M+H]+ Found: 182.1341.

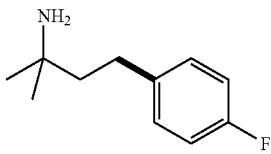

2-Methyl-4-[3-(trifluoromethyl)phenyl]butan-2-amine (1d)

Reaction time 14 h, purified by DCM/MeOH/NH$_4$OH (100:5:1). Product was recovered as a colorless oil (43.7 mg, 63% yield). Rf=0.31 (DCM/MeOH=4:1). $^1$H NMR (400 MHz, CDCl$_3$) δ 7.44-7.41 (m, 2H), 7.37-7.35 (m, 2H), 2.73-2.68 (m, 2H), 1.69-1.64 (m, 2H), 1.17 (s, 6H). $^{13}$C NMR (101 MHz, CDCl$_3$) δ 143.72, 131.84 (d, J=2.0 Hz), 130.71 (q, J=32 Hz), 128.85, 125.07 (q, J=4.0 Hz), 124.35 (d, J=271 Hz), 122.68 (q, J=4.0 Hz), 49.69, 46.83, 31.05, 30.49. $^{19}$F NMR (376 MHz, CDCl$_3$) δ −60.94. HRMS (ESI-MS): calcd. 232.1314 [M+H]+ Found: 232.1312.

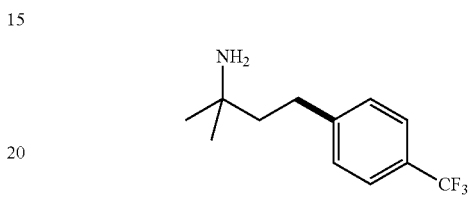

2-Methyl-4-[4-(trifluoromethyl)phenyl]butan-2-amine (1e)

Reaction time 13 h, purified by DCM/MeOH/NH$_4$OH (100:5:1). Product was recovered as a colorless oil (48.6 mg, 70% yield). Rf=0.32 (DCM/MeOH=4:1). $^1$H NMR (400 MHz, CDCl$_3$) δ 7.52 (d, J=6.0 Hz, 2H), 7.29 (d, J=6.0 Hz, 2H), 2.72-2.69 (m, 2H), 1.68-1.65 (m, 2H), 1.17 (s, 6H). $^{13}$C NMR (101 MHz, CDCl$_3$) δ 147.02, 128.71, 125.19 (q, J=21 Hz), 125.40 (q, J=3.0 Hz), 123.57, 49.76, 46.65, 31.09, 30.42. $^{19}$F NMR (376 MHz, CDCl3) δ −60.67. HRMS (ESI-MS): calcd. 232.1314 [M+H]+ Found: 232.1310.

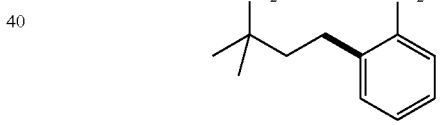

Ethyl 2-(3-amino-3-methylbutyl)benzoate (1f)

Reaction time 12 h, purified by DCM/MeOH/NH$_4$OH (100:2:1). Product was recovered as a yellow oil (45.9 mg, 65% yield). Rf=0.2 (DCM/MeOH=4/1). $^1$H NMR (400 MHz, CDCl$_3$) δ 7.84 (d, J=8.0 Hz, 1H), 7.38 (t, J=8.0 Hz, 1H), 7.24-7.19 (m, 2H), 4.33 (q, J=8.0 Hz, 2H), 2.99-2.95 (m, 2H), 1.64-1.60 (m, 2H), 1.36 (t, J=8.0 Hz, 3H), 1.16 (s, 6H). $^{13}$C NMR (101 MHz, CDCl$_3$) δ 167.61, 144.64, 131.93, 130.97, 130.64, 129.75, 125.77, 60.84, 49.69, 47.29, 30.34, 29.70, 14.46. HRMS (ESI-MS): calcd. 236.1644 [M+H]+ Found: 236.1641.

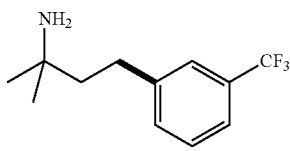

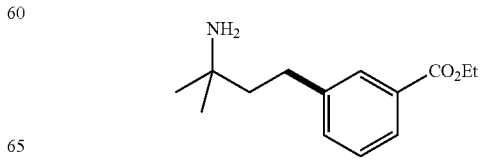

Ethyl 3-(3-amino-3-methylbutyl)benzoate (1g)

Reaction time 13 h, purified by DCM/MeOH/NH$_4$OH (100:3:1). Product was recovered as a yellow oil (48.7 mg, 69% yield). Rf=0.22 (DCM/MeOH=4/1). $^1$H NMR (400 MHz, CDCl$_3$) δ 7.85-7.83 (m, 2H), 7.38-7.30 (m, 2H), 4.35 (q, J=8.0 Hz, 2H), 2.71-2.66 (m, 2H), 1.68-1.64 (m, 2H), 1.38 (t, J=8.0 Hz, 3H), 1.16 (s, 6H). $^{13}$C NMR (101 MHz, CDCl$_3$) δ 166.83, 143.11, 132.96, 130.60, 129.41, 128.44, 127.05, 61.01, 49.59, 47.04, 31.02, 30.53, 14.46. HRMS (ESI-MS): calcd. 236.1644 [M+H]+ Found: 236.1648.

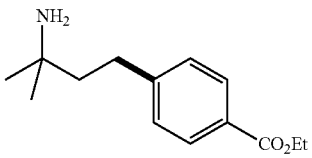

Ethyl 4-(3-amino-3-methylbutyl)benzoate (1h)

Reaction time 12 h, purified by DCM/MeOH/NH$_4$OH (100:2:1). Product was recovered as a colorless oil (50.1 mg, 71% yield). Rf=0.20 (DCM/MeOH=4/1). $^1$H NMR (400 MHz, CDCl$_3$) δ 7.93 (d, J=8.0 Hz, 2H), 7.23 (d, J=8.0 Hz, 2H), 4.33 (q, J=8.0 Hz, 2H), 2.69-2.65 (m, 2H), 1.72 (br, 2H), 1.67-1.62 (m, 2H), 1.35 (t, J=8.0 Hz, 2H), 1.15 (s, 6H). $^{13}$C NMR (101 MHz, CDCl$_3$) δ 166.67, 148.28, 129.74, 128.33, 128.06, 60.84, 49.62, 46.62, 31.26, 30.44, 14.43. HRMS (ESI-MS): calcd. 236.1644 [M+H]+ Found: 236.1648.

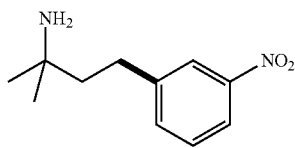

2-Methyl-4-(3-nitrophenyl)butan-2-amine (1i)

Reaction time 14 h, purified by DCM/MeOH/NH$_4$OH (100:4:1). Product was recovered as a yellow oil (41.2 mg, 66% yield). Rf=0.22 (DCM/MeOH=4/1). $^1$H NMR (400 MHz, CDCl$_3$) δ 8.05 (s, 1H), 8.02 (d, J=8.0 Hz, 1H), 7.51 (d, J=8.0 Hz, 1H), 7.42 (t, J=8.0 Hz, 1H), 2.78-2.74 (m, 2H), 1.70-1.66 (m, 2H), 1.17 (s, 6H). $^{13}$C NMR (101 MHz, CDCl$_3$) δ 148.41, 144.91, 134.80, 129.32, 123.23, 121.04, 49.57, 46.62, 30.91, 30.61. HRMS (ESI-MS): calcd. 209.1290 [M+H]+ Found: 209.1285.

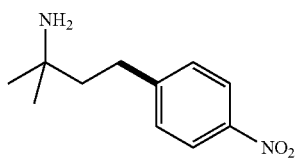

2-Methyl-4-(4-nitrophenyl)butan-2-amine (1j)

Reaction time 12 h, purified by DCM/MeOH/NH$_4$OH (100:4:1). Product was recovered as a yellow oil (28.1 mg, 45% yield). Rf=0.2 (DCM/MeOH=4/1). $^1$H NMR (400 MHz, CDCl$_3$) δ 8.11 (d, J=6.0 Hz, 2H), 7.32 (d, J=6.0 Hz, 2H), 2.76-2.73 (m, 2H), 1.67-1.64 (m, 2H), 1.17 (s, 6H). $^{13}$C NMR (101 MHz, CDCl$_3$) δ 150.93, 146.29, 129.18, 123.75, 49.61, 46.36, 31.20, 30.54. HRMS (ESI-MS): calcd. 209.1290 [M+H]+ Found: 209.1271.

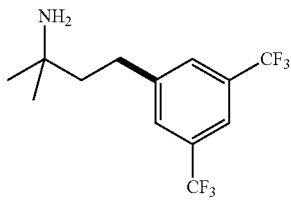

4-[3,5-Bis(trifluoromethyl)phenyl]-2-methylbutan-2-amine (1k)

Reaction time 12 h, purified by DCM/MeOH/NH$_4$OH (100:5:1). Product recovered as a white solid (48.5 mg, 54% yield). Rf=0.34 (DCM/MeOH=4/1). $^1$H NMR (400 MHz, CDCl$_3$) δ 7.69 (s, 1H), 7.63 (s, 2H), 2.81-2.77 (m, 2H), 1.70-1.66 (m, 2H), 1.19 (s, 6H). $^{13}$C NMR (101 MHz, CDCl$_3$) δ 145.29, 131.68 (q, J=22 Hz), 128.63 (d, J=2.0 Hz), 123.55 (q, J=180 Hz), 119.97 (quint, J=3.0 Hz), 49.70, 46.50, 31.00, 30.54. 19F NMR (376 MHz, CDCl$_3$) δ −61.22. HRMS (ESI-MS): calcd. 300.1188 [M+H]+ Found: 300.1180.

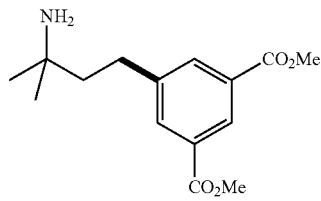

Dimethyl 5-(3-amino-3-methylbutyl)isophthalate (1l)

Reaction time 13 h, purified by DCM/MeOH/NH$_4$OH (100:3:1). Product recovered as a colorless oil (53.6 mg, 64% yield). Rf=0.27 (DCM/MeOH=4/1). $^1$H NMR (400 MHz, CDCl$_3$) δ 8.48 (s, 1H), 8.05 (s, 2H), 3.92 (s, 6H), 2.76-2.72 (m, 2H), 1.70-1.65 (m, 2H), 1.17 (s, 6H). $^{13}$C NMR (101 MHz, CDCl$_3$) δ 166.49, 143.78, 133.86, 130.70, 128.34, 52.46 49.67, 46.86, 30.89, 30.50. HRMS (ESI-MS): calcd. 280.1550 [M+H]+ Found: 280.1542.

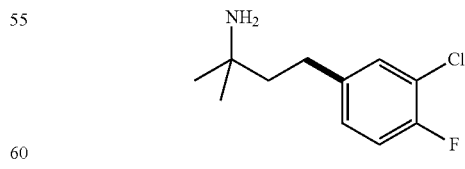

4-(3-Chloro-4-fluorophenyl)-2-methylbutan-2-amine (1m)

Reaction time 13 h, purified by DCM/MeOH/NH$_4$OH (100:4:1). Product was recovered as a colorless oil (39.5 mg, 61% yield). Rf=0.3 (DCM/MeOH=4/1). $^1$H NMR (400 MHz, CDCl$_3$) δ 7.20 (d, J=8.0 Hz, 1H), 7.02 (d, J=8.0 Hz, 2H), 2.62-2.57 (m, 2H), 1.64-1.59 (m, 2H), 1.15 (s, 6H). $^{13}$C NMR (101 MHz, CDCl3) δ 156.44 (d, J=244 Hz), 139.80 (d, J=4.0 Hz), 130.27, 127.94 (d, J=7.0 Hz), 120.55 (d, J=17 Hz), 116.40 (d, J=21 Hz), 49.56, 46.91, 30.55, 30.25. $^{19}$F NMR (376 MHz, CDCl$_3$) δ −118.70. HRMS (ESI-MS): calcd. 216.0949 [M+H]+ Found: 216.0944.

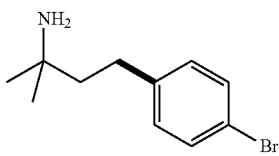

4-(4-Bromophenyl)-2-methylbutan-2-amine (1n)

Reaction time 12 h, purified by DCM/MeOH/NH$_4$OH (100:2:1). Product was recovered as a yellow oil (52.3 mg, 72% yield). Rf=0.29 (DCM/MeOH=4/1). $^1$H NMR (400 MHz, CDCl$_3$) δ 7.38 (d, J=8.0 Hz, 2H), 7.06 (d, J=8.0 Hz, 2H), 2.62-2.58 (m, 2H), 1.65-1.60 (m, 2H), 1.15 (s, 6H). $^{13}$C NMR (101 MHz, CDCl$_3$) δ 141.85, 131.56, 131.45, 130.24, 130.15, 119.46, 49.60, 46.96, 30.58, 30.54. HRMS (ESI-MS): calcd. 242.0545 [M+H]+ Found: 242.0540.

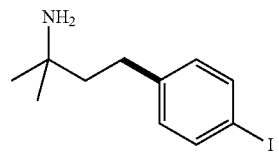

4-(4-Iodophenyl)-2-methylbutan-2-amine (1o)

Reaction time 13 h, purified by DCM/MeOH/NH$_4$OH (95:5:1). Product was recovered as a colorless oil (58.9 mg, 68% yield). Rf=0.35 (DCM/MeOH=4/1). $^1$H NMR (400 MHz, CDCl$_3$) δ 7.58 (d, J=8.0 Hz, 2H), 6.94 (d, J=8.0 Hz, 2H), 2.61-2.56 (m, 2H), 1.64-1.60 (m, 2H), 1.15 (s, 6H). $^{13}$C NMR (101 MHz, CDCl$_3$) δ 142.53, 137.47, 130.55, 128.40, 49.59, 46.96, 30.77, 30.58. HRMS (ESI-MS): calcd. 290.0406 [M+H]+ Found: 290.0404.

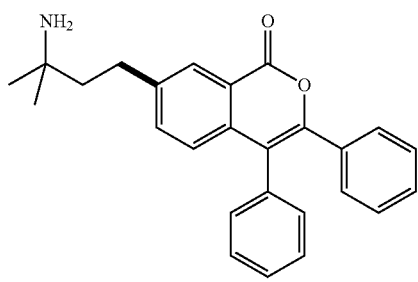

7-(3-Amino-3-methylbutyl)-3,4-diphenyl-H-isochromen-1-one (1p)

Reaction time 13 h, purified by DCM/MeOH/NH$_4$OH (96:4:1). Product was recovered as a white solid (35.7 mg, 31% yield). Rf=0.42 (DCM/MeOH=4/1). $^1$H NMR (400 MHz, CDCl$_3$) δ 8.20 (s, 1H), 7.47 (d, J=8.0 Hz, 1H), 7.41-7.40 (m, 3H), 7.31-7.30 (m, 2H), 7.25-7.24 (m, 2H), 7.22-7.21 (m, 1H), 7.18-7.16 (m, 2H), 7.10-7.09 (d, J=4.0 Hz, 1H), 2.81-2.78 (m, 2H), 1.81-1.78 (m, 2H), 1.27 (s, 6H). $^{13}$C NMR (101 MHz, CDCl$_3$) δ 162.62, 150.30, 143.33, 136.84, 135.41, 134.53, 133.04, 131.29, 129.27, 129.15, 128.93, 128.67, 128.19, 127.95, 125.66, 120.50, 117.00, 53.61, 46.34, 30.90, 29.87. HRMS (ESI-MS): calcd. 384.1964 [M+H]+ Found: 384.1960.

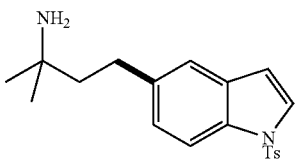

2-Methyl-4-(N-tosyl-1H-indol-5-yl)butan-2-amine (1q)

Reaction time 14 h, purified by DCM/MeOH/NH$_4$OH (95:5:1). Product was recovered as a yellow oil (42.8 mg, 40% yield). Rf=0.41 (DCM/MeOH=4/1). $^1$H NMR (400 MHz, CDCl$_3$) δ 7.87 (d, J=8.0 Hz, 1H), 7.74 (d, J=12 Hz, 2H), 7.51 (d, J=4.0 Hz, 1H), 7.32 (br, 1H), 7.20 (d, J=8.0 Hz, 2H), 7.14 (d, J=8.0 Hz, 1H), 6.57 (d, J=4.0 Hz, 1H), 2.71-2.67 (m, 2H), 2.32 (s, 3H), 1.68-1.64 (m, 2H), 1.16 (s, 6H). $^{13}$C NMR (101 MHz, CDCl$_3$) δ 144.94, 137.95, 135.41, 133.31, 131.13, 129.96, 126.91, 126.56, 125.40, 120.61, 113.46, 109.00, 53.58, 47.49, 31.00, 30.46, 21.69. HRMS (ESI-MS): calcd. 357.1637 [M+H]+ Found: 357.1642.

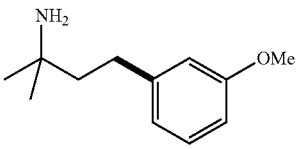

4-(3-Methoxyphenyl)-2-methylbutan-2-amine (1r)

Reaction time 14 h, purified by DCM/MeOH/NH$_4$OH (100:2:1). Product was recovered as a colorless oil (45.8 mg, 79% yield). Rf=0.22 (DCM/MeOH=4/1). $^1$H NMR (400 MHz, CDCl$_3$) δ 7.20 (t, J=8.0 Hz, 1H), 6.79 (d, J=8.0 Hz, 1H), 6.75-6.72 (m, 2H), 3.80 (s, 3H), 2.64-2.61 (m, 2H), 1.69-1.66 (m, 2H), 1.16 (s, 6H). $^{13}$C NMR (101 MHz, CDCl$_3$) δ 159.76, 144.56, 129.47, 120.83, 114.15, 111.11, 55.27, 49.66, 47.07, 31.29, 30.53. HRMS (ESI-MS): calcd. 194.1545 [M+H]+ Found: 194.1549.

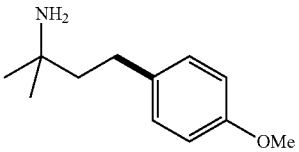

4-(4-Methoxyphenyl)-2-methylbutan-2-amine (1s)

Reaction time 12 h, purified by DCM/MeOH/NH$_4$OH (95:5:1). Product was recovered as a colorless oil (45.2 mg, 78% yield). Rf=0.21 (DCM/MeOH=4/1). $^1$H NMR (400 MHz, CDCl$_3$) δ 7.11 (d, J=8.0 Hz, 2H), 6.83 (d, J=8.0 Hz, 2H), 3.78 (m, 3H), 2.61-2.57 (m, 2H), 1.67-1.62 (m, 2H), 1.16 (s, 6H). $^{13}$C NMR (101 MHz, CDCl$_3$) δ 157.74, 134.88, 129.31, 129.18, 113.93, 113.87, 55.44, 49.68, 47.42, 30.49, 30.26. HRMS (ESI-MS): calcd. 194.1545 [M+H]+ Found: 194.1540.

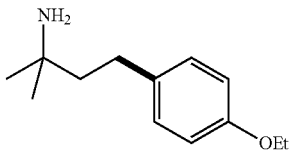

4-(4-Ethoxyphenyl)-2-methylbutan-2-amine (1t)

Reaction time 13 h, purified by DCM/MeOH/NH$_4$OH (100:5:1). Product was recovered as a yellow oil (44.8 mg, 72% yield). Rf=0.36 (DCM/MeOH=4/1). $^1$H NMR (400 MHz, CDCl$_3$) δ 7.09 (d, J=8.0 Hz, 2H), 6.81 (d, J=8.0 Hz, 2H), 4.00 (q, J=8.0 Hz, 2H), 2.60-2.56 (m, 2H), 1.66-1.62 (m, 2H), 1.39 (t, J=8.0 Hz, 3H), 1.15 (s, 6H). $^{13}$C NMR (101 MHz, CDCl$_3$) δ 157.09, 134.70, 129.21, 114.48, 63.48, 49.64, 47.36, 30.44, 30.22, 15.01. HRMS (ESI-MS): calcd. 208.1702 [M+H]+ Found: 208.1709.

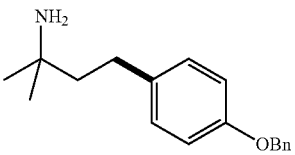

4-(4-Benzyloxyphenyl)-2-methylbutan-2-amine (1u)

Reaction time 14 h, purified by DCM/MeOH/NH$_4$OH (100:2:1). Product was recovered as a colorless oil (50.1 mg, 62% yield). Rf=0.34 (DCM/MeOH=4/1). $^1$H NMR (400 MHz, CDCl$_3$) δ 7.44-7.43 (m, 2H), 7.40-7.37 (m, 2H), 7.33-7.21 (m, 1H), 7.11 (d, J=4.0 Hz, 2H), 6.90 (d, J=4.0 Hz, 2H), 5.04 (s, 2H), 2.61-2.58 (m, 2H), 1.67-1.64 (m, 2H), 1.17 (s, 6H). $^{13}$C NMR (101 MHz, CDCl$_3$) δ 157.03, 137.31, 135.18, 129.30, 128.68, 128.02, 127.60, 114.89, 70.17, 49.71, 47.36, 30.47, 30.27. HRMS (ESI-MS): calcd. 270.1860 [M+H]+ Found: 270.1861.

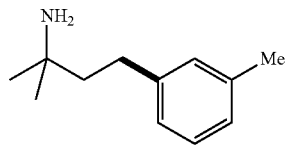

2-Methyl-4-(m-tolyl)butan-2-amine (1v)

Reaction time 12 h, purified by DCM/MeOH/NH$_4$OH (100:2:1). Product was recovered as a colorless oil (34.6 mg, 65% yield). Rf=0.30 (DCM/MeOH=4/1). $^1$H NMR (400 MHz, CDCl$_3$) δ 7.16-7.13 (m, 1H), 7.02-7.00 (m, 3H), 2.67-2.64 (m, 2H), 2.31 (s, 3H), 1.80-1.78 (m, 2H), 1.28 (s, 6H). $^{13}$C NMR (101 MHz, CDCl$_3$) δ 142.05, 138.09, 129.28, 128.45, 126.69, 125.46, 51.81, 45.57, 30.82, 28.71, 21.51. HRMS (ESI-MS): calcd. 178.1595 [M+H]+ Found: 178.1590.

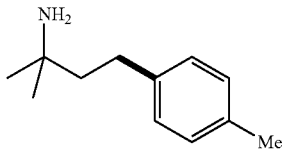

2-Methyl-4-(p-tolyl)butan-2-amine (1w)

Reaction time 12 h, purified by DCM/MeOH/NH$_4$OH (100:2:1). Product was recovered as a colorless oil (39.3 mg, 74% yield). Rf=0.27 (DCM/MeOH=4/1). $^1$H NMR (400 MHz, CDCl$_3$) δ 7.09 (s, 4H), 2.63-2.59 (m, 2H), 2.31 (s, 3H), 1.68-1.64 (m, 4H), 1.17 (s, 6H). $^{13}$C NMR (101 MHz, CDCl$_3$) δ 139.80, 135.24, 129.19, 128.29, 49.64, 47.41, 30.75, 30.53, 21.12. HRMS (ESI-MS): calcd. 178.1595 [M+H]+ Found: 178.1590.

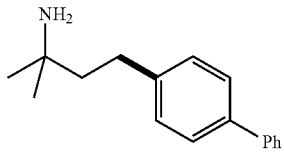

4-(1,1'-Biphenyl-4-yl)-2-methylbutan-2-amine (1x)

Reaction time 14 h, purified by DCM/MeOH/NH$_4$OH (95:5:1). Product was recovered as a gummy, colorless solid (48.8 mg, 68% yield). Rf=0.38 (DCM/MeOH=4/1). $^1$H NMR (400 MHz, CDCl$_3$) δ 7.59 (d, J=8.0 Hz, 2H), 7.53 (d, J=8.0 Hz, 2H), 7.43 (t, J=8.0 Hz, 2H), 7.33 (t, J=8.0 Hz, 1H), 7.28 (d, J=8.0 Hz, 2H), 2.73-2.68 (m, 2H), 1.74-1.70 (m, 2H), 1.20 (s, 6H). $^{13}$C NMR (101 MHz, CDCl$_3$) δ 142.04, 141.17, 138.77, 128.83, 128.82, 127.24, 127.10, 49.66, 47.21, 30.87, 30.61. HRMS (ESI-MS): calcd. 240.1753 [M+H]+ Found: 240.1757.

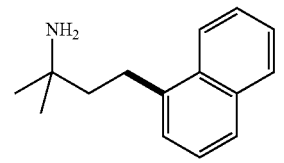

2-Methyl-4-(naphthalen-1-yl)butan-2-amine (1y)

Reaction time 14 h, purified by DCM/MeOH/NH$_4$OH (95:5:1). Product was recovered as a colorless oil (27.5 mg, 43% yield). Rf=0.33 (DCM/MeOH=4/1). $^1$H NMR (400 MHz, CDCl$_3$) δ 8.04 (d, J=8.0 Hz, 1H), 7.85 (d, J=8.0 Hz, 1H), 7.71 (d, J=8.0 Hz, 1H), 7.53-7.45 (m, 2H), 7.42-7.33 (m, 2H), 3.15-3.10 (m, 2H), 1.82-1.78 (m, 2H), 1.26 (m, 6H). $^{13}$C NMR (101 MHz, CDCl$_3$) δ 138.92, 133.99, 131.86, 128.92, 126.63, 125.90, 125.76, 125.55, 123.75, 50.01, 46.26, 30.41, 28.34. HRMS (ESI-MS): calcd. 214.1596 [M+H]+ Found: 214.1590.

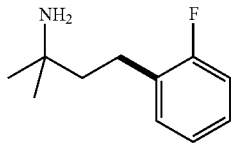

4-(2-Fluorophenyl)-2-methylbutan-2-amine (1z)

Reaction time 13 h, purified by DCM/MeOH/NH$_4$OH (100:2:1). Product was recovered as a colorless oil (25.5 mg, 47% yield). Rf=0.3 (DCM/MeOH=4/1). $^1$H NMR (400 MHz, CDCl$_3$) δ 7.17-7.15 (m, 1H), 7.13-7.10 (m, 1H), 7.01 (t, J=8.0 Hz, 1H), 6.96 (t, J=8.0 Hz, 1H), 2.66-2.63 (m, 2H), 1.64-1.61 (m, 2H), 1.14 (s, 6H). $^{13}$C NMR (101 MHz, CDCl$_3$) δ 161.15 (d, J=162 Hz), 130.49 (d, J=3.0 Hz), 129.63 (d, J=10 Hz), 127.48 (d, J=5.0 Hz), 124.08 (d, J=3.0 Hz), 115.28 (d, J=15 Hz), 49.70, 45.49, 30.27, 24.42. $^{19}$F NMR (376 MHz, CDCl$_3$) δ −126.65. HRMS (ESI-MS): calcd. 182.1345 [M+H]+ Found: 182.1340.

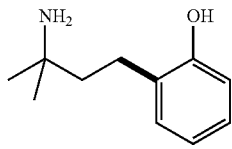

2-(3-Amino-3-methylbutyl)phenol (1aa)

Reaction time 14 h, purified by DCM/MeOH/NH$_4$OH (100:5:1). Product was recovered as a yellow oil (30.6 mg, 57% yield). Rf=0.16 (DCM/MeOH=4/1). $^1$H NMR (400 MHz, CDCl$_3$) δ 7.11-7.06 (m, 2H), 6.86-6.78 (m, 2H), 2.70-2.68 (m, 2H), 1.77-1.74 (m, 2H), 1.14 (s, 6H). $^{13}$C NMR (101 MHz, CDCl$_3$) δ. 155.53, 130.52, 130.37, 127.53, 119.89, 117.94, 50.04, 43.67, 31.43, 25.99. HRMS (ESI-MS): calcd. 180.1390 [M+H]+ Found: 180.1392.

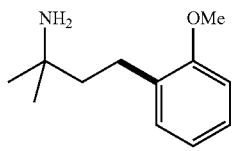

4-(2-Methoxyphenyl)-2-methylbutan-2-amine (1ab)

Reaction time 13 h, purified by DCM/MeOH/NH$_4$OH (100:5:1). Product was recovered as a colorless oil (23.8 mg, 41% yield). Rf=0.21 (DCM/MeOH=4/1). $^1$H NMR (400 MHz, CDCl$_3$) δ 7.18-7.14 (m, 2H), 6.88 (t, J=6.0 Hz, 1H), 6.84 (d, J=6.0 Hz, 1H), 3.82 (s, 3H), 2.66-2.63 (m, 2H), 1.64-1.61 (m, 2H), 1.17 (s, 6H). $^{13}$C NMR (101 MHz, CDCl3) δ 157.41, 131.23, 129.64, 127.02, 120.54, 110.30, 55.36, 49.81, 45.27, 30.30, 25.49. HRMS (ESI-MS): calcd. 194.1550 [M+H]+ Found: 194.1555.

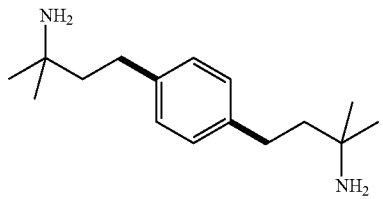

Synthesis of 4,4'-(1,4-Phenylene)bis(2-methylbutan-2-amine) (1ac)

A 7.5 mL vial was charged with Pd(OAc)$_2$ (6.7 mg, 0.03 mmol, 0.10 equiv), silver trifluoroacetate (132.5 mg, 0.60 mmol, 2.0 equiv), 1,4-diiodobenzene (98.9 mg, 0.30 mmol, 1.0 equiv), amine (78.4 mg, 0.90 mmol, 3.0 equiv), acetic acid (1.0 mL), and water (21.7 µL, 12.1 mmol, 4.0 equiv) followed by the addition of dry ice as the CO$_2$ source. The vial was immediately sealed with a PTFE lined cap and stirred at room temperature for 15 min. After 15 min of stirring, the reaction vial was heated in a pie-block at 110° C. under stirring for between 13 h. After cooling to room temperature, the reaction mixture was concentrated in vacuo. Aq. HCl (10 mL, 1.2 M) was added to the residual reaction mass and stirred for 15 min. The mixture was extracted with ether (8.0 mL) and the organic layer was discarded. The aqueous layer was made basic with ammonium hydroxide solution up to pH=8, followed by extraction with dichloromethane (2×10 mL). The organic layer was washed with water (5.0 mL), followed by brine, and dried over Na$_2$SO$_4$. The filtrate was concentrated under vacuo and further purified by flash column chromatography over silica (DCM/MeOH/NH$_4$OH=92:8:1) to give the C—H arylation product. Product was recovered as a colorless oil (30.5 mg, 41% yield). Rf=0.16 (DCM/MeOH=4:1). $^1$H NMR (400 MHz, CDCl$_3$) δ 7.11 (s, 4H), 2.62-2.60 (m, 4H), 1.67-1.64 (m, 4H), 1.16 (s, 12H). $^{13}$C NMR (101 MHz, CDCl$_3$) δ 140.15, 128.42, 49.67, 47.30, 30.76, 30.51. HRMS (ESI-MS): calcd. 249.2331 [M+H]+ Found: 249.2327.

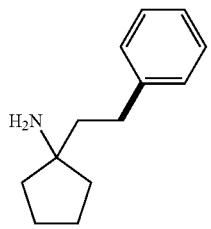

1-Phenethylcyclopentanamine (2a)

Reaction time 14 h, purified by DCM/MeOH/NH$_4$OH (100:3:1). Product was recovered as a colorless oil (32.4 mg, 57% yield). Rf=0.24 (DCM/MeOH=4.5/0.5). $^1$H NMR (400 MHz, CDCl$_3$) δ 7.30-7.27 (m, 2H), 7.22-7.16 (m, 3H), 2.73-2.69 (m, 2H), 1.85-1.76 (m, 4H), 1.70-1.57 (m, 4H), 1.53-1.47 (m, 2H). $^{13}$C NMR (101 MHz, CDCl$_3$) δ 142.92, 128.42, 128.35, 125.70, 61.27, 45.16, 40.66, 31.57, 24.02. HRMS (ESI-MS): calcd. 190.1596 [M+H]+ Found: 190.1593.

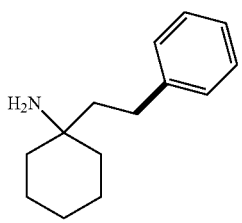

1-Phenethylcyclohexanamine (2b)

Reaction time 13 h, purified by DCM/MeOH/NH$_4$OH (100:3:1). Product was recovered as a colorless oil (37.8 mg, 62% yield). Rf=0.23 (DCM/MeOH=4.5/0.5). $^1$H NMR (400 MHz, CDCl$_3$) δ 7.25-7.23 (m, 2H), 7.18-7.13 (m, 3H), 2.63-2.60 (m, 2H), 1.65-1.62 (m, 2H), 1.50-1.44 (m, 7H), 1.38-1.32 (m, 3H). $^{13}$C NMR (101 MHz, CDCl$_3$) δ 143.24, 128.50, 125.76, 50.77, 38.90, 29.67, 26.14, 22.40. HRMS (ESI-MS): calcd. 204.1753 [M+H]+ Found: 204.1757.

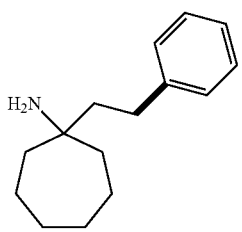

1-Phenethylcycloheptanamine (2c)

Reaction time 12 h, purified by DCM/MeOH/NH$_4$OH (100:3:1). Product was recovered as a colorless oil (41.7 mg, 64% yield). Rf=0.22 (DCM/MeOH=4.5/0.5). $^1$H NMR (400 MHz, CDCl$_3$) δ 7.25-7.23 (m, 2H), 7.18-7.14 (m, 3H), 2.64-2.61 (m, 2H), 1.66-1.61 (m, 4H), 1.55-1.47 (m, 8H), 1.44-1.41 (m, 2H), 1.28 (br, 2H). $^{13}$C NMR (101 MHz, CDCl$_3$) δ 143.17, 128.55, 128.43, 125.70, 54.63, 46.40, 42.18, 30.35, 30.23, 22.87. HRMS (ESI-MS): calcd. 218.1909 [M+H]+ Found: 218.1906.

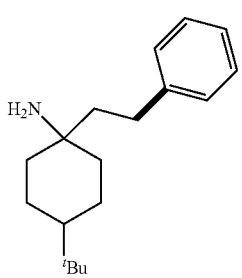

4-(tert-Butyl)-1-phenethylcyclohexanamine (2d)

Reaction time 24 h, purified by DCM/MeOH/NH$_4$OH (100:5:1). Product was recovered as a colorless oil (41.2 mg, 53% yield). Rf=0.24 (DCM/MeOH=4/1). $^1$H NMR (400 MHz, CDCl$_3$) δ 7.30-7.26 (m, 2H), 7.22-7.16 (m, 3H), 2.74-2.70 (m, 2H), 1.78-1.71 (m, 4H), 1.64-1.61 (m, 2H), 1.41-1.29 (m, 5H), 0.89 (s, 9H). $^{13}$C NMR (101 MHz, CDCl$_3$) δ 142.98, 128.50, 128.47, 125.79, 70.79, 48.11, 46.33, 37.64, 32.58, 29.79, 27.74, 22.64. HRMS (ESI-MS): calcd. 260.2379 [M+H]+ Found: 260.2374.

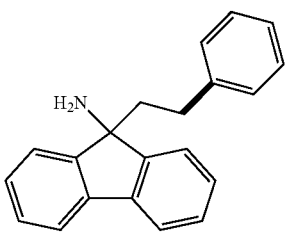

9-Phenethyl-9H-fluoren-9-amine (2e)

Reaction time 12 h, purified by DCM/MeOH/NH$_4$OH (95:2:1). Product was recovered as a colorless oil (50.5 mg, 59% yield). Rf=0.43 (Hex/EA=1/1). $^1$H NMR (400 MHz, CDCl$_3$) δ 7.71-7.69 (m, 2H), 7.54-7.52 (m, 2H), 7.40-7.35 (m, 4H), 7.20-7.17 (m, 2H), 7.13-7.11 (m, 1H), 6.98 (d, J=8.0 Hz, 2H), 2.41-2.37 (m, 2H), 2.10-2.06 (m, 2H), 1.98 (br, 2H, NH$_2$). $^{13}$C NMR (101 MHz, CDCl$_3$) δ 150.55, 142.08, 139.80, 128.30, 128.21, 128.02, 125.74, 123.00, 120.13, 65.53, 42.93, 30.72. HRMS (ESI-MS): calcd. 286.1596 [M+H]+ Found: 286.1592.

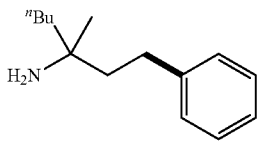

3-Methyl-1-phenylheptan-3-amine (2f)

Reaction time 12 h, purified by DCM/MeOH/NH$_4$OH (100:3:1). Product was recovered as a colorless oil (41.3 mg, 67% yield). Rf=0.28 (DCM/MeOH=4.5/0.5). $^1$H NMR (400 MHz, CDCl$_3$) δ 7.27-7.23 (m, 2H), 7.18-7.14 (m, 3H), 2.61-2.58 (m, 2H), 1.63-1.61 (m, 2H), 1.38-1.29 (m, 6H), 1.09 (s, 3H), 0.90 (t, J=4.0 Hz, 3H). $^{13}$C NMR (101 MHz, CDCl$_3$) δ 143.01, 128.49, 128.42, 125.78, 51.56, 44.95, 42.75, 30.72, 28.25, 26.36, 23.53, 14.31. HRMS (ESI-MS): calcd. 206.1910 [M+H]+ Found: 209.1916.

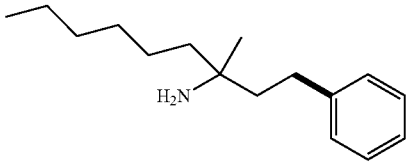

3-Methyl-1-phenylnonan-3-amine (2g)

Reaction time 14 h, purified by DCM/MeOH/NH$_4$OH (100:5:1). Product was recovered as a colorless oil (44.1 mg, 63% yield). Rf=0.24 (DCM/MeOH=4.5/0.5). $^1$H NMR (400 MHz, CDCl$_3$) δ 7.30-7.26 (m, 2H), 7.20-7.16 (m, 3H), 2.64-2.60 (m, 2H), 1.66-1.62 (m, 2H), 1.30 (br, 10H), 1.11

(s, 3H), 0.89 (t, J=8.0 Hz, 3H). $^{13}$C NMR (101 MHz, CDCl$_3$) δ 143.00, 128.48, 128.42, 125.77, 51.60, 44.96, 43.06, 32.04, 30.75, 30.16, 28.27, 24.12, 22.81, 14.27. HRMS (ESI-MS): calcd. 234.2222 [M+H]+ Found: 234.2221.

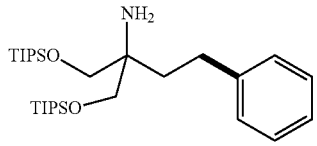

2-Amino-2-phenethylpropane-1,3-diol (2h)

Reaction time 14 h, purified by DCM/MeOH/NH$_4$OH (100:5:1). Product was recovered as a colorless oil (51.8 mg, 34% yield). Rf=0.45 (DCM/MeOH=4/1). $^1$H NMR (400 MHz, CDCl$_3$) δ 7.29-7.27 (m, 2H), 7.20-7.18 (m, 3H), 3.68 (d, J=8.0 Hz, 1H), 3.63-3.56 (m, 2H), 3.45 (d, J=12 Hz, 1H), 2.67-2.63 (m, 2H), 1.74-1.69 (m, 2H), 1.14-1.05 (m, 42H). $^{13}$C NMR (101 MHz, CDCl$_3$) δ 128.56, 128.39, 125.96, 69.03, 67.69, 37.68, 29.88, 18.18, 11.99. HRMS (ESI-MS): calcd. 508.4007 [M+H]+ Found: 508.3997.

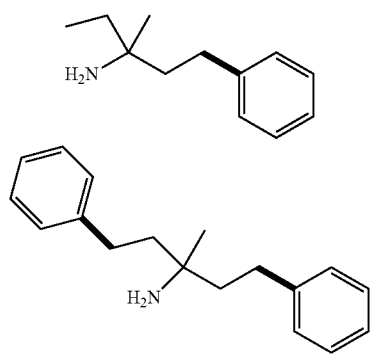

3-Methyl-1-phenylpentan-3-amine (2i-mono) and 3-methyl-1,5-diphenylpentan-3-amine (2i-di)

Reaction time 12 h, purified by DCM/MeOH/NH$_4$OH (100:2:1). Products were recovered as a colorless oil (isolated as inseparable mixture of mono and bis-arylated product in the ratio of 1:1.6, 41.4 mg, 62% yield). Rf=0.3 (DCM/MeOH=4/1). $^1$H NMR (400 MHz, CDCl$_3$) for 2i-mono δ 7.31-7.27 (m, 2H), 7.22-7.17 (m, 3H), 2.64-2.61 (m, 2H), 1.66-1.63 (m, 2H), 1.47-1.46 (m, 2H), 1.11 (s, 3H), 0.92 (t, J=4.0 Hz, 3H). $^1$H NMR (400 MHz, CDCl$_3$) for 2i-di δ 7.31-7.27 (m, 4H), 7.22-7.17 (m, 6H), 2.69-2.66 (m, 4H), 1.75-1.73 (m, 4H), 1.21 (s, 3H). $^{13}$C NMR (101 MHz, CDCl$_3$) δ 142.99, 142.76, 128.55, 128.49, 128.43, 125.88, 125.79, 51.77, 45.09, 44.40, 35.25, 30.77, 30.70, 28.22, 27.63, 8.46. HRMS (ESI-MS): calcd. 178.1596 (2i-mono), 254.1909 (2i-di) [M+H]+ Found: 178.1591 (2i-mono), 254.1902 (2i-di).

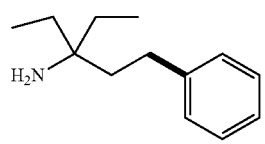

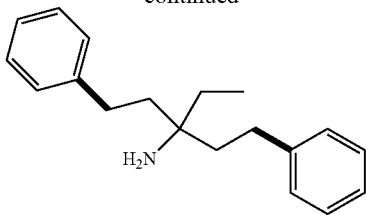

3-Ethyl-1-phenylpentan-3-amine (2j-mono) and 3-ethyl-1,5-diphenylpentan-3-amine (2j-di)

Reaction time 12 h, Purified by DCM/MeOH/NH$_4$OH (100:5:1). Products were recovered as a colorless oil (isolated as inseparable mixture of mono and bis-arylated product in the ratio of 1:1.5, 36.7 mg, 53% yield). Rf=0.3 (Hex/EA/DCM=5:1:2). $^1$H NMR (400 MHz, CDCl$_3$) for 2j-mono δ 7.31-7.28 (m, 2H), 7.22-7.16 (m, 3H), 2.60-2.56 (m, 2H), 1.63-1.59 (m, 2H), 1.46-1.41 (m, 4H), 0.88 (t, J=8.0 Hz, 6H). $^1$H NMR (400 MHz, CDCl$_3$) for 2j-di δ 7.31-7.28 (m, 4H), 7.22-7.16 (m, 6H), 2.66-2.61 (m, 4H), 1.73-1.68 (m, 4H), 1.53 (q, J=8.0 Hz, 2H), 0.94 (t, J=8.0 Hz, 3H). $^{13}$C NMR (101 MHz, CDCl$_3$) δ 143.14, 142.89, 128.57, 128.51, 128.46, 128.44, 125.90, 125.80, 59.06, 53.58, 42.00, 41.58, 32.50, 31.92, 30.28, 30.23, 8.03, 7.97. HRMS (ESI-MS): calcd. 192.1753 (2j-mono), 268.2066 (2j-di) [M+H]+ Found: 192.1758 (2j-mono), 268.2060 (2j-di).

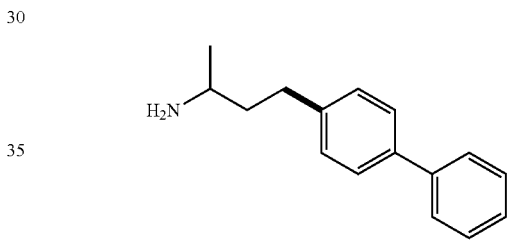

4-(1,1'-Biphenyl-4-yl)butan-2-amine (2k)

Reaction time 14 h, purified by DCM/MeOH/NH$_4$OH (95:5:1). Product was recovered as a colorless oil (41.2 mg, 61% yield). Rf=0.3 (DCM/MeOH=4.5:0.5). $^1$H NMR (400 MHz, CDCl$_3$) δ 7.58 (d, J=8.0 Hz, 2H), 7.52 (d, J=8.0 Hz, 2H), 7.43 (d, J=8.0 Hz, 2H), 7.32 (t, J=8.0 Hz, 1H), 7.27 (m, 2H), 2.98-2.94 (m, 1H), 2.74-2.64 (m, 2H), 1.73-1.66 (m, 2H), 1.13 (d, J=4.0 Hz, 3H). $^{13}$C NMR (101 MHz, CDCl$_3$) δ 141.56, 141.19, 138.86, 128.89, 128.85, 127.25, 127.15, 127.12, 46.72, 41.89, 32.60, 24.16. HRMS (ESI-MS): calcd. 226.1596 [M+H]+ Found: 226.1590.

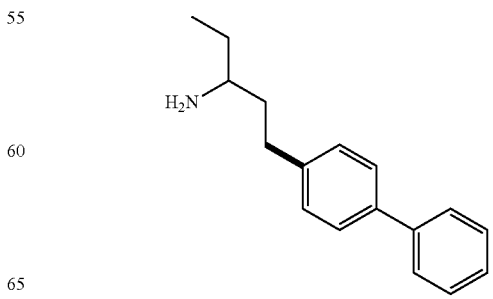

1-(1,1'-Biphenyl-4-yl)pentan-3-amine (2l)

Reaction time 14 h, purified by DCM/MeOH/NH$_4$OH (95:5:1). Product was recovered as a colorless oil (41.6 mg, 58% yield). Rf=0.21 (DCM/MeOH=4.5/0.5). $^1$H NMR (400 MHz, CDCl$_3$) δ 7.61-7.57 (m, 2H), 7.52 (d, J=8.0 Hz, 2H), 7.45-7.41 (m, 3H), 7.34-7.33 (m, 1H), 7.27-7.26 (m, 1H), 2.83-2.76 (m, 1H), 2.71-2.64 (m, 2H), 1.99-1.76 (m, 3H), 1.65-1.52 (m, 2H), 1.40-1.33 (m, 1H), 0.95 (t, J=8.0 Hz, 3H). $^{13}$C NMR (101 MHz, CDCl$_3$) δ 141.57, 141.18, 138.85, 128.89, 128.84, 127.24, 127.14, 127.12, 46.71, 41.94, 32.61, 31.11, 24.20. HRMS (ESI-MS): calcd. 240.1753 [M+H]+ Found: 240.1753.

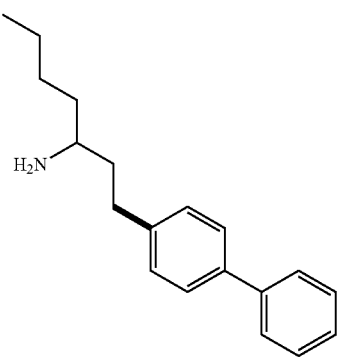

1-(1,1'-Biphenyl-4-yl)heptan-3-amine (2m)

Reaction time 13 h, purified by DCM/MeOH/NH$_4$OH (95:5:1). Product was recovered as a colorless oil (38.5 mg, 48% yield). Rf=0.26 (DCM/MeOH=4/1). $^1$H NMR (400 MHz, CDCl$_3$) δ 7.52 (d, J=4.0 Hz, 2H), 7.45 (d, J=8.0 Hz, 2H), 7.39 (t, J=8.0 Hz, 2H), 7.32 (d, J=8.0 Hz, 1H), 7.27-7.26 (m, 2H), 3.18-3.15 (m, 1H), 2.88-2.75 (m, 2H), 2.02 (br, 2H), 1.74-1.71 (m, 2H), 1.41-1.25 (m, 4H), 0.85 (t, J=8.0 Hz, 3H). $^{13}$C NMR (101 MHz, CDCl$_3$) δ 141.12, 140.85, 138.98, 128.93, 128.83, 127.28, 127.14, 127.10, 51.49, 37.82, 35.92, 31.92, 28.08, 22.79, 14.17. HRMS (ESI-MS): calcd. 268.2066 [M+H]+ Found: 268.2060.

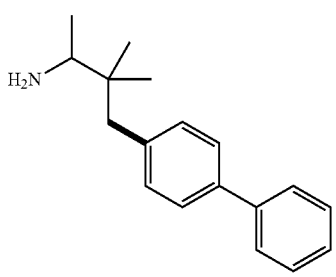

4-(1,1'-Biphenyl-4-yl)-3,3-dimethylbutan-2-amine (2n)

Reaction time 14 h, purified by DCM/MeOH/NH$_4$OH (100:4:1). Product was recovered as a colorless oil (39.5 mg, 52% yield). Rf=0.3 (DCM/MeOH=4/1). $^1$H NMR (400 MHz, CDCl$_3$) δ 7.59 (d, J=8.0 Hz, 2H), 7.50 (d, J=8.0 Hz, 2H), 7.43 (d, J=8.0 Hz, 2H), 7.32 (t, J=8.0 Hz, 1H), 7.22 (d, J=8.0 Hz, 2H), 2.80-2.75 (m, 1H), 2.69-2.55 (m, 2H), 1.12 (d, J=8.0 Hz, 2H), 0.88 (s, 3H), 0.85 (s, 3H). $^{13}$C NMR (101 MHz, CDCl$_3$) δ 141.14, 138.83, 131.25, 128.85, 127.15, 127.10, 126.55, 54.62, 53.60, 44.36, 29.85, 23.30, 22.69. HRMS (ESI-MS): calcd. 254.1909 [M+H]+ Found: 254.1904.

Optimization and Synthesis of γ-Arylated 2° Amines

Catalytic C(Sp$^3$)-H Arylation of Secondary Amines

FIG. 7 shows the optimization of γ-arylated 2° amines. Standard conditions: A 15 mL sealed tube was charged with Pd(OAc)$_2$ (6.7 mg, 0.03 mmol, 0.10 equiv), silver trifluoroacetate (132.5 mg, 0.60 mmol, 2.0 equiv), phenyl iodide (183.6 mg, 0.90 mmol, 3.0 equiv), N-benzyl-2-methylbutan-2-amine (53.2 mg, 0.30 mmol, 1.0 equiv), HFIP (0.9 mL), acetic acid (0.1 mL), and water (21.7 μL, 1.2 mmol, 4.0 equiv) followed by the addition of dry ice (50 equiv) as the CO$_2$ source. The tube was sealed with a PTFE lined cap and stirred at room temperature for 15 min. After 15 min of stirring, the reaction mass was heated in sand bath at 90° C. under stirring for 12-14 h. After cooling to room temperature, the reaction mixture was concentrated in vacuo. Aq. HCl (10 mL, 1.2 M) was added to the residual reaction mass and stirred for 15 min. The mixture was extracted with ether (8.0 mL) and the organic layer was discarded. The aqueous layer was made basic with ammonium hydroxide solution up to pH=8, followed by extraction with dichloromethane (2×10 mL). The organic layer was washed with water (5.0 mL), followed by brine, and dried over Na$_2$SO$_4$. The filtrate was concentrated under vacuo and further purified by flash column chromatography over silica (DCM/MeOH/NH$_4$OH) to give the C—H arylation product.

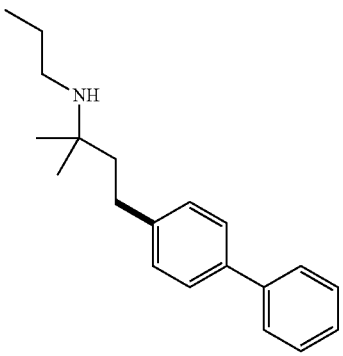

4-(1,1'-Biphenyl-4-yl)-2-methyl-N-propylbutan-2-amine (3a)

Reaction time 14 h, purified by DCM/MeOH (97:3). Product was recovered as a colorless oil (30.4 mg, 36% yield). Rf=0.24 (DCM/MeOH=4.5:0.5). $^1$H NMR (400 MHz, CDCl$_3$) δ 7.59-7.57 (m, 2H), 7.51 (d, J=4.0 Hz, 2H), 7.43 (t, J=8.0 Hz, 2H), 7.34-7.33 (m, 1H), 7.28-7.26 (m, 2H), 2.65-2.61 (m, 2H), 2.52 (t, J=8.0 Hz, 2H), 1.75-1.71 (m, 2H), 1.49 (q, J=8.0 Hz, 2H), 1.15 (s, 6H), 0.95 (t, J=8.0 Hz, 3H). $^{13}$C NMR (101 MHz, CDCl$_3$) δ 142.29, 141.24, 138.79, 128.85, 127.26, 127.13, 44.17, 42.75, 30.36, 27.43, 24.30, 12.23. HRMS (ESI-MS): calcd. 282.2222 [M+H]+ Found: 282.2217.

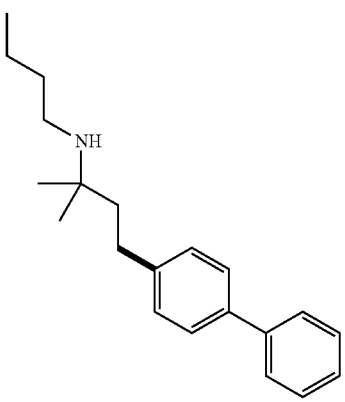

N-[4-(1,1'-Biphenyl-4-yl)-2-methylbutan-2-yl]butan-1-amine (3b)

Reaction time 13 h, purified by DCM/MeOH (97:3). Product was recovered as a colorless oil (34.6 mg, 39% yield). Rf=0.27 (DCM/MeOH=4.5:0.5). $^1$H NMR (400 MHz, CDCl$_3$) δ 7.55 (d, J=8.0 Hz, 2H), 7.50 (d, J=4.0 Hz, 2H), 7.43-7.40 (m, 2H), 7.32 (t, J=4.0 Hz, 1H), 7.26-7.25 (m, 2H), 2.87-2.84 (m, 2H), 2.73-2.70 (m, 2H), 2.08-2.05 (m, 2H), 1.97-1.93 (m, 2H), 1.49 (s, 6H), 1.34-1.30 (m, 2H), 0.88 (d, J=6.0 Hz, 3H). $^{13}$C NMR (101 MHz, CDCl$_3$) δ 140.99, 139.94, 139.31, 128.90, 128.87, 127.39, 127.25, 127.10, 59.51, 41.67, 40.15, 29.97, 28.82, 23.78, 20.56, 13.74. HRMS (ESI-MS): calcd. 296.2379 [M+H]+ Found: 296.2378.

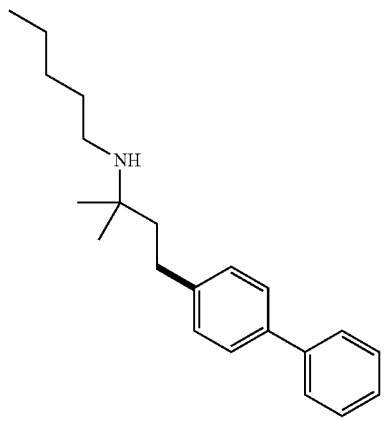

N-[4-(1,1'-Biphenyl-4-yl)-2-methylbutan-2-yl]pentan-1-amine (3c)

Reaction time 12 h, purified by DCM:MeOH (95:5). Product was recovered as a colorless oil (34.3 mg, 37% yield). Rf=0.29 (DCM/MeOH=4.5:0.5). $^1$H NMR (400 MHz, CDCl$_3$) δ 7.57-7.55 (m, 2H), 7.52-7.50 (m, 2H), 7.44-7.40 (m, 2H), 7.35-7.31 (m, 1H), 7.27-7.25 (m, 3H), 2.87-2.82 (m, 2H), 2.74-2.70 (m, 2H), 2.07-2.03 (m, 2H), 1.96 (br, 2H), 1.49 (s, 6H), 1.29-1.25 (m, 4H), 0.86 (t, J=8.0 Hz, 3H). $^{13}$C NMR (101 MHz, CDCl$_3$) δ 140.98, 140.01, 139.28, 128.89, 128.86, 127.38, 127.25, 127.10, 59.29, 41.89, 40.18, 29.96, 29.42, 26.74, 23.97, 22.31, 14.14. HRMS (ESI-MS): calcd. 310.2536 [M+H]+ Found: 310.2525.

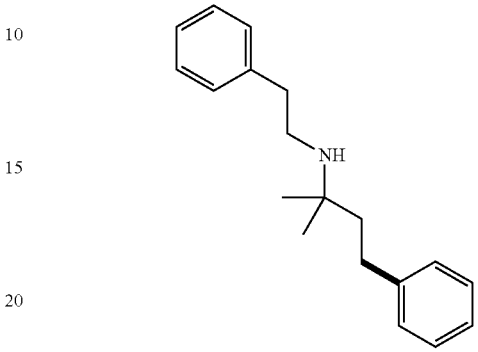

2-Methyl-N-phenethyl-4-phenylbutan-2-amine (3d)

Reaction time 13 h, purified by DCM:MeOH (97:3). Product was recovered as a colorless oil (27.3 mg, 34% yield). Rf=0.25 (DCM/MeOH=4.5:0.5). $^1$H NMR (400 MHz, CDCl$_3$) δ 7.32-7.27 (m, 3H), 7.25-7.20 (m, 4H), 7.18-7.13 (m, 3H), 2.90 (br, 4H), 2.53-2.49 (m, 2H), 1.78-1.74 (m, 2H), 1.21 (s, 6H). 13C NMR (101 MHz, CDCl$_3$) δ 142.41, 139.55, 128.86, 128.67, 128.51, 128.38, 126.52, 125.91, 53.59, 43.66, 42.05, 36.24, 30.47, 26.49. HRMS (ESI-MS): calcd. 268.2066 [M+H]+ Found: 268.2062.

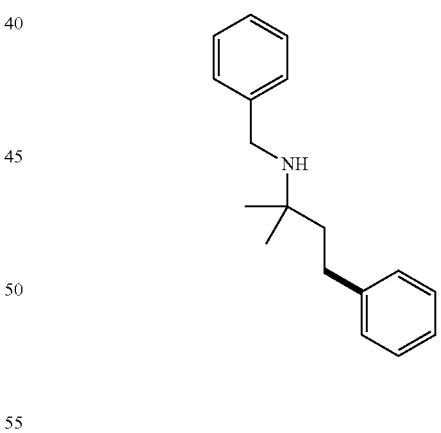

N-Benzyl-2-methyl-4-phenylbutan-2-amine (3e)

Reaction time 14 h, purified by DCM:MeOH (98:2). Product was recovered as a colorless oil (31.2 mg, 41% yield). Rf=0.4 (DCM/MeOH=4.5:0.5). $^1$H NMR (400 MHz, CDCl$_3$) δ 7.38-7.34 (m, 3H), 7.33-7.29 (m, 3H), 7.28-7.27 (m, 1H), 7.22-7.17 (m, 3H), 3.73 (s, 2H), 2.69-2.64 (m, 2H), 1.80-1.75 (m, 2H), 1.21 (s, 6H). $^{13}$C NMR (101 MHz, CDCl$_3$) δ 143.17, 141.49, 128.57, 128.52, 128.46, 128.42, 126.95, 125.79, 52.87, 46.88, 42.93, 30.75, 27.54. HRMS (ESI-MS): calcd. 254.1902 [M+H]+ Found: 254.1903.

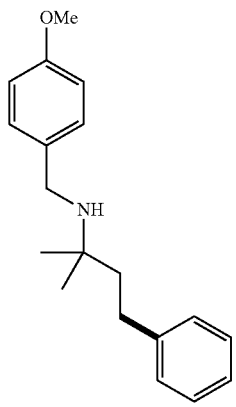

N-(4-Methoxybenzyl)-2-methyl-4-phenylbutan-2-amine (3f)

Reaction time 14 h, purified by DCM:MeOH (95:5). Product was recovered as a colorless oil (38.3 mg, 45% yield). Rf=0.3 (DCM/MeOH=4.5:0.5). $^1$H NMR (400 MHz, CDCl$_3$) δ 7.31-7.30 (m, 2H), 7.25-7.23 (m, 2H), 7.16-7.14 (m, 3H), 6.83 (d, J=4.0 Hz, 2H), 3.72 (s, 3H), 3.66 (s, 2H), 2.64-2.61 (m, 2H), 1.80-1.77 (m, 2H), 1.21 (s, 6H). $^{13}$C NMR (101 MHz, CDCl$_3$) δ 158.97, 142.62, 130.20, 128.51, 128.45, 128.43, 125.88, 114.00, 55.39, 46.05, 42.24, 30.61, 26.77. HRMS (ESI-MS): calcd. 284.2015 [M+H]+ Found: 284.2016.

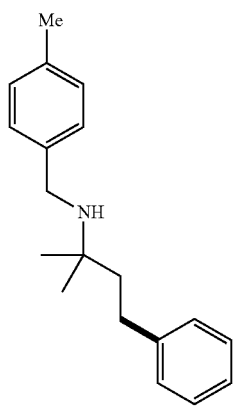

2-Methyl-N-(4-methylbenzyl)-4-phenylbutan-2-amine (3h)

Reaction time 12 h, purified by DCM:MeOH (97:3). Product was recovered as a colorless oil (30.5 mg, 38% yield). Rf=0.5 (DCM/MeOH=4.5:0.5). $^1$H NMR (400 MHz, CDCl$_3$) δ 7.32-7.31 (m, 2H), 7.29-7.28 (m, 2H), 7.23-7.20 (m, 3H), 7.16-7.14 (m, 2H), 3.70 (s, 2H), 2.69-2.65 (m, 2H), 2.35 (s, 3H), 1.80-1.76 (m, 2H), 1.22 (s, 6H). $^{13}$C NMR (101 MHz, CDCl$_3$) δ 143.18, 138.44, 136.45, 129.20, 128.48, 128.43, 128.33, 125.74, 52.80, 46.58, 42.92, 30.74, 27.55, 21.24. HRMS (ESI-MS): calcd. 268.2066 [M+H]+ Found: 268.2067.

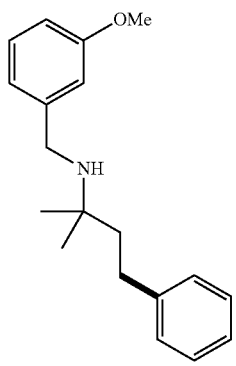

N-(3-Methoxybenzyl)-2-methyl-4-phenylbutan-2-amine (3g)

Reaction time 13 h, purified by DCM:MeOH (95:5). Product was recovered as a colorless oil (34.3 mg, 40% yield). Rf=0.3 (DCM/MeOH=4.5:0.5). $^1$H NMR (400 MHz, CDCl$_3$) δ 7.31-7.27 (m, 2H), 7.24-7.16 (m, 4H), 6.96-6.94 (m, 2H), 6.80-6.78 (m, 2H), 3.81 (s, 3H), 3.71 (m, 2H), 2.68-2.64 (m, 2H), 1.79-1.74 (m, 2H), 1.20 (s, 6H), 1.78-1.71 (m, 1H), 1.64-1.60 (m, 1H). $^{13}$C NMR (101 MHz, CDCl$_3$) δ 159.83, 143.17, 129.54, 128.51, 128.46, 125.79, 120.67, 113.95, 112.35, 55.34, 52.87, 46.85, 42.97, 30.75, 27.53. HRMS (ESI-MS): calcd. 284.2008 [M+H]+ Found: 284.2007.

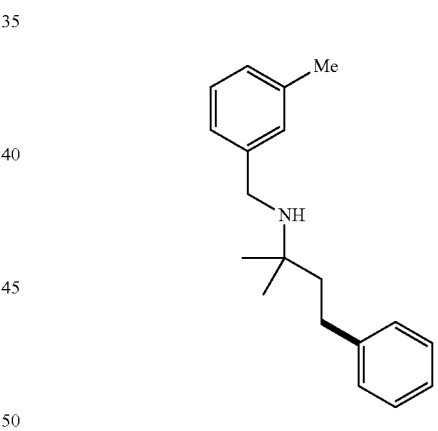

2-Methyl-N-(3-methylbenzyl)-4-phenylbutan-2-amine (3i)

Reaction time 14 h, purified by DCM:MeOH (97:3). Product was recovered as a colorless oil (32.1 mg, 40% yield). Rf=0.5 (DCM/MeOH=4.5:0.5). $^1$H NMR (400 MHz, CDCl$_3$) δ 7.33-7.29 (m, 2H), 7.24-7.16 (m, 6H), 7.08 (d, J=8.0 Hz, 1H), 3.71 (s, 2H), 2.70-2.66 (m, 2H), 2.37 (s, 3H), 1.81-1.77 (m, 2H), 1.23 (s, 6H). $^{13}$C NMR (101 MHz, CDCl$_3$) δ 143.15, 141.33, 137.15, 129.17, 128.48, 128.45, 128.43, 127.66, 125.76, 125.42, 52.83, 46.86, 42.87, 30.75, 27.54, 21.56. HRMS (ESI-MS): calcd. 268.2066 [M+H]+ Found: 268.2063.

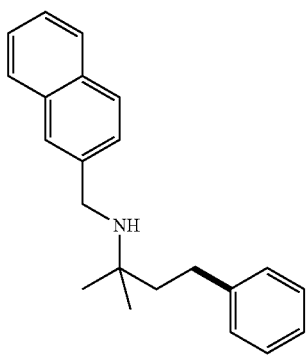

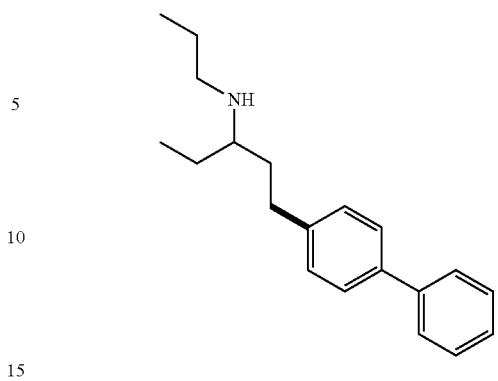

1-(1,1'-Biphenyl-4-yl)-N-propylpentan-3-amine (3l)

Reaction time 14 h, purified by DCM:MeOH (95:5). Product was recovered as a colorless oil (25.4 mg, 31% yield). Rf=0.3 (DCM/MeOH=4.5:0.5). $^1$H NMR (400 MHz, CDCl$_3$) δ 7.58 (d, J=8.0 Hz, 2H), 7.52 (d, J=8.0 Hz, 2H), 7.43 (d, J=8.0 Hz, 2H), 7.35-7.33 (m, 1H), 7.28 (d, J=8.0 Hz, 2H), 2.71-2.67 (m, 2H), 2.58-2.51 (m, 3H), 1.78-1.73 (m, 2H), 1.54-1.47 (m, 4H), 0.95-0.90 (m, 6H). $^{13}$C NMR (101 MHz, CDCl$_3$) δ 141.98, 141.22, 138.77, 128.87, 128.83, 127.28, 127.21, 127.11, 58.50, 49.06, 35.42, 31.90, 26.44, 23.75, 12.10, 10.06. HRMS (ESI-MS): calcd. 282.2222 [M+H]+ Found: 282.2218.

Example II—Carbon Dioxide-Mediated C(Sp2)-H Arylation of Primary and Secondary Benzylamines C—C bond formation by transition metal-catalyzed C—H activation is an important strategy to fabricate new bonds in a rapid fashion. Despite the pharmacological importance of ortho-arylbenzylamines, however, effective ortho-C—C bond formation of free primary and secondary benzylamines using Pd$^{II}$ remains an outstanding challenge. In this example, a method for constructing ortho-arylated primary and secondary benzylamines mediated by carbon dioxide (CO$_2$) is demonstrated. The use of CO$_2$ with Pd is important for allowing this transformation to proceed under relatively mild conditions, and mechanistic studies indicate that it (CO$_2$) is directly involved in the rate determining step. Furthermore, the milder temperatures furnish free amine products that can be directly used or elaborated without the need for deprotection. In cases where diarylation is possible, an interesting chelate effect is shown to facilitate selective monoarylation.

Amines are a ubiquitous functional group, being especially important in polymers and pharmaceuticals. Despite many classical and modern approaches to their synthesis, however, new methods are still in demand to access new chemical space surrounding these functional groups. One strategy for preparing amines is to functionalize C—H bonds through C—H activation and C—H functionalization methods. These approaches can allow rapid access to compounds that were either inaccessible with conventional synthetic methods, or required more lengthy synthetic routes, thereby expediting and improving drug library synthesis. Although primary and secondary aliphatic amines often require pre-functionalization with static directing groups to facilitate C—H bond activation and prevent undesirable substrate oxidation under palladium-catalyzed protocols, aromatic C—H bonds have generally been more easily

2-Methyl-N-(naphthalen-2-ylmethyl)-4-phenylbutan-2-amine (3j)

Reaction time 13 h, purified by DCM:MeOH (96:4). Product was recovered as a colorless oil (33.5 mg, 37% yield). Rf=0.4 (Hex/EtOAc=1:1). $^1$H NMR (400 MHz, CDCl$_3$) δ 7.84-7.80 (d, J=8.0 Hz, 4H), 7.50 (dd, J=8.0, 4.0 Hz, 1H), 7.47-7.44 (m, 2H), 7.31-7.27 (m, 2H), 7.23-7.17 (m, 3H), 3.90 (s, 2H), 2.72-2.68 (m, 2H), 1.84-1.80 (m, 2H), 1.25 (s, 6H). $^{13}$C NMR (101 MHz, CDCl$_3$) δ 143.12, 133.62, 132.70, 128.52, 128.46, 128.15, 128.78, 128.75, 127.07, 126.48, 126.05, 125.80, 125.58, 53.06, 47.02, 42.99, 30.80, 27.57. HRMS (ESI-MS): calcd. 304.2066 [M+H]+ Found: 304.2076.

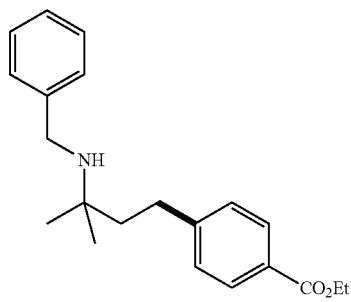

Ethyl 4-(3-(benzylamino)-3-methylbutyl)benzoate (3k)

Figure 22:
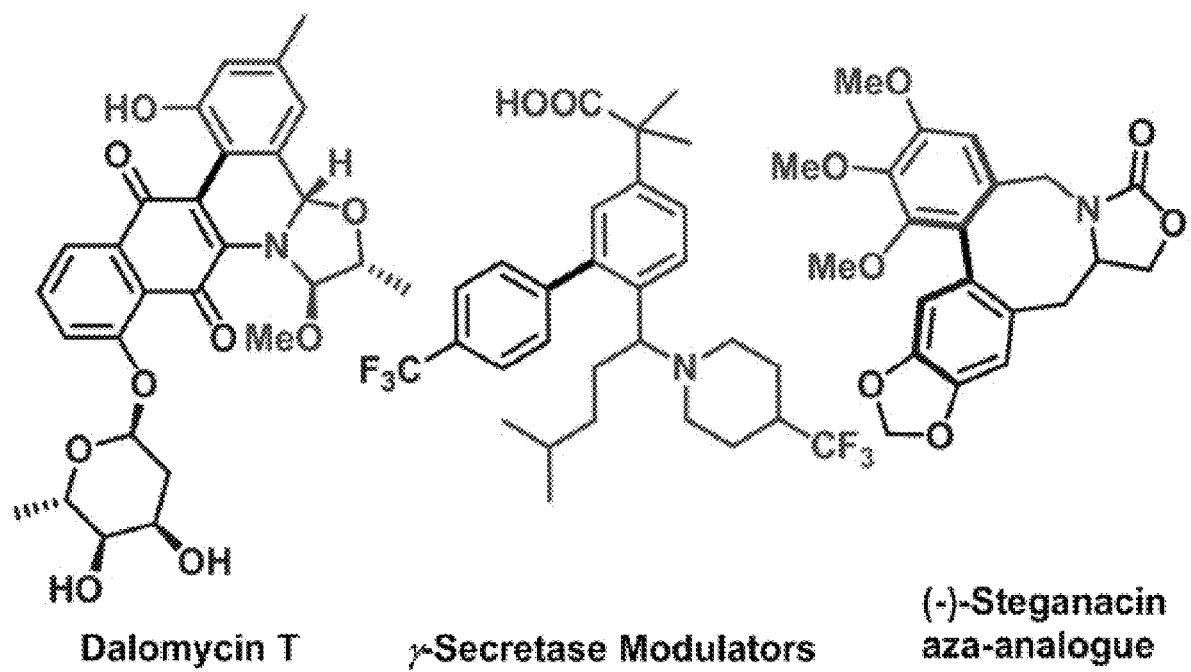
FIG. 22: Examples of biologically active ortho-aryl benzylamines.

Reaction time 13 h, purified by DCM:MeOH (95:5). Product was recovered as a colorless oil (31.1 mg, 32% yield). Rf=0.35 (Hex/EtOAc=1:1). $^1$H NMR (400 MHz, CDCl$_3$) δ 7.94 (d, J=8.0 Hz, 2H), 7.44-7.38 (m, 2H), 7.32 (t, J=8.0 Hz, 2H), 7.24-7.21 (m, 3H), 4.36 (q, J=8.0 Hz, 2H), 3.75 (s, 2H) 2.73-2.69 (m, 2H), 1.83-1.79 (m, 2H), 1.39 (t, J=8.0 Hz, 3H), 1.26 (s, 6H). $^{13}$C NMR (101 MHz, CDCl$_3$) δ 166.74, 147.96, 129.84, 129.15, 128.67, 128.42, 128.26, 127.61, 60.95, 53.59, 46.67, 41.99, 30.72, 26.68, 14.52. LRMS (ESI-MS): calcd. 326.01 [M+H]+ Found: 326.00.

targeted. For this reason, free homobenzylamines have been used as substrates for a variety of palladium-catalyzed C—H activation reactions without the need to pre-functionalize the amine. However, there has been a lack of examples in the literature whereby free primary ortho-aryl benzylamines can be directly accessed via C—H arylation, and there is still no method for the same transformation on free secondary benzylamine substrates or any method to do either transformation while preserving the chirality of the starting amine. Because of the importance of the biaryl moiety in a number of biologically-active molecules (FIG. 22), the ability to directly access free primary and secondary ortho-aryl benzylamines directly under mild conditions is very useful.

Ortho-aryl benzylamines are generally prepared directly from biaryl nitriles via reduction or an azidation/reduction sequence, also from a pre-formed biaryl species. Alternatively, they can be prepared from protected benzylamines via Suzuki-Miyaura cross-coupling or directed C—H arylation. However, it was not until 2006 that the first example of Pd-catalyzed ortho-arylation utilizing free primary and secondary benzylamines as substrates was shown. Though the arylation strategy was successful, the harsh conditions led to partial protection of the substrate and product acetamides, which led to the need to fully protect the amines for isolation. Furthermore, the substrate scope of secondary amines was limited to those without β-hydrogens. Subsequent strategies have emerged for C—H arylation, carbonylation, olefination, and even a Catellani-type reaction of tertiary benzylamines using Pd as a catalyst, as well as one example of the carbonylation/lactamization of free primary benzylamines, yet no improvements have been made on C—H arylation of secondary benzylamines, and only one report has improved on the arylation of primary benzylamines.

Some efforts in the field of C—H activation field have moved towards use of transient directing groups that can be formed in situ. Though more frequently applied to aldehyde and ketone-based substrates, this has also been achieved more recently using amine substrates combined with aldehyde-based directing groups. In Example I above it is shown that γ-arylation of aliphatic amines can be achieved in the presence of carbon dioxide. Mechanistic experiments indicated the idea of a transient carbamate serving as a directing as well as protecting group, thereby facilitating the desired C—H activation step. Therefore, carbon dioxide may facilitate the realization of a C—H activation strategy towards free primary and secondary ortho-arylbenzylamines.

To investigate the feasibility of utilizing carbon dioxide to facilitate the γ-C(sp$^2$)-H arylation of benzylamines, the substrate 2-(2-fluorophenyl)butan-2-amine was utilized. Surprisingly, the conditions for aliphatic amines, using Pd(OAc)$_2$ as pre-catalyst, AgTFA as an additive, and acetic acid as solvent, gave product, albeit in only modest yield. The reactions were performed in 2 dram reaction vials by combination of the reagents and solvent, followed by addition of carbon dioxide in the form of dry ice. Despite numerous examples in Example 1 where C(sp$^3$)-H arylation was exclusively observed for secondary benzylamines (believed to be due to possessing a more favorable conformation), only C(sp$^2$)-H arylation was observed in the current example. After significant screening, it was established that the optimal reaction conditions involved using Pd(OAc)$_2$ as pre-catalyst, with AgTFA as an additive, along with a mixture (7:3) of HFIP (hexafluoroisopropanol):acetic acid as solvent, in the presence of approximately 5 eq of CO$_2$ added in the form of dry ice. Although Ag salts may be used simply as halide scavengers, less than one turnover was achieved when silver trifluoroacetate was omitted, indicating more than one role in this transformation. Omission of palladium completely shut down the reaction. The reaction is greatly enhanced by CO$_2$, and only 9% yield was obtained in the absence of additional CO$_2$.

With the optimized conditions in hand, the substrate scope of the transformation with regard to aryl halides (Table 4, FIG. 23) was evaluated. Using the optimized conditions, the standard product was isolated in 71% yield (4a). The reaction could be performed on a number of fluorinated aryl iodides (4b-4f), as well as those with more electron deficient groups such as esters (4g and 4h), nitro groups (4i and 4j), ketones (4k), and even multiple electron deficient groups (4l). It is noteworthy that neither the ketone nor the isophthalate groups show signs of condensation or substitution with the amine under the reaction conditions. Reactions with either bromoiodobenzene (4m) or diiodobenzene (4n) could be performed without reactivity at the second halogen. Electron rich aryl iodides bearing indole rings (4o), methyl groups (4p and 4q), methoxy groups (4r and 4s), both difluoro and trifluoromethoxy groups (4t-4v), and even an arene with extended conjugation (4w) were also tolerated during the reaction. Surprisingly, 2-iodostrychnine can be used in the reaction (4x) despite the presence of a tertiary amine that can also react with CO$_2$. Furthermore, the conditions are mild enough to preserve both the amide and allylic ether groups.

Next, the scope of the reaction with respect to the amine substrates was evaluated. Short to medium length aliphatic chains could be tolerated, all with excellent selectivity for C(sp$^2$)-H arylation (Table 5, FIG. 24, 5a-5d). Moving the position of the fluoro substituent on the benzylamine (5e) as well as using substrates bearing either an o- or m-chloro group (5f and 5g) all gave good yields. More electron rich benzylamines with methyl (5h) and methoxy (5i) substituents were also tolerated in the reaction. Amines with both benzylic and homobenzylic sites showed complete selectivity for γ-arylation on the benzyl rather than δ-arylation on the homobenzylic chain (5j and 5k), which is believed to be due to a faster rate of C—H activation. No changes were necessary to apply this protocol to more oxidatively-sensitive α-primary benzylamines, and the corresponding o-biaryls could be prepared without concomitant oxidation of the benzylamine (5l and 5m). Even α-secondary benzylamines, which can undergo β-hydride elimination to generate imines during the reaction, gave the unoxidized amine products in excellent yields (5n-5p).

Based on the previous success applying carbon dioxide to the functionalization of secondary amines, it was believed it may help prevent oxidation problems that had previously limited the substrate scope. The optimized conditions were found to indeed promote the C—H arylation of secondary benzylamines while preventing deleterious oxidation pathways. Substrates bearing linear (Table 6, FIG. 25, 6a) and branched (6b-6d) chains added to the benzylamine were able to participate in the reaction. Amines bearing various carbocycles (6e-6g) were also viable under the standard reaction conditions. Aryl groups could be added to the benzylamine via either a β (6h) or γ (6i) linkage without degraded regioselectivity for arylation of the γ-C(sp$^2$)-H bond. Surprisingly, unsaturated (6j) as well as saturated (6k-6o) heterocycles appended to the benzylamine could also survive the reaction conditions, although it is worth noting that appending an N-methylpyrrole moiety to the benzylamine failed to give product under these conditions. Without wishing to be bound by theory, it is believed that this was due to its increased nucleophilicity.

A common issue in the intermolecular o-C(sp$^2$)-H activation literature is the challenge of achieving selective mono-functionalization without blocking the 2-position or sterically protecting the 2-position by pre-installation of a group at the 3-position. It was found that in the absence of a substituent at the 2 or 3-position, diarylation products were afforded with great selectivity when excess aryl halide was used (Table 7, FIG. 26), although dropping the ratio to less than five equivalents of halide led to a mixture of mono and di-arylation products. Without wishing to be bound by theory, it is believed that although the reactive C—H bond is not forced towards the catalyst during the initial reaction, after arylation the aromatic ring will adopt a conformation where the second o-C—H bond becomes more accessible, leading to faster C—H activation of the monosubstituted benzylamines compared to the unsubstituted starting material. The m-terphenyl products could be achieved with α-tertiary benzylamines without (7a) or with (7b and 7c) a substituent at the 4'-position of the benzylamine. Notably, a chiral amine survived the reaction with no loss of chirality (7b). α-Primary benzylamines are also viable substrates in the reaction (7d and 7e).

By using 4-phenyl iodobenzene as the electrophile, it is even possible to rapidly access a highly conjugated m-pentaphenyl with an amine moiety (7f). Substrates containing both benzylic and homobenzylic positions also still gave complete selective for diarylation of solely the benzylic ring (7g and 7h). Given the ability to synthesize highly conjugated substrates, a bis-fluorene (7i) was next targeted, although this was not particularly emissive. Finally, use of a β-phenylalanine ester also led to the diarylation products in good yield with no observable α-arylation (7j) of either the amine or ester group.

While exploring the diarylation of benzylamines, an interesting outlier was discovered: subjecting methyl phenylglycine to the reaction conditions led to selective monoarylation (Table 8, FIG. 27, 8a), even without utilizing the blocking method. It was believed there might be a chelation effect from the pendant ester that leads to the unusual selectivity. Despite the addition of a third group to lower the pKa of the α-proton, retention of configuration of the chiral amine was still observed. Based on this result, a number of other substrates with chelating groups were explored: replacing the ester with an amide (8b-8d) still led to monoarylation when only three equivalents of aryl halide were utilized. Notably, the free amide required a slight modification to the conditions (8d). While the presence of a β-carbonyl was clearly effective, whether other groups might facilitate this monoarylation was evaluated, and it was found that placing an alcohol 3 to the amine could also prevent diarylation (8e). Protection of the alcohol as an ester was also effective in the selective monoarylation (8f). Surprisingly, even an α-phosphonate ester could be used to achieve selective monoarylation (8g). The effect was also observed with a tertiary β-thiol as well as an α-nitrile, although the products of these reactions could not be successfully purified. Interestingly, the α-nitrile gave rise to the ortho-aryl aminoacid due to hydrolysis of the nitrile.

After gaining a better understanding of the substrate scope, the utility of the reaction was demonstrated with a known synthetic target. This C—H arylation approach was applied to a key step in the synthesis of Anacetrapib, a CETP inhibitor. The requisite aryl halide can be synthesized in three steps, and although ortho-substituted aryl halides are generally poor substrates for C—H arylation reactions, by using AgOTf as the additive, the o-biaryl can be achieved in 42%. The use of Ag additives with relatively poorly coordinating counterions for C—H arylation with o-substituted iodoarenes is a relatively reliable approach for using these more sterically-hindered aryl halide substrates. The amine can then be treated with the corresponding epoxide and cyclized to give Anacetrapib using a known procedure.

To demonstrate the synthetic utility for this chemistry, whether the reactions could be performed on larger scale was evaluated (Scheme 5, FIG. 28). Performing the reaction at 100 times the scale (from 0.15 mmol to 15 mmol) gave a similar yield (Scheme 5a, FIG. 28). Whether higher than 1 atmosphere of $CO_2$ pressure was still needed at this scale was also evaluated, and so the reaction was conducted under standard Schlenk conditions with 1 atmosphere of $CO_2$. Under these conditions, the yield was less than half (Scheme 5b, FIG. 28), showing that the pressure of $CO_2$ is important for the optimal functioning of this chemistry.

Having demonstrated the synthetic utility of the approach, the mechanism of this C—H arylation was evaluated. Control reactions indicated a vital role for $CO_2$ during the reaction, yet cyclopalladated intermediates of primary and secondary benzylamines have been made before under relatively mild conditions without the need for an additional directing group. Whether or not $CO_2$ was acting as a directing group, or serving in a separate capacity, was evaluated. One possibility would be that dimeric species that might be present that $CO_2$ disrupts, although these are believed to be destabilized under acidic conditions, and so this was not considered to be a likely cause.

Figure 30A:
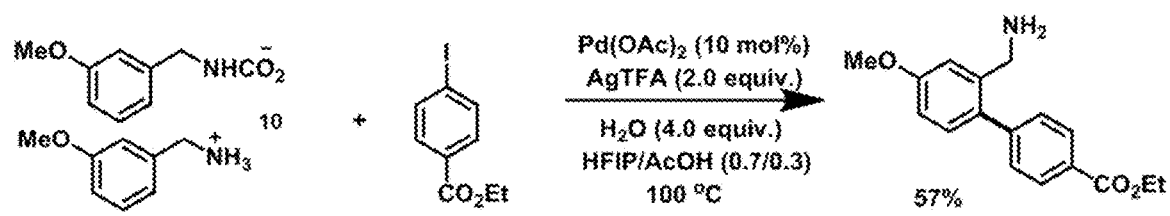
FIGS. 30A-30E: Mechanistic studies on the $CO_2$-mediated C—H arylation of benzylamines.
Figure 30B:
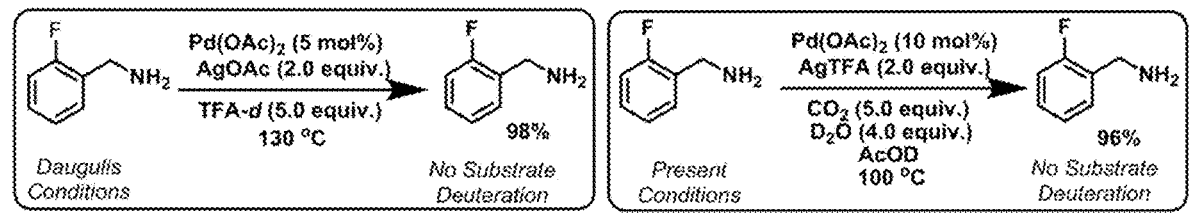
Figure 30C:
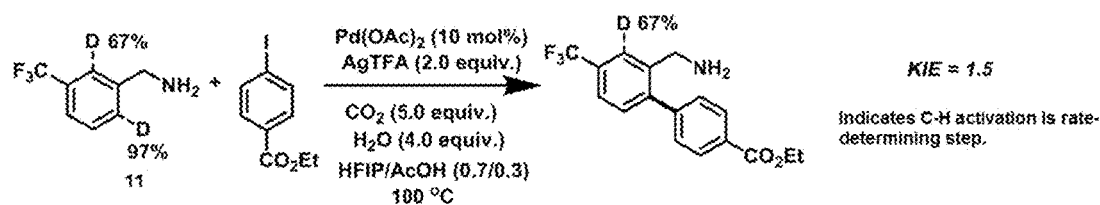

To probe the mechanism experimentally, whether or not substoichiometric carbon dioxide was sufficient to catalyze the reaction was evaluated (FIG. 30A). The ammonium carbamate salt 10 was prepared, which would introduce only a half equivalent of carbon dioxide into the reaction. This gave 57% yield in the arylation reaction (1n the absence of additional $CO_2$), indicating that catalytic loading of $CO_2$ was satisfactory for the reaction to proceed (although considering the results in Scheme 5b (FIG. 28), there is some importance to the $CO_2$ pressure, regardless of the stoichiometry). Next, whether the C—H activation step was reversible was probed. Using different conditions in the presence of fully deuterated solvents, no deuteration was observed (FIG. 30B). To further explore this, the rate of reaction was compared between the proteo and deutero substrates under the conditions used in these examples, and was found to exhibit a kinetic isotope effect of ~1.5, providing additional evidence that the rate-determining step is the initial breaking of the C—H bond (FIG. 30C).

Figure 30D:
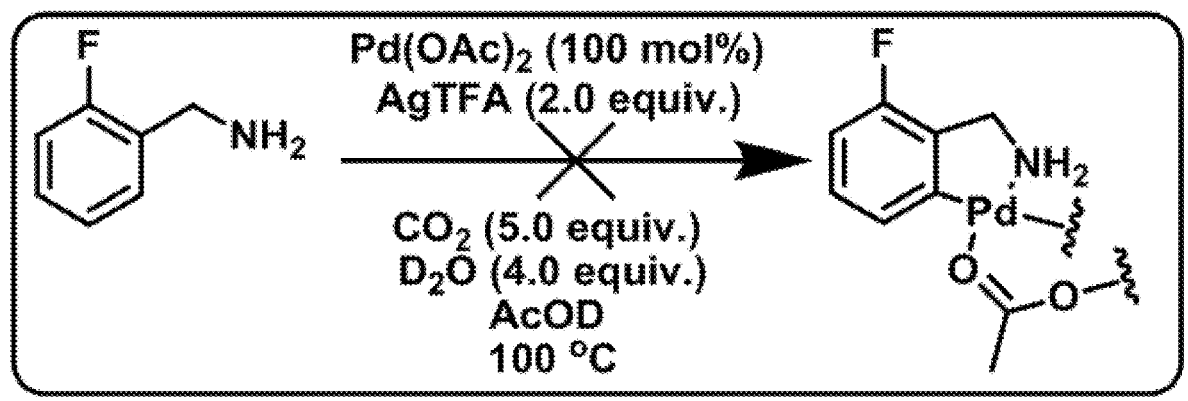
Figure 30E:
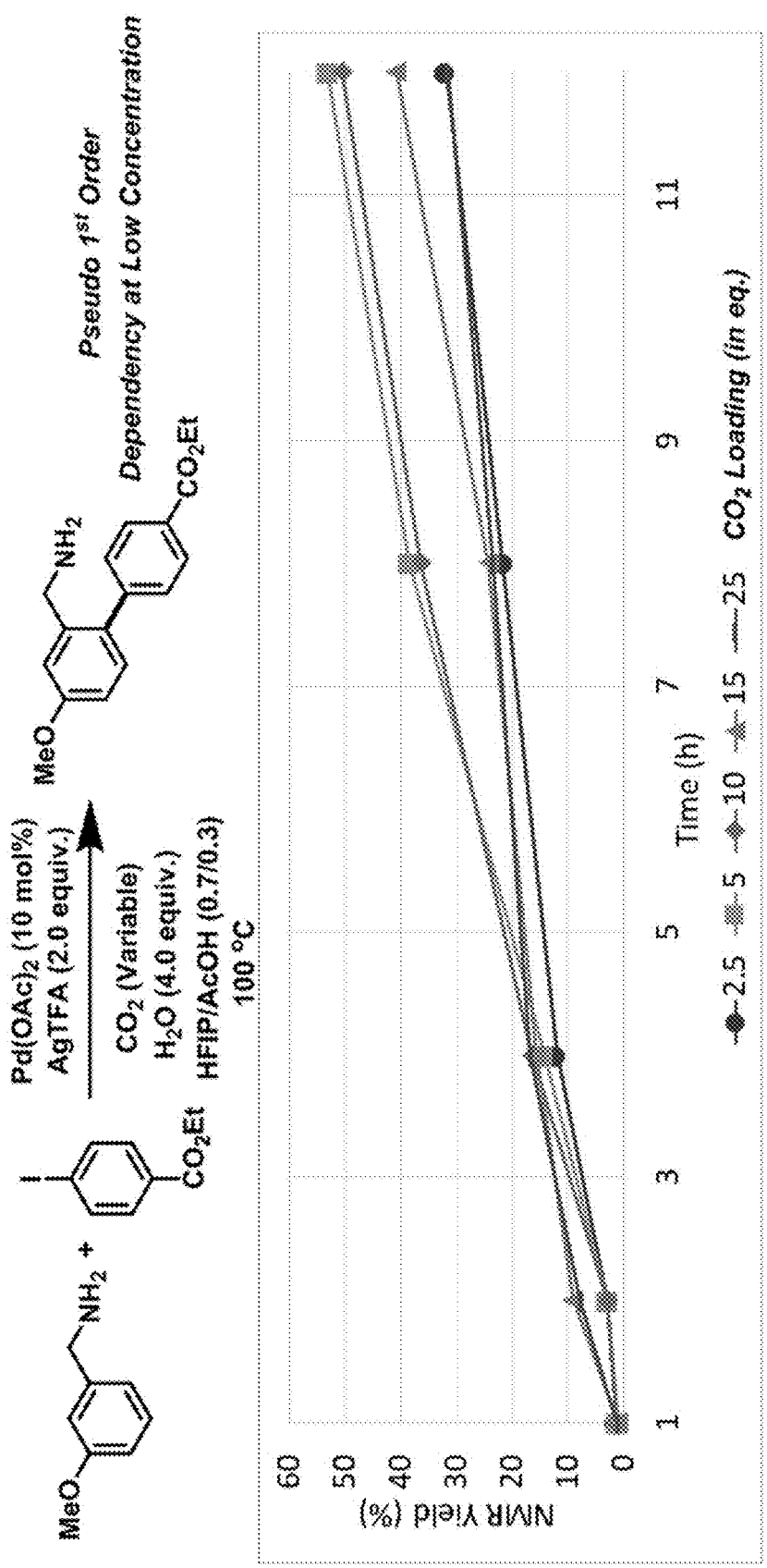

Considering that C—H activation is rate determining, but also that C—H metalation should actually be facile, whether C—H palladation was likely to occur readily in the absence of $CO_2$ was evaluated. When the cyclometallation was attempted with stoichiometric Pd(OAc)$_2$ in neat acetic acid, however, negligible C—H activation was observed (FIG. 30D), indicating that at least under the reaction conditions, the barrier to C—H activation is higher under the conditions than it is in solvents such as chloroform. This indicates that $CO_2$ indeed is serving as a directing group under the catalytic conditions. Without wishing to be bound by theory, it is believed that if $CO_2$ is serving as a directing group the overall rate of arylation should also exhibit $1^{st}$ order rate dependency on the concentration of $CO_2$. For this reason, the rate of reaction at varied loadings of $CO_2$ was explored (FIG. 30E). At low concentrations of $CO_2$ (2.5 and 5 mol. equivalents), pseudo $1^{st}$ order rate dependency was observed, with the yield at 12 h of reaction time being almost doubled when the amount of $CO_2$ was doubled. This supports the conclusion that $CO_2$ is involved in the rate determining C—H activation step. Notably, as the amount of $CO_2$ was increased beyond 5 mol. equivalents, the reaction yield began to decrease. Although this may due to activation of the amine by $CO_2$ and subsequent decomposition to the Pd-7π-allyl, analysis of the reaction mixture did not show any obvious decomposition products from such a pathway, indicating a more complex roll for $CO_2$ than only serving as a directing group.

In summary, this example demonstrates how carbon dioxide can be used to achieve ortho-arylation of benzylamine substrates under milder conditions than the free amine alone, or from using an aldehyde-based transient directing group approach. This allows a broad substrate scope of primary benzylamines, while simultaneously allowing oxidatively-sensitive secondary benzylamines to participate in the reaction. By appending chelating groups 3 to the amine, it has even been shown how unblocked benzylamine substrates can be selectively monoarylated due to a putative chelate effect.

Example III—Other Reactions

Figure 31:
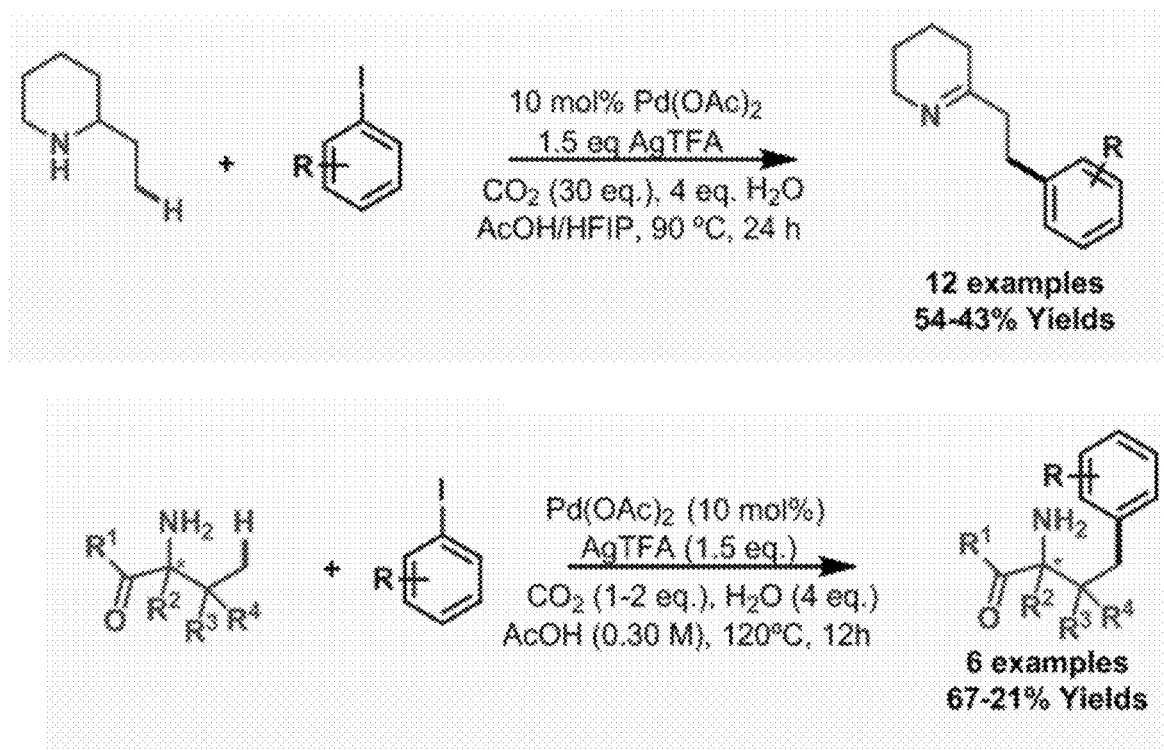
FIG. 31: Schemes depicting examples of $C(sp^3)$-H functionalization.
Figure 32:
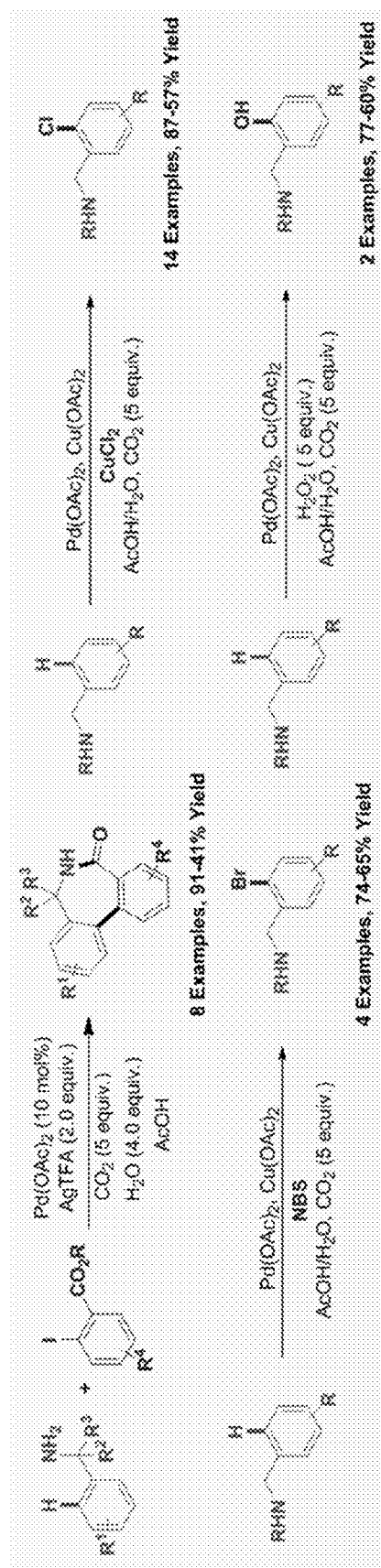
FIG. 32: Schemes depicting examples of benzylamine $C(sp^2)$-H functionalization.
Figure 33:
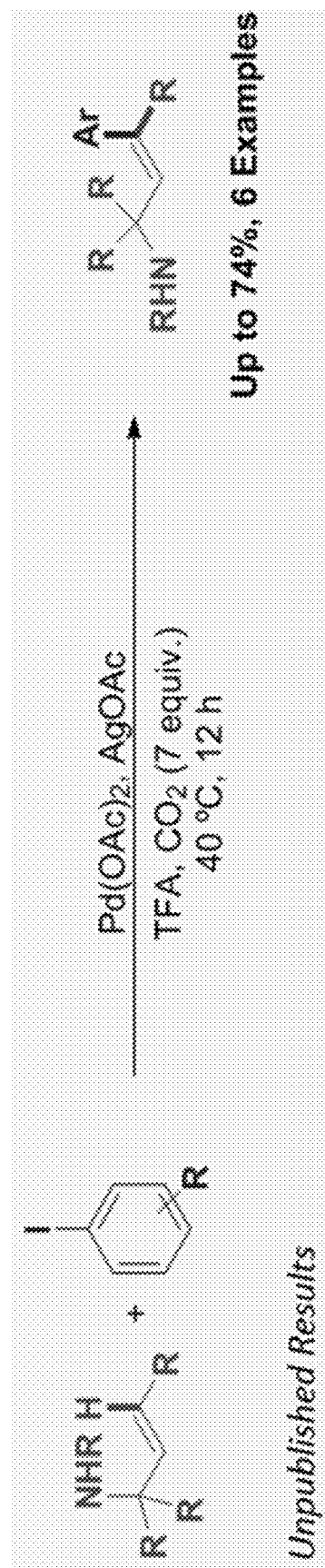
FIG. 33: Schemes depicting examples of allylamine $C(sp^2)$-H functionalization.

The method described herein is also useful for other $C(sp^3)$-H functionalization, other benzylamine $C(sp^2)$-H functionalization, and allylamine $C(sp^2)$-H functionalization, as shown FIGS. 31-33. FIG. 31 shows schemes depicting examples of $C(sp^3)$-H functionalization. Some of these compounds may have opioid-like activity. FIG. 32 shows schemes depicting examples of benzylamine $C(sp^2)$-H functionalization in addition to those demonstrated in Example II. FIG. 33 shows schemes depicting examples of allylamine $C(sp^2)$-H functionalization. The allylamines are useful for a number of applications, including as antihistimines or antifungals. The reaction can also be applied to alcohols, albeit not in the same yields as amines.

Certain embodiments of the methods and compositions disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A method of functionalizing a C—H bond, the method comprising using $CO_2$ as a directing group to convert a C—H bond in a substrate compound into a C—C bond by reacting the substrate compound with an aryl halide in the presence of a transition metal catalyst and $CO_2$ as a gas or a solid, wherein the substrate compound comprises a primary or secondary amine functional group and the C—H bond is in a gamma position relative to the amine functional group.

2. The method of claim 1, wherein the transition metal catalyst comprises palladium.

3. The method of claim 1, wherein the amine is a primary amine.

4. The method of claim 3, wherein the primary amine is selected from the group consisting of: 1-ethylcyclopentan-1-amine (S-1), 1-ethylcyclohexan-1-amine (S-2), 1-ethylcycloheptan-1-amine (S-3), 4-(tert-butyl)-1-ethylcyclohexan-1-amine (S-4), 9-ethyl-9H-fluoren-9-amine (S-5), 3-methylheptan-3-amine (S-6), 3-methylnon-3-amine (S-7), 3-methylpentan-3-amine (S-8), 3-ethylpentan-3-amine (S-9), and heptan-3-amine (5-10).

5. The method of claim 1, wherein the amine is a secondary amine.

6. The method of claim 5, wherein the secondary amine is selected from the group consisting of: N-(tert-pentyl)propan-1-amine (5-12), N-(tert-pentyl)butan-1-amine (5-13), N-(tert-pentyl)pentan-1-amine (5-14), 2-methyl-N-phenethylbutan-2-amine (S-15), N-benzyl-2-methylbutan-2-amine (S-16), N-(4-methoxybenzyl)-2-methylbutan-2-amine (5-17), N-(3-methoxybenzyl)-2-methylbutan-2-amine (5-18), N-(4-tolyl)-2-methylbutan-2-amine (5-19), N-(3-tolyl)-2-methylbutan-2-amine (S-20), and N-propylpentan-2-amine (S-22).

7. The method of claim 1, wherein the amine is 6-ethyl-3,3,9,9-tetraisopropyl-2,10-dimethyl-4,8-dioxa-3,9-disi-laundecan-6-amine (5-11).

8. The method of claim 1, wherein the aryl halide comprises an iodoaromatic compound.

9. The method of claim 8, wherein the iodoaromatic compound is selected from the group consisting of: phenyl iodide, 3-iodoisocoumarin (S-23), 5-iodo-1-tosyl-1H-indole (S-24), 1-ethoxy-4-iodobenzene (S-25), and 1-benzyloxy-4-iodobenzene (S-26).

10. The method of claim 8, wherein the aryl halide comprises a heterocycle.

11. The method of claim 1, wherein the amine is a benzylamine.

12. The method of claim 1, wherein the amine is an allylamine.

13. A method of synthesizing a compound, the method comprising:
reacting a substrate having a primary or secondary amine functional group with a reactant in the presence of $CO_2$ as a gas or a solid and a transition metal catalyst to produce a compound,
wherein the substrate is functionalized at a γ-C—H position relative to the primary or secondary amine functional group to produce the compound, and
wherein the reactant is an aryl halide.

14. The method of claim 13, wherein the compound is a γ-arylated primary amine.

15. The method of claim 13, wherein the compound is 2-methyl-4-phenylbutan-2-amine (1a), 4-(3-fluorophenyl)-2-methylbutan-2-amine (1b), 4-(4-fluorophenyl)-2-methylbutan-2-amine (1c), 2-methyl-4-[3-(trifluoromethyl)phenyl]butan-2-amine (1d), 2-methyl-4-[4-(trifluoromethyl)phenyl]butan-2-amine (1e), ethyl 2-(3-amino-3-methylbutyl)benzoate (1f), ethyl 3-(3-amino-3-methylbutyl)benzoate (1g), ethyl 4-(3-amino-3-methylbutyl)benzoate (1h), 2-methyl-4-(3-nitrophenyl)butan-2-amine (1i), 2-methyl-4-(4-nitrophenyl)butan-2-amine (1j), 4-[3,5-bis(trifluoromethyl)phenyl]-2-methylbutan-2-amine (1k), dimethyl 5-(3-amino-3-methylbutyl)isophthalate (1l), 4-(3-chloro-4-fluorophenyl)-2-methylbutan-2-amine (1m), 4-(4-bromophenyl)-2-methylbutan-2-amine (1n), 4-(4-iodophenyl)-2-methylbutan-2-amine (1o), 7-(3-amino-3-methylbutyl)-3,4-diphenyl-1H-isochromen-1-one (1p), 2-methyl-4-(N-tosyl-1H-indol-5-yl)butan-2-amine (1q), 4-(3-methoxyphenyl)-2-methylbutan-2-amine (1r), 4-(4-methoxyphenyl)-2-methylbutan-2-amine (1s), 4-(4-ethoxyphenyl)-2-methylbutan-2-amine (it), 4-(4-benzyloxyphenyl)-2-methylbutan-2-amine (1u), 2-methyl-4-(m-tolyl)

butan-2-amine (1v), 2-methyl-4-(p-tolyl)butan-2-amine (1w), 4-(1,1'-biphenyl-4-yl)-2-methylbutan-2-amine (1x), 2-methyl-4-(naphthalen-1-yl)butan-2-amine (1y), 4-(2-fluorophenyl)-2-methylbutan-2-amine (1z), 2-(3-amino-3-methylbutyl)phenol (1aa), 4-(2-methoxyphenyl)-2-methylbutan-2-amine (1ab), 4,4'-(1,4-phenylene)bis(2-methylbutan-2-amine) (1ac), 1-phenethylcyclopentanamine (2a), 1-phenethylcyclohexanamine (2b), 1-phenethylcycloheptanamine (2c), 4-(tert-butyl)-1-phenethylcyclohexanamine (2d), 9-phenethyl-9H-fluoren-9-amine (2e), 3-methyl-1-phenylheptan-3-amine (2f), 3-methyl-1-phenylnonan-3-amine (2g), 2-amino-2-phenethylpropane-1,3-diol (2h), 3-methyl-1-phenylpentan-3-amine (2i-mono), 3-methyl-1,5-diphenylpentan-3-amine (2i-di), 3-ethyl-1-phenylpentan-3-amine (2j-mono), 3-ethyl-1,5-diphenylpentan-3-amine (2j-di), 4-(1,1'-biphenyl-4-yl)butan-2-amine (2k), 1-(1,1'-biphenyl-4-yl)pentan-3-amine (2l), 1-(1,1'-biphenyl-4-yl)heptan-3-amine (2m), or 4-(1,1'-biphenyl-4-yl)-3,3-dimethylbutan-2-amine (2n).

16. The method of claim 13, wherein the compound is a γ-arylated secondary amine.

17. The method of claim 16, wherein the γ-arylated secondary amine is selected from the group consisting of: 4-(1,1'-biphenyl-4-yl)-2-methyl-N-propylbutan-2-amine (3a), N-[4-(1,1'-biphenyl-4-yl)-2-methylbutan-2-yl]butan-1-amine (3b), N-[4-(1,1'-biphenyl-4-yl)-2-methylbutan-2-yl]pentan-1-amine (3c), 2-methyl-N-phenethyl-4-phenylbutan-2-amine (3d), N-benzyl-2-methyl-4-phenylbutan-2-amine (3e), N-(4-methoxybenzyl)-2-methyl-4-phenylbutan-2-amine (3f), N-(3-methoxybenzyl)-2-methyl-4-phenylbutan-2-amine (3g), 2-methyl-N-(4-methylbenzyl)-4-phenylbutan-2-amine (3h), 2-methyl-N-(3-methylbenzyl)-4-phenylbutan-2-amine (3i), 2-methyl-N-(naphthalen-2-ylmethyl)-4-phenylbutan-2-amine (3j), ethyl 4-(3-(benzylamino)-3-methylbutyl)benzoate (3k), and 1-(1,1'-biphenyl-4-yl)-N-propylpentan-3-amine (3l).

18. A method of functionalizing a C—H bond, the method comprising using $CO_2$ as a directing group to convert a C—H bond in a substrate compound into a C—C bond in the presence of a transition metal catalyst, wherein the substrate compound comprises a primary or secondary amine functional group, and the substrate compound is functionalized at a gamma C—H position relative to the primary or secondary amine functional group, wherein the substrate compound is selected from the group consisting of: 1-ethylcyclopentan-1-amine (S-1), 1-ethylcyclohexan-1-amine (S-2), 1-ethylcycloheptan-1-amine (S-3), 4-(tert-butyl)-1-ethylcyclohexan-1-amine (S-4), 9-ethyl-9H-fluoren-9-amine (S-5), 3-methylheptan-3-amine (S-6), 3-methylnon-3-amine (S-7), 3-methylpentan-3-amine (S-8), 3-ethylpentan-3-amine (S-9), heptan-3-amine (S-10), N-(tert-pentyl)propan-1-amine (S-12), N-(tert-pentyl)butan-1-amine (S-13), N-(tert-pentyl)pentan-1-amine (S-14), 2-methyl-N-phenethylbutan-2-amine (S-15), N-benzyl-2-methylbutan-2-amine (S-16), N-(4-methoxybenzyl)-2-methylbutan-2-amine (S-17), N-(3-methoxybenzyl)-2-methylbutan-2-amine (S-18), N-(4-tolyl)-2-methylbutan-2-amine (S-19), N-(3-tolyl)-2-methylbutan-2-amine (S-20), N-propylpentan-2-amine (S-22), and 6-ethyl-3,3,9,9-tetraisopropyl-2,10-dimethyl-4,8-dioxa-3,9-disilaundecan-6-amine (S-11).

19. A method of synthesizing a compound, the method comprising:

reacting a substrate having a primary or secondary amine functional group with a reactant in the presence of $CO_2$ and a transition metal catalyst to produce a compound, wherein the substrate is functionalized at a γ-C—H position relative to the amine functional group to produce the compound, and wherein the compound is a γ-arylated primary amine or a γ-arylated secondary amine selected from the group consisting of: 2-methyl-4-phenylbutan-2-amine (1a), 4-(3-fluorophenyl)-2-methylbutan-2-amine (1b), 4-(4-fluorophenyl)-2-methylbutan-2-amine (1c), 2-methyl-4-[3-(trifluoromethyl)phenyl]butan-2-amine (1d), 2-methyl-4-[4-(trifluoromethyl)phenyl]butan-2-amine (1e), ethyl 2-(3-amino-3-methylbutyl)benzoate (1f), ethyl 3-(3-amino-3-methylbutyl)benzoate (1g), ethyl 4-(3-amino-3-methylbutyl)benzoate (1h), 2-methyl-4-(3-nitrophenyl)butan-2-amine (1i), 2-methyl-4-(4-nitrophenyl)butan-2-amine (1j), 4-[3,5-bis(trifluoromethyl)phenyl]-2-methylbutan-2-amine (1k), dimethyl 5-(3-amino-3-methylbutyl)isophthalate (1l), 4-(3-chloro-4-fluorophenyl)-2-methylbutan-2-amine (1m), 4-(4-bromophenyl)-2-methylbutan-2-amine (1n), 4-(4-iodophenyl)-2-methylbutan-2-amine (1o), 7-(3-amino-3-methylbutyl)-3,4-diphenyl-1H-isochromen-1-one (1p), 2-methyl-4-(N-tosyl-1H-indol-5-yl)butan-2-amine (1q), 4-(3-methoxyphenyl)-2-methylbutan-2-amine (1r), 4-(4-methoxyphenyl)-2-methylbutan-2-amine (1s), 4-(4-ethoxyphenyl)-2-methylbutan-2-amine (1t), 4-(4-benzyloxyphenyl)-2-methylbutan-2-amine (1u), 2-methyl-4-(m-tolyl)butan-2-amine (1v), 2-methyl-4-(p-tolyl)butan-2-amine (1w), 4-(1,1'-biphenyl-4-yl)-2-methylbutan-2-amine (1x), 2-methyl-4-(naphthalen-1-yl)butan-2-amine (1y), 4-(2-fluorophenyl)-2-methylbutan-2-amine (1z), 2-(3-amino-3-methylbutyl)phenol (1aa), 4-(2-methoxyphenyl)-2-methylbutan-2-amine (1ab), 4,4'-(1,4-phenylene)bis(2-methylbutan-2-amine) (1ac), 1-phenethylcyclopentanamine (2a), 1-phenethylcyclohexanamine (2b), 1-phenethylcycloheptanamine (2c), 4-(tert-butyl)-1-phenethylcyclohexanamine (2d), 9-phenethyl-9H-fluoren-9-amine (2e), 3-methyl-1-phenylheptan-3-amine (2f), 3-methyl-1-phenylnonan-3-amine (2g), 2-amino-2-phenethylpropane-1,3-diol (2h), 3-methyl-1-phenylpentan-3-amine (2i-mono), 3-methyl-1,5-diphenylpentan-3-amine (2i-di), 3-ethyl-1-phenylpentan-3-amine (2j-mono), 3-ethyl-1,5-diphenylpentan-3-amine (2j-di), 4-(1,1'-biphenyl-4-yl)butan-2-amine (2k), 1-(1,1'-biphenyl-4-yl)pentan-3-amine (2l), 1-(1,1'-biphenyl-4-yl)heptan-3-amine (2m), 4-(1,1'-biphenyl-4-yl)-3,3-dimethylbutan-2-amine (2n), 4-(1,1'-biphenyl-4-yl)-2-methyl-N-propylbutan-2-amine (3a), N-[4-(1,1'-biphenyl-4-yl)-2-methylbutan-2-yl]butan-1-amine (3b), N-[4-(1,1'-biphenyl-4-yl)-2-methylbutan-2-yl]pentan-1-amine (3c), 2-methyl-N-phenethyl-4-phenylbutan-2-amine (3d), N-benzyl-2-methyl-4-phenylbutan-2-amine (3e), N-(4-methoxybenzyl)-2-methyl-4-phenylbutan-2-amine (3f), N-(3-methoxybenzyl)-2-methyl-4-phenylbutan-2-amine (3g), 2-methyl-N-(4-methylbenzyl)-4-phenylbutan-2-amine (3h), 2-methyl-N-(3-methylbenzyl)-4-phenylbutan-2-amine (3i), 2-methyl-N-(naphthalen-2-ylmethyl)-4-phenylbutan-2-amine (3j), ethyl 4-(3-(benzylamino)-3-methylbutyl)benzoate (3k), and 1-(1,1'-biphenyl-4-yl)-N-propylpentan-3-amine (3l).

* * * * *

UNITED STATES PATENT AND TRADEMARK OFFICE
CERTIFICATE OF CORRECTION

PATENT NO. : 10,865,163 B2
APPLICATION NO. : 16/223467
DATED : December 15, 2020
INVENTOR(S) : Michael Young and Mohit Kapoor It is certified that error appears in the above-identified patent and that said Letters Patent is hereby corrected as shown below:

In the Claims

Column 52 Claim 4, Line 6, please correct from:
"(5-10)"

To:
--(S-10)--

Column 52 Claim 6, Line 11, Line 12, Line 15, and Line 16, please correct from:
"(5-12)" "(5-13) (5-14)" "(5-17)" "(5-18) (5-19)"

To:
--(S-12)-- --(S-13) (S-14)-- --(S-17)-- --(S-18) (S-19)--

Column 52 Claim 7, Line 21, please correct from:
"(5-11)"

To:
--(S-11)--

Column 52 Claim 15, Line 66, please correct from:
"(it)"

To:
--(1t)--

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*